(12) United States Patent
Yoshida et al.

(10) Patent No.: US 10,538,740 B2
(45) Date of Patent: Jan. 21, 2020

(54) METHOD FOR SORTING CARDIOMYOCYTES

(71) Applicant: KYOTO UNIVERSITY, Kyoto (JP)

(72) Inventors: Yoshinori Yoshida, Kyoto (JP); Hirohide Saito, Kyoto (JP); Kenji Miki, Kyoto (JP); Kei Endo, Kyoto (JP); Seiya Takahashi, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 15/127,134

(22) PCT Filed: Mar. 20, 2015

(86) PCT No.: PCT/JP2015/058466
§ 371 (c)(1),
(2) Date: Jul. 17, 2017

(87) PCT Pub. No.: WO2015/141827
PCT Pub. Date: Sep. 24, 2015

(65) Prior Publication Data
US 2017/0369846 A1 Dec. 28, 2017

(30) Foreign Application Priority Data
Mar. 20, 2014 (JP) ................. 2014-058926

(51) Int. Cl.
| | | |
|---|---|---|
| *C12N 5/077* | (2010.01) | |
| *C12N 5/00* | (2006.01) | |
| *C12N 5/0735* | (2010.01) | |
| *A61K 48/00* | (2006.01) | |

(52) U.S. Cl.
CPC ......... *C12N 5/0657* (2013.01); *C12N 5/0018* (2013.01); *C12N 5/0606* (2013.01); *A01K 2267/0375* (2013.01); *A61K 48/00* (2013.01); *C12N 2501/60* (2013.01); *C12N 2506/02* (2013.01); *C12N 2510/00* (2013.01)

(58) Field of Classification Search
CPC ............ C12N 5/0657; C12N 2310/141; C12N 2510/00
See application file for complete search history.

(56) References Cited

U.S. PATENT DOCUMENTS

2008/0152590 A1* 6/2008 Snyder ............... A61K 48/0008
424/9.1
2014/0073687 A1* 3/2014 Chien ................ A01K 67/0276
514/44 R

FOREIGN PATENT DOCUMENTS

| | | |
|---|---|---|
| EP | 3093348 A1 | 11/2016 |
| EP | 3170893 A1 | 5/2017 |
| JP | 2010-158206 | 7/2010 |
| WO | WO 2007002136 A2 | 1/2007 |
| WO | WO 2007069666 A1 | 6/2007 |
| WO | WO 2009/066758 A1 | 5/2009 |
| WO | WO 2009092005 A2 | 7/2009 |
| WO | WO 2009118928 A1 | 10/2009 |
| WO | WO 2011/154553 A2 | 12/2011 |
| WO | WO 2014014119 A1 | 1/2014 |
| WO | WO 2016171235 A1 | 10/2016 |

OTHER PUBLICATIONS

Subach et al. Chemistry & Biology 15(10): 1116-1124 (Year: 2008).*
Saito et al. Nature Communication 160, pp. 1-9 (Year: 2011).*
Brown, Brian D. et al, "Endogenous microRNA regulation suppresses transgene expression in hematopoietic lineages and enables stable gene transfer", Nature Medicine, 12:5, pp. 585-591 (2006).
Callum, Parr J.C. et al, "MicroRNA-302 switch to identity and eliminate undifferentiated human pluripotent stem cells.", Scientific Reports, vol. 6, pp. 1-14 (2016).
Endo, Kei et al., "A versatile cis-acting inverter module for syngthetic translation switches", Nature Communications; 4:2393, 9 pages (2013).
European Search Report corresponding to European Application No. 15764434.5, dated Aug. 17, 2017, 12 pages.
Kato, Yoshio et al., "Real-time functional imaging for monitoring miR-133 during myogenic differentiation", International Journal of Biochemistry and Cell Biology, 41:11, pp. 2225-2231 (2009).
Miki, Kenji et al., "Efficient detection and purification of cells by synthetic microRNA switches", Regenerative Medicine, p. 188 (2015).
Miki, Kenji et al., "Efficient detection and purification of cell populations using synthetic microRNA switches.", Cell Stem Cell, 16:6, pp. 699-711 (2015).
Kato Y et al. Poster. Constructon of translational regulating system using artificial RNA switches and giant liposomes. Journal of Japanese Biochemical Society. 4P-1322: 2007.
International Search Report, PCT/JP2015/058466, dated Jun. 23, 2015.
Synnergren J et al. Expression of microRNAs and their target mRNAs in human stem cell-derived cardiomyocyte clusters and in heart tissue. Physiol Genomics. 2011; 43(10): 581-594.

(Continued)

Primary Examiner — Brian Whiteman
(74) Attorney, Agent, or Firm — Myers Bigel, P.A.

(57) ABSTRACT

An object of the present invention is to provide a novel method for sorting cardiomyocytes. Another object of the present invention is to provide a method for producing high-purity cardiomyocytes and a kit used therefor. The present invention provides a method for sorting cardiomyocytes, comprising a step of introducing miRNA-responsive mRNA into a cell group, wherein the miRNA-responsive mRNA consists of a sequence comprising the following (i) and (ii):
(i) a nucleic acid specifically recognized by miRNA specifically expressed in cardiomyocytes, and
(ii) a nucleic acid corresponding to the coding region of a gene, wherein translation of (ii) the nucleic acid corresponding to the coding region of a gene into protein is regulated by the nucleic acid sequence in (i) above, thereby achieving the aforementioned objects.

29 Claims, 11 Drawing Sheets
Specification includes a Sequence Listing.

(56) References Cited

OTHER PUBLICATIONS

Babiarz JE et al. Determination of the human cardiomyocyte mRNA and miRNA differentiation network by fine-scale profiling. Stem Cells and Development. 2012; 21(11): 1956-1965.

Yan P et al. Cyclosporin—A potently induces highly cardiogenic progenitors from embryonic stem cells. Biochemical and Biophysical Research Communications. 2009; 379: 115-120.

Rust W et al. Cardiomyocyte enrichment from human embryonic stem cell cultures by selection of ALCAM surface expression. Regen Med. 2009; 4(2): 225-237.

Honda M et al. N-cadherin is a useful marker for the progenitor of cardiomyocytes differentiated from mouse ES cells in serum-free condition. Biochemical and Biophysical Research Communications. 2006; 351: 877-882.

Japanese Office Action corresponding to Japanese Patent Application No. 2016-508823, Machine Translation dated Jan. 25, 2019.

* cited by examiner

SEQUENCE LISTING

<160> NUMBER OF SEQ ID NOS: 108

<210> SEQ ID NO 1
<211> LENGTH: 22
<212> TYPE: RNA
<213> ORGANISM: Homo sapiens

<400> SEQUENCE: 1
uggaauguaa agaaguaugu au                    22

<210> SEQ ID NO 2
<211> LENGTH: 22
<212> TYPE: RNA
<213> ORGANISM: Homo sapiens

<400> SEQUENCE: 2
aguucuucag uggcaagcuu ua                    22

-continued

```
<210> SEQ ID NO 3
<211> LENGTH: 22
<212> TYPE: RNA
<213> ORGANISM: Homo sapiens

<400> SEQUENCE: 3
uuuggucccc uucaaccagc ug                                                  22

<210> SEQ ID NO 4
<211> LENGTH: 22
<212> TYPE: RNA
<213> ORGANISM: Homo sapiens

<400> SEQUENCE: 4
uuuggucccc uucaaccagc ua                                                  22

<210> SEQ ID NO 5
<211> LENGTH: 21
<212> TYPE: RNA
<213> ORGANISM: Homo sapiens

<400> SEQUENCE: 5
ugagaugaag cacuguagcu c                                                   21

<210> SEQ ID NO 6
<211> LENGTH: 22
<212> TYPE: RNA
<213> ORGANISM: Homo sapiens

<400> SEQUENCE: 6
ggauuccugg aaauacuguu cu                                                  22

<210> SEQ ID NO 7
<211> LENGTH: 22
<212> TYPE: RNA
<213> ORGANISM: Homo sapiens

<400> SEQUENCE: 7
auaagacgag caaaaagcuu gu                                                  22

<210> SEQ ID NO 8
<211> LENGTH: 22
<212> TYPE: RNA
<213> ORGANISM: Homo sapiens

<400> SEQUENCE: 8
caaccuggag gacuccaugc ug                                                  22

<210> SEQ ID NO 9
<211> LENGTH: 20
<212> TYPE: RNA
<213> ORGANISM: Homo sapiens

<400> SEQUENCE: 9
ccauggaucu ccaggugggu                                                     20

<210> SEQ ID NO 10
<211> LENGTH: 21
<212> TYPE: RNA
<213> ORGANISM: Homo sapiens

<400> SEQUENCE: 10
uuaagacuug cagugauguu u                                                   21
```

```
<210> SEQ ID NO 11
<211> LENGTH: 22
<212> TYPE: RNA
<213> ORGANISM: Homo sapiens

<400> SEQUENCE: 11
cuuggcaccu agcaagcacu ca                                              22

<210> SEQ ID NO 12
<211> LENGTH: 22
<212> TYPE: RNA
<213> ORGANISM: Homo sapiens

<400> SEQUENCE: 12
aggugcucca ggcuggcuca ca                                              22

<210> SEQ ID NO 13
<211> LENGTH: 20
<212> TYPE: RNA
<213> ORGANISM: Homo sapiens

<400> SEQUENCE: 13
cccugagacc cuaaccuuaa                                                 20

<210> SEQ ID NO 14
<211> LENGTH: 22
<212> TYPE: RNA
<213> ORGANISM: Homo sapiens

<400> SEQUENCE: 14
ugagguagga gguuguauag uu                                              22

<210> SEQ ID NO 15
<211> LENGTH: 22
<212> TYPE: RNA
<213> ORGANISM: Artificial
<220> FEATURE:
<223> OTHER INFORMATION: target hsa-miR-1

<400> SEQUENCE: 15
auacauacuu cuuuacauuc ca                                              22

<210> SEQ ID NO 16
<211> LENGTH: 22
<212> TYPE: RNA
<213> ORGANISM: Artificial
<220> FEATURE:
<223> OTHER INFORMATION: target hsa-miR-22-5p

<400> SEQUENCE: 16
uaaagcuugc cacugaagaa cu                                              22

<210> SEQ ID NO 17
<211> LENGTH: 22
<212> TYPE: RNA
<213> ORGANISM: Artificial
<220> FEATURE:
<223> OTHER INFORMATION: target hsa-miR-133a

<400> SEQUENCE: 17
cagcugguug aagggaccaa aa                                              22

<210> SEQ ID NO 18
```

```
<211> LENGTH: 22
<212> TYPE: RNA
<213> ORGANISM: Artificial
<220> FEATURE:
<223> OTHER INFORMATION: target hsa-miR-133b

<400> SEQUENCE: 18
uagcugguug aagggggacca aa                                              22

<210> SEQ ID NO 19
<211> LENGTH: 21
<212> TYPE: RNA
<213> ORGANISM: Artificial
<220> FEATURE:
<223> OTHER INFORMATION: target hsa-miR-143-3p

<400> SEQUENCE: 19
gagcuacagu gcuucaucuc a                                                21

<210> SEQ ID NO 20
<211> LENGTH: 22
<212> TYPE: RNA
<213> ORGANISM: Artificial
<220> FEATURE:
<223> OTHER INFORMATION: target hsa-miR-145-3p

<400> SEQUENCE: 20
agaacaguau uuccaggaau cc                                               22

<210> SEQ ID NO 21
<211> LENGTH: 22
<212> TYPE: RNA
<213> ORGANISM: Artificial
<220> FEATURE:
<223> OTHER INFORMATION: target hsa-miR-208a

<400> SEQUENCE: 21
acaagcuuuu ugcucgucuu au                                               22

<210> SEQ ID NO 22
<211> LENGTH: 22
<212> TYPE: RNA
<213> ORGANISM: Artificial
<220> FEATURE:
<223> OTHER INFORMATION: target hsa-miR-490-3p

<400> SEQUENCE: 22
cagcauggag uccuccaggu ug                                               22

<210> SEQ ID NO 23
<211> LENGTH: 20
<212> TYPE: RNA
<213> ORGANISM: Artificial
<220> FEATURE:
<223> OTHER INFORMATION: target hsa-miR-490-5p

<400> SEQUENCE: 23
acccaccugg agauccaugg                                                  20

<210> SEQ ID NO 24
<211> LENGTH: 21
<212> TYPE: RNA
<213> ORGANISM: Artificial
<220> FEATURE:
<223> OTHER INFORMATION: target hsa-miR-499a-5p

<400> SEQUENCE: 24
```
aaacaucacu gcaagucuua a        21

<210> SEQ ID NO 25
<211> LENGTH: 22
<212> TYPE: RNA
<213> ORGANISM: Artificial
<220> FEATURE:
<223> OTHER INFORMATION: target hsa-miR-1271-5p

<400> SEQUENCE: 25
ugagugcuug cuaggugcca ag        22

<210> SEQ ID NO 26
<211> LENGTH: 22
<212> TYPE: RNA
<213> ORGANISM: Artificial
<220> FEATURE:
<223> OTHER INFORMATION: target hsa-miR-3907

<400> SEQUENCE: 26
ugugagccag ccuggagcac cu        22

<210> SEQ ID NO 27
<211> LENGTH: 20
<212> TYPE: RNA
<213> ORGANISM: Artificial
<220> FEATURE:
<223> OTHER INFORMATION: target hsa-miR-4324

<400> SEQUENCE: 27
uuaagguuag ggucucaggg        20

<210> SEQ ID NO 28
<211> LENGTH: 22
<212> TYPE: RNA
<213> ORGANISM: Artificial
<220> FEATURE:
<223> OTHER INFORMATION: target hsa-let-7e-5p

<400> SEQUENCE: 28
aacuauacaa ccuccuaccu ca        22

<210> SEQ ID NO 29
<211> LENGTH: 65
<212> TYPE: RNA
<213> ORGANISM: Artificial
<220> FEATURE:
<223> OTHER INFORMATION: 5'UTR hsa-miR-1

<400> SEQUENCE: 29
gguuccgcga ucgcggaucc auacauacuu cuuuacauuc caagaucaca ccggucgcca        60
ccaug        65

<210> SEQ ID NO 30
<211> LENGTH: 65
<212> TYPE: RNA
<213> ORGANISM: Artificial
<220> FEATURE:
<223> OTHER INFORMATION: 5'UTR hsa-miR-22-5p

<400> SEQUENCE: 30
gguuccgcga ucgcggaucc uaaagcuugc cacugaagaa cuagaucaca ccggucgcca        60
ccaug        65

```
<210> SEQ ID NO 31
<211> LENGTH: 65
<212> TYPE: RNA
<213> ORGANISM: Artificial
<220> FEATURE:
<223> OTHER INFORMATION: 5'UTR hsa-miR-133a

<400> SEQUENCE: 31
gguuccgcga ucgcggaucc cagcugguug aagggggacca aaagaucaca ccggucgcca    60
ccaug                                                                65

<210> SEQ ID NO 32
<211> LENGTH: 65
<212> TYPE: RNA
<213> ORGANISM: Artificial
<220> FEATURE:
<223> OTHER INFORMATION: 5'UTR hsa-miR-133b

<400> SEQUENCE: 32
gguuccgcga ucgcggaucc uagcugguug aaggggacca aaagaucaca ccggucgcca     60
ccaug                                                                65

<210> SEQ ID NO 33
<211> LENGTH: 65
<212> TYPE: RNA
<213> ORGANISM: Artificial
<220> FEATURE:
<223> OTHER INFORMATION: 5'UTR hsa-miR-143-3p

<400> SEQUENCE: 33
gguuccgcga ucgcggaucc gagcuacagu gcuucaucuc aagaucaaca ccggucgcca     60
ccaug                                                                65

<210> SEQ ID NO 34
<211> LENGTH: 65
<212> TYPE: RNA
<213> ORGANISM: Artificial
<220> FEATURE:
<223> OTHER INFORMATION: 5'UTR hsa-miR-145-3p

<400> SEQUENCE: 34
gguuccgcga ucgcggaucc agaacaguau uuccaggaau ccagaucaca ccggucgcca     60
ccaug                                                                65

<210> SEQ ID NO 35
<211> LENGTH: 65
<212> TYPE: RNA
<213> ORGANISM: Artificial
<220> FEATURE:
<223> OTHER INFORMATION: 5'UTR hsa-miR-208a

<400> SEQUENCE: 35
gguuccgcga ucgcggaucc acaagcuuuu ugcucgucuu auagaucaca ccggucgcca     60
ccaug                                                                65

<210> SEQ ID NO 36
<211> LENGTH: 65
<212> TYPE: RNA
<213> ORGANISM: Artificial
<220> FEATURE:
<223> OTHER INFORMATION: 5'UTR hsa-miR-490-3p

<400> SEQUENCE: 36
```

```
gguuccgcga ucgcggaucc acccaccugg agauccaugg agaucaaaca ccggucgcca    60
ccaug                                                                65

<210> SEQ ID NO 37
<211> LENGTH: 65
<212> TYPE: RNA
<213> ORGANISM: Artificial
<220> FEATURE:
<223> OTHER INFORMATION: 5'UTR hsa-miR-490-5p

<400> SEQUENCE: 37 gguccgcga ucgcggaucc cagcauggag uccuccaggu ugagaucaca ccggucgcca     60
ccaug                                                                65

<210> SEQ ID NO 38
<211> LENGTH: 65
<212> TYPE: RNA
<213> ORGANISM: Artificial
<220> FEATURE:
<223> OTHER INFORMATION: 5'UTR hsa-miR-499a-5p

<400> SEQUENCE: 38 gguccgcga ucgcggaucc aaacaucacu gcaagucuua aagaucaaca ccggucgcca     60
ccaug                                                                65

<210> SEQ ID NO 39
<211> LENGTH: 65
<212> TYPE: RNA
<213> ORGANISM: Artificial
<220> FEATURE:
<223> OTHER INFORMATION: 5'UTR hsa-miR-1271-5p

<400> SEQUENCE: 39 gguccgcga ucgcggaucc ugagugcuug cuaggugcca agagaucaca ccggucgcca     60
ccaug                                                                65

<210> SEQ ID NO 40
<211> LENGTH: 65
<212> TYPE: RNA
<213> ORGANISM: Artificial
<220> FEATURE:
<223> OTHER INFORMATION: 5'UTR hsa-miR-3907

<400> SEQUENCE: 40 gguccgcga ucgcggaucc ugugagccag ccuggagcac cuagaucaca ccggucgcca     60
ccaug                                                                65

<210> SEQ ID NO 41
<211> LENGTH: 65
<212> TYPE: RNA
<213> ORGANISM: Artificial
<220> FEATURE:
<223> OTHER INFORMATION: 5'UTR hsa-miR-4324

<400> SEQUENCE: 41 gguccgcga ucgcggaucc uuaagguuag ggucucaggg agaucaaaca ccggucgcca     60
ccaug                                                                65

<210> SEQ ID NO 42
<211> LENGTH: 65
<212> TYPE: RNA
```

<213> ORGANISM: Artificial
<220> FEATURE:
<223> OTHER INFORMATION: 5'UTR hsa-let-7e-5p

<400> SEQUENCE: 42

```
gguuccgcga ucgcggaucc aacuauacaa ccuccuaccu caagaucaca ccggucgcca    60
ccaug                                                                65
```

<210> SEQ ID NO 43
<211> LENGTH: 539
<212> TYPE: RNA
<213> ORGANISM: Artificial
<220> FEATURE:
<223> OTHER INFORMATION: 3'UTR

<400> SEQUENCE: 43

```
ccugugaugc agaagaaaac acucggcugg gaggccuuca ccgagacgcu guaccccgcu    60
gacggcggcc uggaaggcag aaacgacaug gcccugaagc ucgugggcgg gagccaucug   120
aucgcaaaca ucaagaccac auauagaucc aagaaacccg cuaagaaccu caagaugccu   180
ggcgucuacu augugg acua cagacuggaa agaaucaagg aggccaacaa cgagaccuac   240
gucgagcagc acgagguggc aguggccaga uacugcgacc ucccuagcaa acuggggcac   300
agaucucaua ugcaucucga gugauagucu agaccuucug cggggcuugc cuucuggcca   360
ugcccuucuu cucccccuug caccuguacc ucuuggucuu ugaauaaagc cugaguagga   420
aaaaaaaaaa aaaaaaaaaa aaaaaaaaaa aaaaaaaaaa aaaaaaaaaa aaaaaaaaaa   480
aaaaaaaaaa aaaaaaaaaa aaaaaaaaaa aaaaaaaaaa aaaaaaaaaa aaaaaaaaa    539
```

<210> SEQ ID NO 44
<211> LENGTH: 997
<212> TYPE: RNA
<213> ORGANISM: Artificial
<220> FEATURE:
<223> OTHER INFORMATION: mRNA_hsa-miR-1

<400> SEQUENCE: 44

```
gguuccuuaa ucgcggaucc auacauacuu cuuuacauuc caagaucaca ccggucgcca    60
ccaugggauc cagcgagcug auuaaggaga acaugcacau gaagcuguac auggagggca   120
ccguggacaa ccaucacuuc aagugcacau ccgagggcga aggcaagccc uacgagggca   180
cccagaccau gagaaucaag guggucgagg gcggcccucu cccuucgcc uucgacaucc   240 uggcuacuag cuuccucuac ggcagcaaga ccuucaucaa ccacacccag ggcaucccg   300 acuucuucaa gcagccuuc ccugagggcu ucacauggga gagagucacc acaucgaag   360 acggggggcgu gcugaccgcu acccaggaca ccagccucca ggacggcugc cucaucuaca   420
acgucaagau cagagggguug aacuucacau ccaacggccc ugugaugcag aagaaaacac   480
ucggcuggga ggccuucacc gagacgcugu accccgcuga cggcggccug gaaggcagaa   540
acgacauggc ccugaagcuc gugggcggga gccaucugau cgcaaacauc aagaccacau   600
auagauccaa gaaacccgcu aagaaccuca agaugccugg cgucuacuau guggacuaca   660
gacuggaaag aaucaaggag gccaacaacg agaccuacgu cgagcagcac gagguggcag   720
uggccagaua cugcgaccuc ccuagcaaac uggggcacag aucucauaug caucucgagu   780
gauagucuag accuucugcg gggcuugccu ucuggccaug cccuucucu cucccuugca    840 ccuguaccuc uuggucuuug aauaaagccu gaguaggaaa aaaaaaaaa aaaaaaaaa     900 aaaaaaaaaa aaaaaaaaaa aaaaaaaaaa aaaaaaaaaa aaaaaaaaaa aaaaaaaaaa   960
```

```
aaaaaaaaaa aaaaaaaaaa aaaaaaaaaa aaaaaaa                                    997
```

<210> SEQ ID NO 45
<211> LENGTH: 997
<212> TYPE: RNA
<213> ORGANISM: Artificial
<220> FEATURE:
<223> OTHER INFORMATION: mRNA_hsa-miR-22-5p

<400> SEQUENCE: 45

```
gguuccuuaa ucgcggaucc uaaagcuugc cacugaagaa cuagaucaca ccggucgcca      60
ccaugggauc cagcgagcug auuaaggaga acaugcacau gaagcuguac auggagggca     120
ccguggacaa ccaucacuuc aagugcacau ccgagggcga aggcaagccc uacgagggca     180
cccagaccau gagaaucaag guggucgagg cggcccucu ccccuucgcc uucgacaucc      240
uggcuacuag cuuccucuac ggcagcaaga ccuucaucaa ccacacccag ggcaucccg      300
acuucuucaa gcagaccuuc ccugagggcu ucacauggga gagagucacc acauacgaag     360
acgggggcgu gcugaccgcu acccaggaca ccagccucca ggacggcugc cucaucuaca     420
acgucaagau cagaggggug aacuucacau ccaacggccc ugugaugcag aagaaaacac     480
ucggcuggga ggccuucacc gagacgcugu accccgcuga cggcggccug aaggcagaa      540
acgacauggc ccugaagcuc gugggcggga gccaucugau cgcaaacauc aagaccacau     600
auagauccaa gaaacccgcu aagaaccuca agaugccugg cgucuacuau guggacuaca     660
gacuggaaag aaucaaggag gccaacaacg agaccuacgu cgagcagcac gagguggcag     720
uggccagaua cugcgaccuc ccuagcaaac uggggcacag aucucauaug caucucgagu     780
gauagucuag accuucugcg gggcuugccu ucuggccaug cccuucuucu cucccuugca     840
ccuguaccuc uuggucuuug aauaaagccu gaguaggaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaa                              997
```

<210> SEQ ID NO 46
<211> LENGTH: 997
<212> TYPE: RNA
<213> ORGANISM: Artificial
<220> FEATURE:
<223> OTHER INFORMATION: mRNA_hsa-miR-133a-3p

<400> SEQUENCE: 46

```
gguuccuuaa ucgcggaucc cagcugguug aaggggacca aaagaucaca ccggucgcca      60
ccaugggauc cagcgagcug auuaaggaga acaugcacau gaagcuguac auggagggca     120
ccguggacaa ccaucacuuc aagugcacau ccgagggcga aggcaagccc uacgagggca     180
cccagaccau gagaaucaag guggucgagg cggcccucu ccccuucgcc uucgacaucc      240
uggcuacuag cuuccucuac ggcagcaaga ccuucaucaa ccacacccag ggcaucccg      300
acuucuucaa gcagaccuuc ccugagggcu ucacauggga gagagucacc acauacgaag     360
acgggggcgu gcugaccgcu acccaggaca ccagccucca ggacggcugc cucaucuaca     420
acgucaagau cagaggggug aacuucacau ccaacggccc ugugaugcag aagaaaacac     480
ucggcuggga ggccuucacc gagacgcugu accccgcuga cggcggccug aaggcagaa      540
acgacauggc ccugaagcuc gugggcggga gccaucugau cgcaaacauc aagaccacau     600
auagauccaa gaaacccgcu aagaaccuca agaugccugg cgucuacuau guggacuaca     660
```

```
gacuggaaag aaucaaggag gccaacaacg agaccuacgu cgagcagcac gagguggcag    720
uggccagaua cugcgaccuc ccuagcaaac uggggcacag aucucauaug caucucgagu    780
gauagucuag accuucugcg gggcuugccu ucuggccaug cccuucuucu cucccuugca    840
ccuguaccuc uuggucuuug aauaaagccu gaguaggaaa aaaaaaaaa aaaaaaaaa      900 aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaa                             997

<210> SEQ ID NO 47
<211> LENGTH: 997
<212> TYPE: RNA
<213> ORGANISM: Artificial
<220> FEATURE:
<223> OTHER INFORMATION: mRNA_hsa-miR-133b

<400> SEQUENCE: 47
gguuccuuaa ucgcggaucc uagcugguug aaggggacca aaagaucaca ccggucgcca    60
ccaugggauc cagcgagcug auuaaggaga acaugcacau gaagcuguac auggagggca    120
ccguggacaa ccaucacuuc aagugcacau ccgagggcga aggcaagccc uacgagggca    180
cccagaccau gagaaucaag guggucgagg gcggcccucu ccccuucgcc uucgacaucc    240
uggcuacuag cuuccucuac ggcagcaaga ccuucaucaa ccacacccag ggcaucccg    300 acuucuucaa gcaguccuuc ccugagggcu ucacauggga gagagucacc acauacgaag    360 acggggggcgu gcugaccgcu acccaggaca ccagccucca ggacggcugc cucaucuaca    420
acgucaagau cagagggggug aacuucacau ccaacggccc ugugaugcag aagaaaacac    480
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau guggacuaca    660
gacuggaaag aaucaaggag gccaacaacg agaccuacgu cgagcagcac gagguggcag    720
uggccagaua cugcgaccuc ccuagcaaac uggggcacag aucucauaug caucucgagu    780
gauagucuag accuucugcg gggcuugccu ucuggccaug cccuucuucu cucccuugca    840
ccuguaccuc uuggucuuug aauaaagccu gaguaggaaa aaaaaaaaa aaaaaaaaa      900 aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaa                             997

<210> SEQ ID NO 48
<211> LENGTH: 997
<212> TYPE: RNA
<213> ORGANISM: Artificial
<220> FEATURE:
<223> OTHER INFORMATION: mRNA_hsa-miR-143-3p

<400> SEQUENCE: 48
gguuccuuaa ucgcggaucc gagcuacagu gcuucaucuc aagaucaaca ccggucgcca    60
ccaugggauc cagcgagcug auuaaggaga acaugcacau gaagcuguac auggagggca    120
ccguggacaa ccaucacuuc aagugcacau ccgagggcga aggcaagccc uacgagggca    180
cccagaccau gagaaucaag guggucgagg gcggcccucu ccccuucgcc uucgacaucc    240
uggcuacuag cuuccucuac ggcagcaaga ccuucaucaa ccacacccag ggcaucccg    300 acuucuucaa gcaguccuuc ccugagggcu ucacauggga gagagucacc acauacgaag    360 acggggggcgu gcugaccgcu acccaggaca ccagccucca ggacggcugc cucaucuaca    420
```

```
acgucaagau cagaggggug aacuucacau ccaacggccc ugugaugcag aagaaaacac    480
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau gggacuaca    660 gacuggaaag aaucaaggag gccaacaacg agaccuacgu cgagcagcac gagguggcag    720
uggccagaua cugcgaccuc ccuagcaaac uggggcacag aucucauaug caucucgagu    780
gauagucuag accuucugcg gggcuugccu ucuggccaug cccuucuucu cucccuugca    840
ccuguaccuc uuggucuuug aauaaagccu gaguaggaaa aaaaaaaaa aaaaaaaaa     900 aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaa                             997
```

<210> SEQ ID NO 49
<211> LENGTH: 997
<212> TYPE: RNA
<213> ORGANISM: Artificial
<220> FEATURE:
<223> OTHER INFORMATION: mRNA_hsa-miR-145-3p

<400> SEQUENCE: 49

```
gguuccuuaa ucgcggaucc agaacaguau uuccaggaau ccagaucaca ccggucgcca     60
ccaugggauc cagcgagcug auuaaggaga acaugcacau gaagcuguac auggagggca    120
ccguggacaa ccaucacuuc aagugcacau ccgagggcga aggcaagccc uacgagggca    180
cccagaccau gagaaucaag guggucgagg gcggccucu ccccuucgcc uucgacaucc    240
uggcuacuag cuuccucuac ggcagcaaga ccuucaucaa ccacacccag ggcauccccg    300
acuucuucaa gcaguccuuc ccugagggcu ucacauggga gagagucacc acauacgaag    360 acggggcgu gcugaccgcu acccaggaca ccagccucca ggacggcugc cucaucuaca    420
acgucaagau cagaggggug aacuucacau ccaacggccc ugugaugcag aagaaaacac    480
ucggcuggga ggccuucacc gagacgcugu accccgcuga cggcggccug gaaggcagaa    540
acgacauggc ccugaagcuc gugggcggga gccaucugau cgcaaacauc aagaccacau    600
auagauccaa gaaacccgcu aagaaccuca agaugccugg cgucuacuau gggacuaca    660 gacuggaaag aaucaaggag gccaacaacg agaccuacgu cgagcagcac gagguggcag    720
uggccagaua cugcgaccuc ccuagcaaac uggggcacag aucucauaug caucucgagu    780
gauagucuag accuucugcg gggcuugccu ucuggccaug cccuucuucu cucccuugca    840
ccuguaccuc uuggucuuug aauaaagccu gaguaggaaa aaaaaaaaa aaaaaaaaa     900 aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaa                             997
```

<210> SEQ ID NO 50
<211> LENGTH: 997
<212> TYPE: RNA
<213> ORGANISM: Artificial
<220> FEATURE:
<223> OTHER INFORMATION: mRNA_hsa-miR-208a-3p

<400> SEQUENCE: 50

```
gguuccuuaa ucgcggaucc acaagcuuuu ugcucgucuu auagaucaca ccggucgcca     60
ccaugggauc cagcgagcug auuaaggaga acaugcacau gaagcuguac auggagggca    120
```

| | |
|---|---|
| ccguggacaa ccaucacuuc aagugcacau ccgagggcga aggcaagccc uacgagggca | 180 |
| cccagaccau gagaaucaag guggucgagg gcggcccucu ccccuucgcc uucgacaucc | 240 |
| uggcuacuag cuuccucuac ggcagcaaga ccuucaucaa ccacacccag ggcauccccg | 300 |
| acuucuucaa gcagccuuc ccugagggcu ucacauggga gagagucacc acaucgaag | 360 |
| acggggcgu gcugaccgcu acccaggaca ccagccucca ggacggcugc cucaucuaca | 420 |
| acgucaagau cagaggggug aacuucacau ccaacggccc ugugaugcag aagaaaacac | 480 |
| ucggcuggga ggccuucacc gagacgcugu accccgcuga cggcggccug gaaggcagaa | 540 |
| acgacauggc ccugaagcuc guggcggga gccaucugau cgcaaacauc aagaccacau | 600 |
| auagauccaa gaaacccgcu aagaaccuca agaugccugg cgucuacuau gggacuaca | 660 |
| gacuggaaag aaucaaggag gccaacaacg agaccuacgu cgagcagcac gagguggcag | 720 |
| uggccagaua cugcgaccuc ccuagcaaac ugggggcacag aucucauaug caucucgagu | 780 |
| gauagcuag accuucugcg gggcuugccu ucuggccaug cccuucuucu cucccuugca | 840 |
| ccuguaccuc uuggucuuug aauaaagccu gaguaggaaa aaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaa | 997 |

<210> SEQ ID NO 51
<211> LENGTH: 997
<212> TYPE: RNA
<213> ORGANISM: Artificial
<220> FEATURE:
<223> OTHER INFORMATION: mRNA_hsa-miR-490-3p

<400> SEQUENCE: 51

| | |
|---|---|
| gguuccuuaa ucgcggaucc cagcauggag uccuccaggu ugagaucaca ccggucgcca | 60 |
| ccaugggauc cagcgagcug auuaaggaga acaugcacau gaagcuguac auggagggca | 120 |
| ccguggacaa ccaucacuuc aagugcacau ccgagggcga aggcaagccc uacgagggca | 180 |
| cccagaccau gagaaucaag guggucgagg gcggcccucu ccccuucgcc uucgacaucc | 240 |
| uggcuacuag cuuccucuac ggcagcaaga ccuucaucaa ccacacccag ggcauccccg | 300 |
| acuucuucaa gcagccuuc ccugagggcu ucacauggga gagagucacc acaucgaag | 360 |
| acggggcgu gcugaccgcu acccaggaca ccagccucca ggacggcugc cucaucuaca | 420 |
| acgucaagau cagaggggug aacuucacau ccaacggccc ugugaugcag aagaaaacac | 480 |
| ucggcuggga ggccuucacc gagacgcugu accccgcuga cggcggccug gaaggcagaa | 540 |
| acgacauggc ccugaagcuc guggcggga gccaucugau cgcaaacauc aagaccacau | 600 |
| auagauccaa gaaacccgcu aagaaccuca agaugccugg cgucuacuau gggacuaca | 660 |
| gacuggaaag aaucaaggag gccaacaacg agaccuacgu cgagcagcac gagguggcag | 720 |
| uggccagaua cugcgaccuc ccuagcaaac ugggggcacag aucucauaug caucucgagu | 780 |
| gauagcuag accuucugcg gggcuugccu ucuggccaug cccuucuucu cucccuugca | 840 |
| ccuguaccuc uuggucuuug aauaaagccu gaguaggaaa aaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaa | 997 |

<210> SEQ ID NO 52
<211> LENGTH: 997
<212> TYPE: RNA
<213> ORGANISM: Artificial

```
<220> FEATURE:
<223> OTHER INFORMATION: mRNA_hsa-miR-490-5p

<400> SEQUENCE: 52
gguuccuuaa ucgcggaucc acccaccugg agauccaugg agaucaaaca ccggucgcca      60
ccaugggauc cagcgagcug auuaaggaga acaugcacau gaagcuguac auggagggca     120
ccguggacaa ccaucacuuc aagugcacau ccgagggcga aggcaagccc uacgagggca     180
cccagaccau gagaaucaag guggucgagg gcggcccucu ccccuucgcc uucgacaucc     240
uggcuacuag cuuccucuac ggcagcaaga ccuucaucaa ccacacccag ggcauccccg     300
acuucuucaa gcagccuuuc ccugagggcu ucacauggga gagagucacc acauacgaag     360
acgggggcgu gcugaccgcu acccaggaca ccagccucca ggacggcugc cucaucuaca     420
acgucaagau cagaggggug aacuucacau ccaacggccc ugugaugcag aagaaaacac     480
ucggcuggga ggccuucacc gagacgcugu accccgcuga cggcggccug gaaggcagaa     540
acgacauggc ccugaagcuc gugggcggga gccaucugau cgcaaacauc aagaccacau     600
auagauccaa gaaacccgcu aagaaccuca agaugccugg cgucuacuau guggacuaca     660
gacuggaaag aaucaaggag gccaacaacg agaccuacgu cgagcagcac gagguggcag     720
uggccagaua cugcgaccuc ccuagcaaac uggggcacag aucucauaug caucucgagu     780
gauagucuag accuucugcg gggcuugccu ucuggcaug cccuucuucu cucccuugca     840
ccuguaccuc uuggucuuug aauaaagccu gaguaggaaa aaaaaaaaa aaaaaaaaa      900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaa                              997

<210> SEQ ID NO 53
<211> LENGTH: 997
<212> TYPE: RNA
<213> ORGANISM: Artificial
<220> FEATURE:
<223> OTHER INFORMATION: mRNA_hsa-miR-499a-5p

<400> SEQUENCE: 53
gguuccuuaa ucgcggaucc aaacaucacu gcaagucuua aagaucaaca ccggucgcca      60
ccaugggauc cagcgagcug auuaaggaga acaugcacau gaagcuguac auggagggca     120
ccguggacaa ccaucacuuc aagugcacau ccgagggcga aggcaagccc uacgagggca     180
cccagaccau gagaaucaag guggucgagg gcggcccucu ccccuucgcc uucgacaucc     240
uggcuacuag cuuccucuac ggcagcaaga ccuucaucaa ccacacccag ggcauccccg     300
acuucuucaa gcagccuuuc ccugagggcu ucacauggga gagagucacc acauacgaag     360
acgggggcgu gcugaccgcu acccaggaca ccagccucca ggacggcugc cucaucuaca     420
acgucaagau cagaggggug aacuucacau ccaacggccc ugugaugcag aagaaaacac     480
ucggcuggga ggccuucacc gagacgcugu accccgcuga cggcggccug gaaggcagaa     540
acgacauggc ccugaagcuc gugggcggga gccaucugau cgcaaacauc aagaccacau     600
auagauccaa gaaacccgcu aagaaccuca agaugccugg cgucuacuau guggacuaca     660
gacuggaaag aaucaaggag gccaacaacg agaccuacgu cgagcagcac gagguggcag     720
uggccagaua cugcgaccuc ccuagcaaac uggggcacag aucucauaug caucucgagu     780
gauagucuag accuucugcg gggcuugccu ucuggcaug cccuucuucu cucccuugca     840
ccuguaccuc uuggucuuug aauaaagccu gaguaggaaa aaaaaaaaa aaaaaaaaa      900
```

```
aaaaaaaaaa aaaaaaaaa aaaaaaaaaa aaaaaaaaaa aaaaaaaaaa aaaaaaaaaa      960
aaaaaaaaaa aaaaaaaaaa aaaaaaaaaa aaaaaaa                               997

<210> SEQ ID NO 54
<211> LENGTH: 997
<212> TYPE: RNA
<213> ORGANISM: Artificial
<220> FEATURE:
<223> OTHER INFORMATION: mRNA_hsa-miR-1271-5p

<400> SEQUENCE: 54
gguuccuuaa ucgcggaucc ugagugcuug cuaggugcca agagaucaca ccggucgcca       60
ccaugggauc cagcgagcug auuaaggaga acaugcacau gaagcuguac auggagggca      120
ccguggacaa ccaucacuuc aagugcacau ccgagggcga aggcaagccc uacgagggca      180
cccagaccau gagaaucaag guggucgagg gcggcccucu cccuucgcc uucgacaucc       240 uggcuacuag cuuccucuac ggcagcaaga ccuucaucaa ccacacccag ggcauccccg      300
acuucuucaa gcaguccuuc ccugagggcu ucacauggga gagagucacc acaucgaag       360 acggggcgu gcugaccgcu acccaggaca ccagccucca ggacggcugc cucaucuaca       420
acgucaagau cagaggggug aacuucacau ccaacgcccc ugugaugcag aagaaaacac      480
ucggcuggga ggccuucacc gagacgcugu acccgcuga cggcggccug gaaggcagaa       540
acgacauggc ccugaagcuc gugggcggga gccaucugau cgcaaacauc aagaccacau      600
auagauccaa gaaacccgcu aagaaccuca agaugccugg cgucuacuau guggacuaca      660
gacuggaaag aaucaaggag gccaacaacg agaccuacgu cgagcagcac gagguggcag      720
uggccagaua cugcgaccuc ccuagcaaac uggggcacag aucucauaug caucucgagu      780
gauagucuag accuucugcg gggcuugccu ucuggccaug cccuucuucu cucccuugca      840
ccuguaccuc uuggucuuug aauaaagccu gaguaggaaa aaaaaaaaa aaaaaaaaa        900 aaaaaaaaaa aaaaaaaa aaaaaaaaaa aaaaaaaaaa aaaaaaaaaa aaaaaaaaaa       960
aaaaaaaaaa aaaaaaaaa aaaaaaaaaa aaaaaaa                               997

<210> SEQ ID NO 55
<211> LENGTH: 997
<212> TYPE: RNA
<213> ORGANISM: Artificial
<220> FEATURE:
<223> OTHER INFORMATION: mRNA_hsa-miR-3907

<400> SEQUENCE: 55
gguuccuuaa ucgcggaucc ugugagccag ccuggagcac cuagaucaca ccggucgcca       60
ccaugggauc cagcgagcug auuaaggaga acaugcacau gaagcuguac auggagggca      120
ccguggacaa ccaucacuuc aagugcacau ccgagggcga aggcaagccc uacgagggca      180
cccagaccau gagaaucaag guggucgagg gcggcccucu cccuucgcc uucgacaucc       240 uggcuacuag cuuccucuac ggcagcaaga ccuucaucaa ccacacccag ggcauccccg      300
acuucuucaa gcaguccuuc ccugagggcu ucacauggga gagagucacc acaucgaag       360 acggggcgu gcugaccgcu acccaggaca ccagccucca ggacggcugc cucaucuaca       420
acgucaagau cagaggggug aacuucacau ccaacgcccc ugugaugcag aagaaaacac      480
ucggcuggga ggccuucacc gagacgcugu acccgcuga cggcggccug gaaggcagaa       540
acgacauggc ccugaagcuc gugggcggga gccaucugau cgcaaacauc aagaccacau      600
auagauccaa gaaacccgcu aagaaccuca agaugccugg cgucuacuau guggacuaca      660
```

| gacuggaaag aaucaaggag gccaacaacg agaccuacgu cgagcagcac gagguggcag | 720 |
| uggccagaua cugcgaccuc ccuagcaaac uggggcacag aucucauaug caucucgagu | 780 |
| gauagucuag accuucugcg gggcuugccu ucuggccaug cccuucuucu cucccuugca | 840 |
| ccuguaccuc uuggucuuug aauaaagccu gaguaggaaa aaaaaaaaaa aaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaa | 997 |

<210> SEQ ID NO 56
<211> LENGTH: 997
<212> TYPE: RNA
<213> ORGANISM: Artificial
<220> FEATURE:
<223> OTHER INFORMATION: mRNA_hsa-miR-4324

<400> SEQUENCE: 56

| gguuccuuaa ucgcggaucc uuaagguuag ggucucaggg agaucaaaca ccggucgcca | 60 |
| ccaugggauc cagcgagcug auuaaggaga acaugcacau gaagcuguac auggagggca | 120 |
| ccguggacaa ccaucacuuc aagugcacau ccgagggcga aggcaagccc uacgagggca | 180 |
| cccagaccau gagaaucaag guggucgagg gcggcccucu ccccuucgcc uucgacaucc | 240 |
| uggcuacuag cuuccucuac ggcagcaaga ccuucaucaa ccacacccag ggcauccccg | 300 |
| acuucuucaa gcaguccuuc ccugagggcu ucacauggga gagagucacc acauacgaag | 360 |
| acggggggcgu gcugaccgcu acccaggaca ccagccucca ggacggcugc ucaucuaca | 420 |
| acgucaagau cagaggggug aacuucacau ccaacggccc ugugaugcag aagaaaacac | 480 |
| ucggcugggg ggccuucacc gagacgcugu accccgcuga cggcggccug gaaggcagaa | 540 |
| acgacauggc ccugaagcuc gugggcggga gccaucugau cgcaaacauc aagaccacau | 600 |
| auagauccaa gaaacccgcu aagaaccuca agaugccugg cgucuacaau gggacuaca | 660 |
| gacuggaaag aaucaaggag gccaacaacg agaccuacgu cgagcagcac gagguggcag | 720 |
| uggccagaua cugcgaccuc ccuagcaaac uggggcacag aucucauaug caucucgagu | 780 |
| gauagucuag accuucugcg gggcuugccu ucuggccaug cccuucuucu cucccuugca | 840 |
| ccuguaccuc uuggucuuug aauaaagccu gaguaggaaa aaaaaaaaaa aaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaa | 997 |

<210> SEQ ID NO 57
<211> LENGTH: 997
<212> TYPE: RNA
<213> ORGANISM: Artificial
<220> FEATURE:
<223> OTHER INFORMATION: mRNA_hsa-let-7e-5p

<400> SEQUENCE: 57

| gguuccuuaa ucgcggaucc aacuauacaa ccuccuaccu caagaucaca ccggucgcca | 60 |
| ccaugggauc cagcgagcug auuaaggaga acaugcacau gaagcuguac auggagggca | 120 |
| ccguggacaa ccaucacuuc aagugcacau ccgagggcga aggcaagccc uacgagggca | 180 |
| cccagaccau gagaaucaag guggucgagg gcggcccucu ccccuucgcc uucgacaucc | 240 |
| uggcuacuag cuuccucuac ggcagcaaga ccuucaucaa ccacacccag ggcauccccg | 300 |
| acuucuucaa gcaguccuuc ccugagggcu ucacauggga gagagucacc acauacgaag | 360 |

| | |
|---|---|
| acggggcgu gcugaccgcu acccaggaca ccagccucca ggacggcugc cucaucuaca | 420 |
| acgucaagau cagaggggug aacuucacau ccaacggccc ugugaugcag aagaaaacac | 480 |
| ucggcuggga ggccuucacc gagacgcugu accccgcuga cggcggccug gaaggcagaa | 540 |
| acgacauggc ccugaagcuc gugggcggga gccaucugau cgcaaacauc aagaccacau | 600 |
| auagauccaa gaaacccgcu aagaaccuca agaugccugg cgucuacuau guggacuaca | 660 |
| gacuggaaag aaucaaggag gccaacaacg agaccuacgu cgagcagcac gagguggcag | 720 |
| uggccagaua cugcgaccuc ccuagcaaac uggggcacag aucucauaug caucucgagu | 780 |
| gauagucuag accuucugcg gggcuugccu ucuggccaug cccucuucu cucccuugca | 840 |
| ccuguaccuc uuggucuuug aauaaagccu gaguaggaaa aaaaaaaaa aaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaa aaaaaaaaa aaaaaaa | 997 |

<210> SEQ ID NO 58
<211> LENGTH: 872
<212> TYPE: RNA
<213> ORGANISM: Artificial
<220> FEATURE:
<223> OTHER INFORMATION: mRNA_miR-1-HsBimEL

<400> SEQUENCE: 58

| | |
|---|---|
| gguuccuuaa ucgcggaucc auacauacuu cuuuacauuc caagaucaca ccggucgcca | 60 |
| ccauggcaaa gcaaccuucu gauguaaguu cugagugugu ccgagaaggu agacaauugc | 120 |
| agccugcgga gaggccuccc cagcucagac cuggggcccc uaccucccua cagacagagc | 180 |
| cacaagguaa uccugaaggc aaucacggag gugaagggga cagcugcccc cacggcagcc | 240 |
| cucagggccc gcuggcccca ccugccagcc cuggccuuuu gcuaccaga uccccgcuuu | 300 |
| ucaucuuuau gagaagaucc ucccugcugu cucgauccuc cagggguauu uucucuuug | 360 |
| acacagacag gagcccagca cccaugaguu ugacaaauc aacacaaacc caaguccuc | 420 |
| cuugccaggc cuucaaccac uaucucagug caauggcuuc caugaggcag gcugaaccug | 480 |
| cagauaugcg cccagagaua uggaucgccc aagaguugcg gcuaucggga gacgaguuua | 540 |
| acgcuuacua ugcaaggagg guauuuuuga auaauuacca gcagccgaa gaccaccccac | 600 |
| gaauugguau cuuacgacug uuacguuaca uuguccgccu gguguggaga augcauugau | 660 |
| ucuagaccuu cugcggggcu ugccuucugg ccaugcccuu cuucucccc uugcaccugu | 720 |
| accucuuggu cuuugaauaa agccugagua ggaaaaaaaa aaaaaaaaaa aaaaaaaaaa | 780 |
| aaaaaaaaaa aaaaaaaaaa aaaaaaaaaa aaaaaaaaaa aaaaaaaaaa aaaaaaaaaa | 840 |
| aaaaaaaaaa aaaaaaaaaa aaaaaaaaaa aa | 872 |

<210> SEQ ID NO 59
<211> LENGTH: 1030
<212> TYPE: RNA
<213> ORGANISM: Artificial
<220> FEATURE:
<223> OTHER INFORMATION: mRNA_miR-208a-3p_hdKeima-Red

<400> SEQUENCE: 59

| | |
|---|---|
| gguuccuuaa ucgcggaucc acaagcuuuu ugcucgucuu auagaucaca ccggucgcca | 60 |
| ccauggugag cgugaucgcc aagcagauga ccuacaaggu guacauguc ggcaccguga | 120 |
| acggccacua cuucgaggug gagggcgacg gcaagggcaa gcccuacgag ggcgagcaga | 180 |
| ccgugaagcu gaccgugacc aagggcggcc cccugccuu cgccuggac auccugucc | 240 |

```
cccuguucca guacggcagc auccccuuca ccaaguaccc cgaggacauc cccgacuacg    300
ugaagcagag cuuccccgag ggcuacaccu gggagaggac caugaacuuc gaggacggcg    360
ccgugugcac cgugagcaac gacuccagca uccagggcaa cugcuucauc uacaacguga    420
agaucagcgg caccaacuuc cccccaacg gccccgugau gcagaagaag acccagggcu     480
gggagcccag caccgagagg cuguucgcca gggacggaau gcugaucggc aacgacuaca    540
uggcccugaa gcuggagggc ggcggccacu accugugcga guucaagucc accuacaagg    600
ccaagaagcc cgugaggaug cccggcuacc acuacaucga caggaagcug gacgugacca    660
gccacaacag ggacuacacc uccguggagc agugcgagau cgccaucgcc aggcacagcc    720
ugcugggcgg cagcagcggc ggauccggug augaagucga aggaguggaa gaaguagcua    780
agaagaagag uaaaaaggaa aaggauaaaa aguaauaguc uagaccuucu gcggggcuug    840
ccuucuggcc augcccuucu ucucucccuu gcaccuguac cucuuggucu uugaauaaag    900
ccugaguagg aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa                                                          1030

<210> SEQ ID NO 60
<211> LENGTH: 1030
<212> TYPE: RNA
<213> ORGANISM: Artificial
<220> FEATURE:
<223> OTHER INFORMATION: mRNA_miR-499a-5p_hdKeima-Red

<400> SEQUENCE: 60
gguuccuuaa ucgcggaucc aaacaucacu gcaagucuua aagaucaaca ccggucgcca     60
ccauggugag cgugaucgcc aagcagauga ccuacaaggu guacaugucc ggcaccguga    120
acggccacua cuucgaggug gagggcgacg gcaagggcaa gcccuacgag ggcgagcaga    180
ccgugaagcu gaccgugacc aagggcggcc ccugcccuu cgccgggac auccugu ccc     240 cccuguucca guacggcagc auccccuuca ccaaguaccc cgaggacauc cccgacuacg    300
ugaagcagag cuuccccgag ggcuacaccu gggagaggac caugaacuuc gaggacggcg    360
ccgugugcac cgugagcaac gacuccagca uccagggcaa cugcuucauc uacaacguga    420
agaucagcgg caccaacuuc cccccaacg gccccgugau gcagaagaag acccagggcu     480
gggagcccag caccgagagg cuguucgcca gggacggaau gcugaucggc aacgacuaca    540
uggcccugaa gcuggagggc ggcggccacu accugugcga guucaagucc accuacaagg    600
ccaagaagcc cgugaggaug cccggcuacc acuacaucga caggaagcug gacgugacca    660
gccacaacag ggacuacacc uccguggagc agugcgagau cgccaucgcc aggcacagcc    720
ugcugggcgg cagcagcggc ggauccggug augaagucga aggaguggaa gaaguagcua    780
agaagaagag uaaaaaggaa aaggauaaaa aguaauaguc uagaccuucu gcggggcuug    840
ccuucuggcc augcccuucu ucucucccuu gcaccuguac cucuuggucu uugaauaaag    900
ccugaguagg aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa                                                          1030

<210> SEQ ID NO 61
<211> LENGTH: 992
<212> TYPE: RNA
```

```
<213> ORGANISM: Artificial
<220> FEATURE:
<223> OTHER INFORMATION: mRNA_tagBFP

<400> SEQUENCE: 61
gggcgaauua agagagaaaa gaagaguaag aagaaauaua agacaccggu cgccaccaug        60
ggauccagcg agcugauuaa ggagaacaug cacaugaagc uguacaugga gggcaccgug       120
gacaaccauc acuucaagug cacauccgag ggcgaaggca agcccuacga gggcacccag       180
accaugagaa ucaagguggu cgagggcggc ccucucccu ucgccuucga cauccuggcu        240
acuagcuucc ucuacggcag caagaccuuc aucaaccaca cccagggcau ccccgacuuc       300
uucaagcagu ccuucccuga gggcuucaca ugggagagag ucaccacaua cgaagacggg       360
ggcgugcuga ccgcuaccca ggacaccagc uccaggacg gcugccucau cuacaacguc        420
aagaucagag gggugaacuu cacauccaac ggcccuguga ugcagaagaa acacucggc        480
ugggaggccu ucaccgagac gcuguacccc gcugacggcg gccuggaagg cagaaacgac       540
auggcccuga agcucugggg cgggagccau cugaucgcaa acaucaagac cacauauaga       600
uccaagaaac ccgcuaagaa ccucaagaug ccuggcgucu acauguggga cuacagacug       660
gaaagaauca aggaggccaa caacgagacc uacgucgagc agcacgaggu ggcagguggcc      720
agauacugcg accucccuag caaacugggg cacagaucuc auaugcaucu cgagugauag       780
ucuagaccuu cugcggggcu ugccuucugg ccaugcccuu cuucucuccc uugcaccugu       840
accucuuggu cuugaauaa agccgaguga ggaaaaaaaa aaaaaaaaaa aaaaaaaaaa        900
aaaaaaaaaa aaaaaaaaaa aaaaaaaaaa aaaaaaaaaa aaaaaaaaaa aaaaaaaaaa       960
aaaaaaaaaa aaaaaaaaaa aaaaaaaaaa aa                                    992

<210> SEQ ID NO 62
<211> LENGTH: 1019
<212> TYPE: RNA
<213> ORGANISM: Artificial
<220> FEATURE:
<223> OTHER INFORMATION: mRNA_EGFP

<400> SEQUENCE: 62
gggcgaauua agagagaaaa gaagaguaag aagaaauaua agacaccggu cgccaccaug        60
ggauccguga gcaagggcga ggagcuguuc accggggugg ugcccauccu ggucgagcug       120
gacggcgacg uaaacggcca caaguucagc gugccggcg agggcgaggg cgaugccacc        180
uacggcaagc ugacccugaa guucaucugc accaccggca agcugcccgu gcccuggccc       240
acccucguga ccacccugac cuacggcgug cagugcuuca gccgcuaccc cgaccacaug       300
aagcagcacg acuucuucaa guccgccaug cccgaaggcu acguccagga gcgcaccauc       360
uucuucaagg acgacggcaa cuacaagacc cgcgccgagg ugaaguucga gggcgacacc       420
cuggugaacc gcaucgagcu gaagggcauc gacuucaagg aggacggcaa cauccugggg       480
cacaagcugg aguacaacua caacagccac aacgucuaua ucauggccga caagcagaag       540
aacggcauca aggugaacuu caagauccgc cacaacaucg aggacggcag cgugcagcuc       600
gccgaccacu accagcagaa cacccccauc ggcgacggcc ccgugcugcu gcccgacaac       660
cacuaccuga gcacccaguc cgcccugagc aaagacccca acgagaagcg cgaucacaug       720
guccugcugg aguucgugac cgccgccggg aucacucucg gcauggacga gcuguacaag       780
agaucucaua ugcaucucga gugauagucu agaccuucga cggggcuugc cuucggcca        840
ugcccuucuu cucucccuug caccuguacc ucuuggucuu ugaauaaagc cugaguagga       900
```

| | |
|---|---|
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaaa | 1019 |

<210> SEQ ID NO 63
<211> LENGTH: 668
<212> TYPE: RNA
<213> ORGANISM: Artificial
<220> FEATURE:
<223> OTHER INFORMATION: mRNA_Blastcidin

<400> SEQUENCE: 63

| | |
|---|---|
| gggcgaauua agagagaaaa gaagaguaag aagaaauaua agacaccggu cgccaccaug | 60 |
| gccaagccuu ugucucaaga agaauccacc cucauugaaa gagcaacggc uacaaucaac | 120 |
| agcauccccca ucucugaaga cuacagcguc gccagcgcag cucucucuag cgacggccgc | 180 |
| aucuucacug gugucaaugu auaucauuuu acuggggac cuugugcaga acucguggug | 240 |
| cugggcacug cugcugcugc ggcagcuggc aacugacuu guaucgucgc gaucggaaau | 300 |
| gagaacaggg gcaucuugag ccccugcgga cggugccgac aggugcuucu cgaucugcau | 360 |
| ccugggauca aagccauagu gaaggacagu gauggacagc cgacggcagu gggauucgu | 420 |
| gaauugcugc ccucugguua uguguggag ggcuaaucua gaccuucugc ggggcuugcc | 480 |
| uucuggccau gcccuucuuc ucucccuugc accuguaccu cuuggucuuu gaauaaagcc | 540 |
| ugaguaggaa aaaaaaaaaa aaaaaaaaaa aaaaaaaaaa aaaaaaaaaa aaaaaaaaaa | 600 |
| aaaaaaaaaa aaaaaaaaaa aaaaaaaaaa aaaaaaaaaa aaaaaaaaaa aaaaaaaaaa | 660 |
| aaaaaaaa | 668 |

<210> SEQ ID NO 64
<211> LENGTH: 869
<212> TYPE: RNA
<213> ORGANISM: Artificial
<220> FEATURE:
<223> OTHER INFORMATION: mRNA_Puromycin

<400> SEQUENCE: 64

| | |
|---|---|
| gggcgaauua agagagaaaa gaagaguaag aagaaauaua agacaccggu cgccaccaug | 60 |
| accgaguaca agcccacggu gcgccucgcc acccgcgacg acgucccccg ggccguacgc | 120 |
| accccucgccg ccgcguucgc cgacuacccc gccacgcgcc acaccgucga uccggaccgc | 180 |
| cacaucgagc gggucaccga gcugcaagaa cucuuccuca cgcgcgucgg gcucgacauc | 240 |
| ggcaaggugu gggucgcgga cgacggcgcc ggguggcgg ucuggaccac gccggagagc | 300 |
| gucgaagcgg gggcgguguu cgccgagauc ggcccgcgca uggccgaguu gagcgguucc | 360 |
| cggcuggccg cgcagcaaca gauggaaggc cuccuggcgc cgcaccggcc caaggagccc | 420 |
| gcguggauucc uggccaccgu cggcgucucg cccgaccacc agggcaaggg ucugggcagc | 480 |
| gccgucgugc uccccggagu ggaggcggcc gagcgcgccg gggugcccgc cuuccuggag | 540 |
| accuccgcgc cccgcaaccu cccucuuuac gagcggcucg gcuucaccgu caccgccgac | 600 |
| gucgaggugc ccgaaggacc gcgcaccugg ugcaugaccc gcaagcccgg ugccugaucu | 660 |
| agaccuucug cggggcuugc cuucggcca ugcccuucuu cucucccuug caccuguaccu | 720 |
| ucuuggucuuu ugaauaaagc cugaguagga aaaaaaaaaa aaaaaaaaaa aaaaaaaaaa | 780 |
| aaaaaaaaaa aaaaaaaaaa aaaaaaaaaa aaaaaaaaaa aaaaaaaaaa aaaaaaaaaa | 840 |
| aaaaaaaaaa aaaaaaaaaa aaaaaaaaa | 869 |

<210> SEQ ID NO 65
<211> LENGTH: 22
<212> TYPE: RNA
<213> ORGANISM: Homo sapiens

<400> SEQUENCE: 65
auaagacgaa caaaagguuu gu                                          22

<210> SEQ ID NO 66
<211> LENGTH: 22
<212> TYPE: RNA
<213> ORGANISM: Artificial
<220> FEATURE:
<223> OTHER INFORMATION: target hsa-miR-208b

<400> SEQUENCE: 66
acaaaccuuu uguucgucuu au                                          22

<210> SEQ ID NO 67
<211> LENGTH: 65
<212> TYPE: RNA
<213> ORGANISM: Artificial
<220> FEATURE:
<223> OTHER INFORMATION: 5'UTR hsa-miR-208b

<400> SEQUENCE: 67
gguuccgcga ucgcggaucc acaaaccuuu uguucgucuu auagaucaca ccggucgcca    60
ccaug                                                               65

<210> SEQ ID NO 68
<211> LENGTH: 997
<212> TYPE: RNA
<213> ORGANISM: Artificial
<220> FEATURE:
<223> OTHER INFORMATION: mRNA_hsa-miR-208b

<400> SEQUENCE: 68
gguuccuuaa ucgcggaucc acaaaccuuu uguucgucuu auagaucaca ccggucgcca    60
ccaugggauc cagcgagcug auuaaggaga acaugcacau gaagcuguac auggagggca   120
ccguggacaa ccaucacuuc aagugcacau ccgagggcga aggcaagccc uacgagggca   180
cccagaccau gagaaucaag guggucgagg gcggcccucu ccccuucgcc uucgacaucc   240
uggcuacuag cuuccucuac ggcagcaaga ccuucaucaa ccacacccag ggcaucccccg  300 acuucuucaa gcagucccuuc ccugagggcu ucacauggga gagagucacc acauacgaag   360 acggggggcgu gcugaccgcu acccaggaca ccagccucca ggacggcugc cucaucuaca   420
acgucaagau cagaggggug aacuucacau ccaacggccc ugugaugcag aagaaaacac   480
ucggcuggga ggccuucacc gagacgcugu accccgcuga cggcggccug gaaggcagaa   540
acgacauggc ccugaagcuc guggggcggga gccaucugau cgcaaacauc aagaccacau   600
auagauccaa gaaacccgcu aagaaccuca agaugccugg cgucuacuau guggacuaca   660
gacuggaaag aaucaaggag gccaacaacg agaccuacgu cgagcagcac gagguggcag   720
uggccagaua cugcgaccuc ccuagcaaac uggggcacag aucucauaug caucucgagu   780
gauagucuag accuucugcg gggcuugccu ucuggccaug cccuucuucu cucccuugca   840
ccuguaccuc uuggcuuuug aauaaagccu gaguaggaaa aaaaaaaaa aaaaaaaaa    900 aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aaaaaaa                           997

<210> SEQ ID NO 69
<211> LENGTH: 29
<212> TYPE: DNA
<213> ORGANISM: Artificial
<220> FEATURE:
<223> OTHER INFORMATION: tagBFP fwd

<400> SEQUENCE: 69
caccggtcgc caccatggga tccagcgag                              29

<210> SEQ ID NO 70
<211> LENGTH: 35
<212> TYPE: DNA
<213> ORGANISM: Artificial
<220> FEATURE:
<223> OTHER INFORMATION: TAPEGFP_IVTfwd

<400> SEQUENCE: 70
caccggtcgc caccatggga tccgtgagca agggc                       35

<210> SEQ ID NO 71
<211> LENGTH: 45
<212> TYPE: DNA
<213> ORGANISM: Artificial
<220> FEATURE:
<223> OTHER INFORMATION: TAP_IVTrev

<400> SEQUENCE: 71
gccccgcaga aggtctagac tatcactcga gatgcatatg agatc            45

<210> SEQ ID NO 72
<211> LENGTH: 35
<212> TYPE: DNA
<213> ORGANISM: Artificial
<220> FEATURE:
<223> OTHER INFORMATION: hdKeimaRed_IVTfwd

<400> SEQUENCE: 72
caccggtcgc caccatggtg agcgtgatcg ccaag                       35

<210> SEQ ID NO 73
<211> LENGTH: 56
<212> TYPE: DNA
<213> ORGANISM: Artificial
<220> FEATURE:
<223> OTHER INFORMATION: pNP-hdKeima-Red rev

<400> SEQUENCE: 73
gccccgcaga aggtctagac tattactttt tatcctttc cttttactc ttcttc   56

<210> SEQ ID NO 74
<211> LENGTH: 31
<212> TYPE: DNA
<213> ORGANISM: Artificial
<220> FEATURE:
<223> OTHER INFORMATION: TAP_T7_G3C fwd primer

<400> SEQUENCE: 74
cagtgaattg taatacgact cactataggg c                           31

<210> SEQ ID NO 75
<211> LENGTH: 37
<212> TYPE: DNA
<213> ORGANISM: Artificial
<220> FEATURE:

<223> OTHER INFORMATION: Rev5UTR primer

<400> SEQUENCE: 75
catggtggcg accggtgtct tatatttctt cttactc         37

<210> SEQ ID NO 76
<211> LENGTH: 87
<212> TYPE: DNA
<213> ORGANISM: Artificial
<220> FEATURE:
<223> OTHER INFORMATION: IVT_5prime_UTR

<400> SEQUENCE: 76
cagtgaattg taatacgact cactataggg cgaattaaga gagaaaagaa gagtaagaag         60
aaatataaga caccggtcgc caccatg         87

<210> SEQ ID NO 77
<211> LENGTH: 19
<212> TYPE: DNA
<213> ORGANISM: Artificial
<220> FEATURE:
<223> OTHER INFORMATION: Fwd3UTR primer

<400> SEQUENCE: 77
tctagacctt ctgcggggc         19

<210> SEQ ID NO 78
<211> LENGTH: 48
<212> TYPE: DNA
<213> ORGANISM: Artificial
<220> FEATURE:
<223> OTHER INFORMATION: Rev3UTR2T20

<400> SEQUENCE: 78
tttttttttt tttttttttt cctactcagg ctttattcaa agaccaag         48

<210> SEQ ID NO 79
<211> LENGTH: 139
<212> TYPE: DNA
<213> ORGANISM: Artificial
<220> FEATURE:
<223> OTHER INFORMATION: 3UTR120A rev primer

<400> SEQUENCE: 79
tttttttttt tttttttttt tttttttttt tttttttttt tttttttttt tttttttttt         60
tttttttttt tttttttttt tttttttttt tttttttttt tttttttttt tttttttttt         120
cctactcagg ctttattca         139

<210> SEQ ID NO 80
<211> LENGTH: 92
<212> TYPE: DNA
<213> ORGANISM: Artificial
<220> FEATURE:
<223> OTHER INFORMATION: IVT_3prime_UTR

<400> SEQUENCE: 80
tctagacctt ctgcggggct tgccttctgg ccatgccctt cttctctccc ttgcacctgt         60
acctcttggt ctttgaataa agcctgagta gg         92

<210> SEQ ID NO 81
<211> LENGTH: 39
<212> TYPE: DNA
<213> ORGANISM: Artificial

-continued

```
<220> FEATURE:
<223> OTHER INFORMATION: GCT7pro_5UTR2

<400> SEQUENCE: 81
gctaatacga ctcactatag gttccttaat cgcggatcc                              39

<210> SEQ ID NO 82
<211> LENGTH: 31
<212> TYPE: DNA
<213> ORGANISM: Artificial
<220> FEATURE:
<223> OTHER INFORMATION: ORF Blastcidin Fwd

<400> SEQUENCE: 82
caccggtcgc caccatggcc aagcctttgt c                                      31

<210> SEQ ID NO 83
<211> LENGTH: 42
<212> TYPE: DNA
<213> ORGANISM: Artificial
<220> FEATURE:
<223> OTHER INFORMATION: ORF Blastcidin Rev

<400> SEQUENCE: 83
gccccgcaga aggtctagat tagccctccc acacataacc ag                          42

<210> SEQ ID NO 84
<211> LENGTH: 35
<212> TYPE: DNA
<213> ORGANISM: Artificial
<220> FEATURE:
<223> OTHER INFORMATION: ORF Puromycin Fwd

<400> SEQUENCE: 84
caccggtcgc caccatgacc gagtacaagc ccacg                                  35

<210> SEQ ID NO 85
<211> LENGTH: 36
<212> TYPE: DNA
<213> ORGANISM: Artificial
<220> FEATURE:
<223> OTHER INFORMATION: ORF Puromycin Rev

<400> SEQUENCE: 85
gccccgcaga aggtctagat caggcaccgg gcttgc                                 36

<210> SEQ ID NO 86
<211> LENGTH: 17
<212> TYPE: DNA
<213> ORGANISM: Artificial
<220> FEATURE:
<223> OTHER INFORMATION: Clontech_IVTfwd

<400> SEQUENCE: 86
caccggtcgc caccatg                                                      17

<210> SEQ ID NO 87
<211> LENGTH: 41
<212> TYPE: DNA
<213> ORGANISM: Artificial
<220> FEATURE:
<223> OTHER INFORMATION: BimEL_IVTrev

<400> SEQUENCE: 87
gccccgcaga aggtctagaa tcaatgcatt ctccacacca g                           41
```

-continued

<210> SEQ ID NO 88
<211> LENGTH: 36
<212> TYPE: DNA
<213> ORGANISM: Artificial
<220> FEATURE:
<223> OTHER INFORMATION: TagBFP_Tfwd

<400> SEQUENCE: 88
gccaccatgg gatccagcga gctgattaag gagaac                                  36

<210> SEQ ID NO 89
<211> LENGTH: 28
<212> TYPE: DNA
<213> ORGANISM: Artificial
<220> FEATURE:
<223> OTHER INFORMATION: TagBFP_Trev

<400> SEQUENCE: 89
actcgagatc tgtgccccag tttgctag                                           28

<210> SEQ ID NO 90
<211> LENGTH: 60
<212> TYPE: DNA
<213> ORGANISM: Artificial
<220> FEATURE:
<223> OTHER INFORMATION: pGEMTAP_MCS_Rev

<400> SEQUENCE: 90
gggatcccat ggtgtcgacc tgcagcatat gagctcctga attcgcccta tagtgagtcg        60

<210> SEQ ID NO 91
<211> LENGTH: 63
<212> TYPE: DNA
<213> ORGANISM: Artificial
<220> FEATURE:
<223> OTHER INFORMATION: pGEMTAP_MCS_Fwd

<400> SEQUENCE: 91
gggagatctc atatgcatct cgagtgatag tctagacaag cttgagtatt ctatagtgtc        60
acc                                                                      63

<210> SEQ ID NO 92
<211> LENGTH: 30
<212> TYPE: DNA
<213> ORGANISM: Artificial
<220> FEATURE:
<223> OTHER INFORMATION: YF128_EXFP_Tfwd

<400> SEQUENCE: 92
gaaccatggg atccgtgagc aagggcgagg                                         30

<210> SEQ ID NO 93
<211> LENGTH: 29
<212> TYPE: DNA
<213> ORGANISM: Artificial
<220> FEATURE:
<223> OTHER INFORMATION: YF129_EXFP_Trev

<400> SEQUENCE: 93
tatgagatct cttgtacagc tcgtccatg                                          29

<210> SEQ ID NO 94
<211> LENGTH: 77
<212> TYPE: DNA
<213> ORGANISM: Artificial

```
<220> FEATURE:
<223> OTHER INFORMATION: 5UTRtemp_let-7e-5p

<400> SEQUENCE: 94
cgactcacta taggttccgc gatcgcggat ccaactatac aacctcctac ctcaagatca    60
caccggtcgc caccatg                                                   77

<210> SEQ ID NO 95
<211> LENGTH: 77
<212> TYPE: DNA
<213> ORGANISM: Artificial
<220> FEATURE:
<223> OTHER INFORMATION: 5UTRtemp_T1

<400> SEQUENCE: 95
cgactcacta taggttccgc gatcgcggat ccatacatac ttctttacat tccaagatca    60
caccggtcgc caccatg                                                   77

<210> SEQ ID NO 96
<211> LENGTH: 77
<212> TYPE: DNA
<213> ORGANISM: Artificial
<220> FEATURE:
<223> OTHER INFORMATION: 5UTRtemp_T22-5p

<400> SEQUENCE: 96
cgactcacta taggttccgc gatcgcggat cctaaagctt gccactgaag aactagatca    60
caccggtcgc caccatg                                                   77

<210> SEQ ID NO 97
<211> LENGTH: 77
<212> TYPE: DNA
<213> ORGANISM: Artificial
<220> FEATURE:
<223> OTHER INFORMATION: 5UTRtemp_T133a-3p

<400> SEQUENCE: 97
cgactcacta taggttccgc gatcgcggat cccagctggt tgaaggggac caaaagatca    60
caccggtcgc caccatg                                                   77

<210> SEQ ID NO 98
<211> LENGTH: 77
<212> TYPE: DNA
<213> ORGANISM: Artificial
<220> FEATURE:
<223> OTHER INFORMATION: 5UTRtemp_T133b

<400> SEQUENCE: 98
cgactcacta taggttccgc gatcgcggat cctagctggt tgaaggggac caaaagatca    60
caccggtcgc caccatg                                                   77

<210> SEQ ID NO 99
<211> LENGTH: 77
<212> TYPE: DNA
<213> ORGANISM: Artificial
<220> FEATURE:
<223> OTHER INFORMATION: 5UTRtemp_T143-3p

<400> SEQUENCE: 99
cgactcacta taggttccgc gatcgcggat ccgagctaca gtgcttcatc tcaagatcaa    60
caccggtcgc caccatg                                                   77
```

```
<210> SEQ ID NO 100
<211> LENGTH: 77
<212> TYPE: DNA
<213> ORGANISM: Artificial
<220> FEATURE:
<223> OTHER INFORMATION: 5UTRtemp_T145-3p

<400> SEQUENCE: 100
cgactcacta taggttccgc gatcgcggat ccagaacagt atttccagga atccagatca    60
caccggtcgc caccatg                                                   77

<210> SEQ ID NO 101
<211> LENGTH: 77
<212> TYPE: DNA
<213> ORGANISM: Artificial
<220> FEATURE:
<223> OTHER INFORMATION: 5UTRtemp_T208a-3p

<400> SEQUENCE: 101
cgactcacta taggttccgc gatcgcggat ccacaagctt tttgctcgtc ttatagatca    60
caccggtcgc caccatg                                                   77

<210> SEQ ID NO 102
<211> LENGTH: 77
<212> TYPE: DNA
<213> ORGANISM: Artificial
<220> FEATURE:
<223> OTHER INFORMATION: 5UTRtemp_T490-5p

<400> SEQUENCE: 102
cgactcacta taggttccgc gatcgcggat ccacccacct ggagatccat ggagatcaaa    60
caccggtcgc caccatg                                                   77

<210> SEQ ID NO 103
<211> LENGTH: 77
<212> TYPE: DNA
<213> ORGANISM: Artificial
<220> FEATURE:
<223> OTHER INFORMATION: 5UTRtemp_T490-3p

<400> SEQUENCE: 103
cgactcacta taggttccgc gatcgcggat cccagcatgg agtcctccag gttgagatca    60
caccggtcgc caccatg                                                   77

<210> SEQ ID NO 104
<211> LENGTH: 77
<212> TYPE: DNA
<213> ORGANISM: Artificial
<220> FEATURE:
<223> OTHER INFORMATION: 5UTRtemp_T499a-5p

<400> SEQUENCE: 104
cgactcacta taggttccgc gatcgcggat ccaaacatca ctgcaagtct taaagatcaa    60
caccggtcgc caccatg                                                   77

<210> SEQ ID NO 105
<211> LENGTH: 77
<212> TYPE: DNA
<213> ORGANISM: Artificial
<220> FEATURE:
<223> OTHER INFORMATION: 5UTRtemp_T1271-5p

<400> SEQUENCE: 105
```

```
cgactcacta taggttccgc gatcgcggat cctgagtgct tgctaggtgc caagagatca      60
caccggtcgc caccatg                                                     77

<210> SEQ ID NO 106
<211> LENGTH: 77
<212> TYPE: DNA
<213> ORGANISM: Artificial
<220> FEATURE:
<223> OTHER INFORMATION: 5UTRtemp_T3907

<400> SEQUENCE: 106
cgactcacta taggttccgc gatcgcggat cctgtgagcc agcctggagc acctagatca      60
caccggtcgc caccatg                                                     77

<210> SEQ ID NO 107
<211> LENGTH: 77
<212> TYPE: DNA
<213> ORGANISM: Artificial
<220> FEATURE:
<223> OTHER INFORMATION: 5UTRtemp_T4324

<400> SEQUENCE: 107
cgactcacta taggttccgc gatcgcggat ccttaaggtt agggtctcag ggagatcaaa      60
caccggtcgc caccatg                                                     77

<210> SEQ ID NO 108
<211> LENGTH: 77
<212> TYPE: DNA
<213> ORGANISM: Artificial
<220> FEATURE:
<223> OTHER INFORMATION: 5UTRtemp_T208b

<400> SEQUENCE: 108
cgactcacta taggttccgc gatcgcggat ccacaaacct tttgttcgtc ttatagatca      60
caccggtcgc caccatg                                                     77
```

METHOD FOR SORTING CARDIOMYOCYTES

RELATED APPLICATIONS

This application is a 35 U. S. C § 371 national phase application of PCT Application PCT/JP2015/058466 filed Mar. 20, 2015, which claims priority to Japanese Application No. 2014-058926 filed Mar. 20, 2014, the disclosure of each of which is incorporated by reference in its entirety.

STATEMENT REGARDING ELECTRONIC FILING OF A SEQUENCE LISTING

A sequence Listing in ASCII text format, submitted under 37 C.F.R. § 1.821, entitled 5576-327_ST25.txt, 49,689 bytes in size, generated on Oct. 16, 2018, and filed via EFS-Web, is provided in lieu of a paper copy. This Sequence Listing is hereby incorporated by reference into the specification for its disclosures.

TECHNICAL FIELD

The present invention relates to a novel method for sorting cardiomyocytes. The present invention also relates to a method for producing highly purified cardiomyocytes and to a kit used therefor.

BACKGROUND ART

Cardiomyocytes lose the ability to divide at the time of birth, and regeneration thereof is difficult. Accordingly, in recent years, considerable attention has been paid to replacement therapies in which cardiomyocytes obtained by induction of differentiation of cells having pluripotency (Patent Literature 1), such as embryonic stem cells (ES cells) or induced pluripotent stem cells (iPS cells), are transplanted into cardiac tissues damaged by myocardial infarction, myocarditis, aging or the like. Many methods for inducing differentiation of such pluripotent stem cells into cardiomyocytes have been reported (Patent Literature 2, Patent Literature 3, Patent Literature 4, and Non Patent Literature 1). However, in order to use cardiomyocytes as cells to be transplanted, it is necessary to increase the purity of the cardiomyocytes by sorting or the like.

At present, many of the reported methods for sorting out cardiomyocytes are methods for sorting cardiomyocytes using a surface marker for cardiomyocytes or myocardial precursor cells (Non Patent Literature 2, Non Patent Literature 3, Patent Literature 4, and Patent Literature 5).

CITATION LIST

Patent Literature

[Patent Literature 1] International Publication No. WO 2007/069666
[Patent Literature 2] International Publication No. WO 2007/002136
[Patent Literature 3] International Publication No. WO 2009/118928
[Patent Literature 4] Japanese Patent Application Laid-Open No. 2010-158206
[Patent Literature 5] International Publication No. WO 2014/014119

Non Patent Literature

[Non Patent Literature 1] Yan P, et al, Biochem Biophys Res Commun. 379: 115-20 (2009)
[Non Patent Literature 2] Rust W, et al, Regen Med. 4, 225-37 (2009)
[Non Patent Literature 3] Honda M, et al, Biochem Biophys Res Commun. 29, 351, 877-82 (2006)

SUMMARY OF INVENTION

Technical Problem

Considering the aforementioned conventional techniques, in order to increase the degree of purity of cardiomyocytes, it has been desired to develop a novel sorting method from another viewpoint. That is to say, an object of the present invention is to provide a novel method for sorting out cardiomyocytes. Another object of the present invention is to provide a method for producing high-purity cardiomyocytes and kit used therefor.

Solution to Problem

As a result of intensive research conducted to achieve the aforementioned objects, the present inventors have discovered that cardiomyocytes can be purified to a high degree of purity by using miRNA-responsive mRNA. Specifically, induced and differentiated cells from pluripotent stem cells were classified into a cardiomyocyte group and a non-cardiomyocyte group, and the cells were then subjected to a miRNA microarray analysis. As a result, the inventors found that a plurality of miRNAs was specifically expressed in the cardiomyocytes. Hence, miRNA-responsive OFF switch mRNA corresponding to such miRNA was produced, and the mRNA was then introduced into cells used as sorting targets, followed by the sorting of the cardiomyocytes. As a result, the present inventors have succeeded in purifying the cardiomyocytes to an extremely high degree of purity. Moreover, the inventors have also discovered that, by using miRNA-responsive OFF switch mRNA in combination with drug resistance gene mRNA, cardiomyocytes can be purified to a high degree of purity, without a step of selecting out the cardiomyocytes according to FACS. The present invention has been completed based on these findings.

Specifically, the present invention provides the following matters.

(1) A method for sorting cardiomyocytes, comprising a step of introducing miRNA-responsive mRNA into a cell group, wherein
the miRNA-responsive mRNA consists of a sequence comprising the following (i) and (ii):
(i) a nucleic acid specifically recognized by miRNA specifically expressed in cardiomyocytes, and
(ii) a nucleic acid corresponding to the coding region of a gene, wherein translation of (ii) the nucleic acid corresponding to the coding region of a gene into protein is regulated by the nucleic acid sequence in (i) above.
(2) The method according to (1), wherein the miRNA-responsive mRNA is miRNA-responsive OFF switch mRNA.
(3) The method according to (1) or (2), wherein the nucleic acids (i) and (ii) are linked to each other in the direction from 5' to 3', in this order.
(4) The method according to any one of (1) to (3), wherein the miRNA specifically expressed in cardiomyocytes in (i) above is one or more miRNAs selected from the group consisting of miR-1, miR-208a, miR-208b and miR-499a-5p.
(5) The method according to any one of (1) to (4), wherein the gene in (ii) above is one or more genes selected from the group consisting of a gene encoding a fluorescent protein, an apoptosis-inducing gene and a suicide gene.

(6) The method according to (5), wherein the gene encoding a fluorescent protein is a gene encoding a blue fluorescent protein (BFP).

(7) The method according to (5), wherein the apoptosis-inducing gene is a gene encoding a Bim protein.

(8) The method according to any one of (1) to (7), further comprising a step of introducing mRNA consisting of a sequence comprising a nucleic acid corresponding to the coding region of a drug resistance gene into the cell group.

(9) The method according to (8), wherein the drug resistance gene is an antibiotic resistance gene.

(10) The method according to (9), wherein the antibiotic resistance gene is a puromycin resistance gene or a blasticidin resistance gene.

(11) The method according to any one of (1) to (10), wherein the cell group of the step (a) is constituted with cells induced to differentiate from pluripotent stem cells.

(12) A method for producing cardiomyocytes, comprising the following steps (a) and (b):
(a) a step of introducing miRNA-responsive mRNA into a cell group, and
(b) a step of sorting the cells based on the translation level of a protein from the mRNA of the step (a), wherein
the miRNA-responsive mRNA consists of a sequence comprising the following (i) and (ii):
(i) a nucleic acid specifically recognized by miRNA specifically expressed in cardiomyocytes, and
(ii) a nucleic acid corresponding to the coding region of a gene, wherein
highly purified cardiomyocytes can be obtained compared with a case in which the steps (a) and (b) are not carried out.

(13) The method according to (12), wherein the miRNA-responsive mRNA is miRNA-responsive OFF switch mRNA.

(14) The method according to (12) or (13), wherein the nucleic acids (i) and (ii) are linked to each other in the direction from 5' to 3', in this order.

(15) The method according to any one of (12) to (14), wherein the miRNA specifically expressed in cardiomyocytes in (i) above is one or more miRNAs selected from the group consisting of miR-1, miR-208a, miR-208b and miR-499a-5p.

(16) The method according to any one of (12) to (15), wherein the gene in (ii) above is a gene encoding a fluorescent protein.

(17) The method according to (16), wherein the gene encoding a fluorescent protein is a gene encoding BFP.

(18) The method according to any one of (12) to (17), wherein the cell group of the step (a) is constituted with induced and differentiated cells from pluripotent stem cells.

(19) A method for producing cardiomyocytes, comprising the following steps (a) and (b):
(a) a step of introducing miRNA-responsive mRNA and mRNA consisting of a sequence comprising a nucleic acid corresponding to the coding region of a drug resistance gene into a cell group, and
(b) a step of culturing the cell obtained in the step (a) in the presence of a drug corresponding to the drug resistance gene of the step (a), wherein
the miRNA-responsive mRNA consists of a sequence comprising the following (i) and (ii):
(i) a nucleic acid specifically recognized by miRNA specifically expressed in cardiomyocytes, and
(ii) a nucleic acid corresponding to the coding region of a gene, wherein high-purity cardiomyocytes can be obtained compared with a case in which the steps (a) and (b) are not carried out.

(20) The method according to (19), wherein the miRNA-responsive mRNA is miRNA-responsive OFF switch mRNA.

(21) The method according to (19) or (20), wherein the nucleic acids (i) and (ii) are linked to each other in the direction from 5' to 3', in this order.

(22) The method according to any one of (19) to (21), wherein the miRNA specifically expressed in cardiomyocytes in (i) above is one or more miRNAs selected from the group consisting of miR-1, miR-208a, miR-208b and miR-499a-5p.

(23) The method according to any one of (19) to (21), wherein the gene in (ii) above is an apoptosis-inducing gene and/or a suicide gene.

(24) The method according to (23), wherein the apoptosis-inducing gene is a gene encoding a Bim protein.

(25) The method according to any one of (19) to (24), wherein the drug resistance gene is an antibiotic resistance gene.

(26) The method according to (25), wherein the antibiotic resistance gene is a puromycin resistance gene or a blasticidin resistance gene.

(27) The method according to any one of (19) to (26), wherein the cell group of the step (a) is constituted with induced and differentiated cells from pluripotent stem cells.

(28) A kit for purifying cardiomyocytes, comprising miRNA-responsive mRNA, wherein the miRNA-responsive mRNA consists of a sequence comprising the following (i) and (ii):
(i) a nucleic acid specifically recognized by miRNA specifically expressed in cardiomyocytes, and
(ii) a nucleic acid corresponding to the coding region of a gene.

Advantageous Effects of Invention

According to the method of the present invention, it becomes possible to easily select out cardiomyocytes and to purify the cardiomyocytes to highly purified cardiomyocytes. Since mRNA introduced into a cell group by the method of the present invention is only transiently present in the cells, the mRNA is not incorporated into the genome, so that cardiomyocytes can be sorted safely. In addition, according to the method of the present invention, living cells can be sorted based on the expression level of miRNA that is in an active state in the cells, without immobilizing the cells. Moreover, by using purified cardiomyocytes that have been obtained by the method for producing cardiomyocytes of the present invention, it becomes possible to treat heart diseases such as heart failure, ischemic heart disease, myocardial infarction, cardiomyopathy, myocarditis, hypertrophic cardiomyopathy, dilated phase of hypertrophic cardiomyopathy, and dilated cardiomyopathy.

DESCRIPTION OF EMBODIMENTS

Figure 1A:
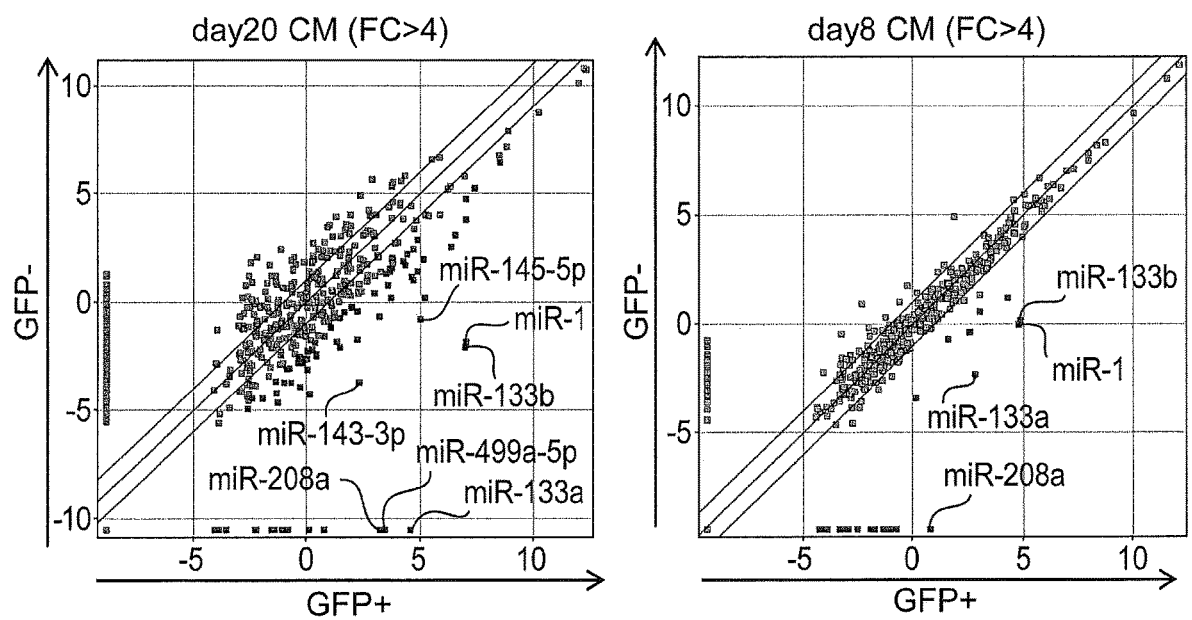
FIGS. 1(A) and 1(B) show the results of miRNA microarray performed on GFP-positive cells (cardiomyocytes) and GFP-negative cells (non-cardiomyocytes). 1(A): The left view shows the results of miRNA microarray performed on cells recovered by FACS on the 20th day after initiation of differentiation induction, whereas the right view shows the results of miRNA microarray performed on cells recovered by FACS on the 8th day after initiation of differentiation induction. 1(B): A Venn diagram showing miRNA whose expression was significantly high in GFP-positive cells on the 8th and 20th days after initiation of differentiation induction.

Hereinafter, the present invention will be described in detail in the following embodiments. However, the present invention is not limited to the following embodiments.

[Method for Sorting Cardiomyocytes]

According to one embodiment, the present invention provides a method for sorting out cardiomyocytes, comprising a step of introducing miRNA-responsive mRNA into a cell group. The cell group, into which miRNA-responsive mRNA has been introduced in an introduction step and which has become a target to be sorted, may be any given cells optionally comprising cardiomyocytes. For example, it may be a cell group induced to differentiate from pluripotent stem cells, or a cell population removed from a living body, but is not limited thereto. Accordingly, it is also possible to introduce miRNA-responsive mRNA into a cell group, regarding which whether or not it comprises cardiomyocytes is unknown. In a preferred embodiment, the cell group can be a cell group induced to differentiate from pluripotent stem cells. The cell group induced to differentiate from pluripotent stem cells means a cell group that has been subjected to a step of inducing differentiation of pluripotent stem cells into cardiomyocytes according to a method that will be described in detail later, and this cell group may comprise both cells that have become cardiomyocytes as a result of differentiation induction and cells that have not differentiated into cardiomyocytes. The pluripotent stem cells are not particularly limited, and examples of the pluripotent stem cells include the following.

(A) Embryonic Stem Cells

Embryonic stem cells (ES cells) are stem cells having pluripotency and proliferative ability associated with self-replication, which have been established from the internal cell mass of the early embryo (e.g., a blastocyst) of a mammal such as a human or a mouse.

ES cells are stem cells derived from an embryo that is derived from the internal cell mass of a blastocyst that is an embryo at the 8-cell stage of a fertilized egg after a morula, and have an ability to differentiate into all types of cells that constitute an adult body, namely, pluripotency, and proliferative ability associated with self-replication. ES cells have been discovered in a mouse in 1981 (M. J. Evans and M. H. Kaufman (1981), Nature 292: 154-156), and thereafter, ES cell lines have been established in primates such as a human and a monkey (J. A. Thomson et al. (1998), Science 282: 1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing an internal cell mass from the blastocyst of a fertilized egg of a target animal and then culturing the internal cell mass on feeder fibroblasts. In addition, the cells can be maintained by subculturing, using a culture medium to which substances such as a leukemia inhibitory factor (LIF) and a basic fibroblast growth factor (bFGF) have been added. The establishment of the ES cells of a human and a monkey and the maintenance thereof are described, for example, in U.S. Pat. No. 5,843,780; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; H. Kawasaki et al. (2002), Proc. Natl. Acad. Sci. USA, 99:1580-1585; Klimanskaya I, et al. (2006), Nature. 444:481-485.

As a culture medium used to produce ES cells, for example, a DMEM/F-12 culture medium, to which 0.1 mM 2-mercaptoethanol, 0.1 mM non-essential amino acid, 2 mM L-glutamic acid, 20% KSR and 4 ng/ml bFGF have been replenished, can be used, and human ES cells can be maintained at 37° C. in 5% $CO_2$, and in a humid atmosphere (H. Suemori et al. (2006), Biochem. Biophys. Res. Commun., 345: 926-932). Moreover, ES cells need to be subcultured every 3 to 4 days, and at this time, subculture can be carried out, for example, using 0.25% trypsin and 0.1 mg/ml collagenase IV in PBS containing 1 mM $CaCl_2$) and 20% KSR.

ES cells can be generally selected according to a Real-Time PCR method, using the expression of a gene marker, such as alkaline phosphatase, Oct-3/4 or Nanog, as an indicator. In particular, in the case of selecting human ES cells, the expression of a gene marker such as OCT-3/4, NANOG or ECAD can be used as an indicator (E. Kroon et al. (2008), Nat. Biotechnol., 26: 443-452).

Human ES cell lines, for example, WA01(H1) and WA09 (H9), are available from WiCell Research Institute, and KhES-1, KhES-2 and KhES-3 are available from Institute for Frontier Medical Sciences, Kyoto University (Kyoto, Japan).

(B) Spermatogonial Stem Cells

Spermatogonial stem cells are testis-derived pluripotent stem cells, which serve as an origin for spermatogenesis. These cells can be induced to differentiate into various cell lines, as with ES cells, and have properties such that, for example, a chimeric mouse can be produced if these cells are transplanted into a mouse blastocyst (M. Kanatsu-Shinohara et al. (2003) Biol. Reprod., 69: 612-616; K. Shinohara et al. (2004), Cell, 119: 1001-1012). Spermatogonial stem cells can be self-replicated in a culture medium comprising a glial cell line-derived neurotrophic factor (GDNF), or the spermatogonial stem cells can also be obtained by repeating a subculture under the same culture conditions as those for ES cells (Masanori Takebayashi et al. (2008), Jikken Igaku (Experimental Medicine), Vol. 26, No. 5 (extra number), pp. 41-46, Yodosha (Tokyo, Japan)).

(C) Embryonic Germ Cells

Embryonic germ cells are cells having the same pluripotency as that of ES cells, which are established from primordial germ cells at a fetal stage, and these cells can be established by culturing primordial germ cells in the presence of a substance such as LIF, bFGF or a stem cell factor (Y. Matsui et al. (1992), Cell, 70: 841-847; J. L. Resnick et al. (1992), Nature, 359: 550-551).

(D) Induced Pluripotent Stem Cells

Induced pluripotent stem (iPS) cells are artificial stem cells derived from somatic cells having properties that are almost equivalent to those of ES cells, such as pluripotency and proliferative ability associated with self-replication, which can be produced by introducing a specific reprogramming factor in the form of DNA, RNA or a protein into somatic cells (K. Takahashi and S. Yamanaka (2006) Cell, 126: 663-676; K. Takahashi et al. (2007), Cell, 131: 861-872; J. Yu et al. (2007), Science, 318: 1917-1920; Nakagawa, M. et al., Nat. Biotechnol. 26:101-106 (2008); International Publication No. WO 2007/069666). The reprogramming factor may be constituted with a gene specifically expressed in ES cells, a gene product or non-coding RNA thereof, or a gene playing an important role in the maintenance of undifferentiation of ES cells, a gene product or non-coding RNA thereof, or a low-molecular-weight compound. Examples of the gene comprised in the reprogramming factor include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1. These reprogramming factors may be used singly or in combinations of several types. Examples of such a combination of reprogramming factors include combinations described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO 2010/056831, WO2010/068955, WO2010/098419, WO2010/102267, WO 2010/111409, WO 2010/111422, WO2010/115050, WO2010/124290, WO2010/147395, WO2010/147612, Huangfu D, et al. (2008), Nat. Biotechnol., 26: 795-797, Shi Y. et al. (2008), Cell Stem Cell, 2: 525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P. et al. (2010), Stem Cells. 28:713-720, Maekawa M, et al. (2011), Nature. 474:225-9.

The above described reprogramming factor also includes histone deacetylase (HDAC) inhibitors [e.g., low-molecular-weight inhibitors such as valproic acid (VPA), trichostatin A, sodium butyrate, such as MC 1293 or M344, nucleic acid expression inhibitors such as siRNA and shRNA against HDAC (e.g., HDAC1 siRNA Smartpool (registered trademark) (Millipore), HuSH 29mershRNA Constructs against HDAC1 (OriGene), etc.), etc.], MEK inhibitors (e.g., PD184352, PD98059, U0126, SL327 and PD0325901), Glycogen synthase kinase-3 inhibitors (e.g., Bio and CHIR99021), DNA methyltransferase inhibitors (e.g., 5-azacytidine), histone methyltransferase inhibitors (e.g., low-molecular-weight inhibitors such as BIX-01294, nucleic acid expression inhibitors such as siRNA and shRNA against Suv39h1, Suv39h2, SetDB1 and G9a, etc.), L-channel calcium agonists (e.g., Bayk8644), butyric acid, TGFβ inhibitors or ALK5 inhibitors (e.g., LY364947, SB431542, 616453 and A-83-01), p53 inhibitors (e.g., siRNA and shRNA against p53), ARID3A inhibitors (e.g., siRNA and shRNA against ARID3A), miRNAs such as miR-291-3p, miR-294, miR-295 and mir-302, Wnt Signaling (e.g., soluble Wnt3a), neuropeptide Y, prostaglandins (e.g., prostaglandin E2 and prostaglandin J2), and factors used for the purpose of enhancing establishment efficiency, such as hTERT, SV40LT, UTF1, IRX6, GLIS1, PITX2 and DMRTB1. In the present description, these factors used for the purpose of improving establishment efficiency are not particularly distinguished from the reprogramming factor.

When the reprogramming factor has the form of a protein, it may be introduced into somatic cells, for example, according to means such as lipofection, fusion with a cell membrane permeable peptide (e.g., HIV-derived TAT and polyarginine), or microinjection.

On the other hand, when the reprogramming factor has the form of DNA, it can be introduced into somatic cells, for example, according to means, such as the use of vectors such as virus, plasmid or artificial chromosome, lipofection, liposome, or microinjection. Examples of the virus vector include a retrovirus vector, a lentivirus vector (both of which are disclosed in Cell, 126, pp. 663-676, 2006; Cell, 131, pp. 861-872, 2007; Science, 318, pp. 1917-1920, 2007), an adenovirus vector (Science, 322, 945-949, 2008), an adeno-associated virus vector, and a Sendai virus vector (WO 2010/008054). Examples of the artificial chromosomal vector include human artificial chromosome (HAC), yeast artificial chromosome (YAC), and bacterial artificial chromosome (BAC, PAC). As a plasmid, a plasmid for mammalian cells can be used (Science, 322: 949-953, 2008). The vector may comprise regulatory sequences such as a promoter, an enhancer, a ribosome-binding sequence, a terminator and a polyadenylation addition site, so that a nucleus reprogramming substance can be expressed. Furthermore, the vector may also comprise a drug resistance gene (e.g., a kanamycin resistance gene, an ampicillin resistance gene, a puromycin resistance gene, etc.), selective marker sequences such as a thymidine kinase gene and a diphtheria toxin gene, reporter gene sequences such as a green fluorescent protein (GFP), β-glucuronidase (GUS) and FLAG, etc., as necessary. Further, in order to remove both a gene or promoter encoding a reprogramming factor, and the reprogramming factor binding thereto after introduction of the above described vector into somatic cells, the vector may also have LoxP sequences before and after them.

Further, when the reprogramming factor has the form of RNA, it may be introduced into somatic cells, for example, according to means such as lipofection or microinjection. In order to suppress degradation, RNA, into which 5-methylcytidine and pseudouridine (TriLink Biotechnologies) have been incorporated, may also be used (Warren L, (2010) Cell Stem Cell. 7: 618-630).

Examples of the culture medium used to induce iPS cells include DMEM, DMEM/F, 12, and DME culture media, which comprise 10% to 15% FBS (wherein these culture media may further comprise LIF, penicillin/streptomycin, puromycin, L-glutamine, non-essential amino acids, β-mercaptoethanol and the like, as appropriate), and commercially available culture media [e.g., a culture medium for the culture of mouse ES cells (TX-WES culture medium, THROMBO X), a culture medium for the culture of primate ES cells (a culture medium for primate ES/iPS cells, ReproCELL), a serum-free medium (mTeSR, Stemcell Technology)].

As an example of the culture method, for example, somatic cells are allowed to come into contact with a reprogramming factor on a DMEM or DMEM/F12 culture medium containing 10% FBS at 37° C. in the presence of 5% $CO_2$, and the cells are then cultured for approximately 4 to 7 days. Thereafter, the cultured cells are dispersed again on feeder cells (for example, mitomycin C-treated STO cells, SNL cells, etc.). From approximately 10 days after the contact of the somatic cells with the reprogramming factor, the cells are cultured in a bFGF-containing culture medium for the culture of primate ES cells, so that approximately 30 to approximately 45 days or more after the contact, iPS-like colonies can be generated.

Alternatively, somatic cells are cultured in a DMEM culture medium containing 10% FBS (wherein the culture medium may further comprise LIF, penicillin/streptomycin, puromycin, L-glutamine, non-essential amino acids, 03-mercaptoethanol, etc., as appropriate) on feeder cells (for example, mitomycin C-treated STO cells, SNL cells, etc.) at 37° C. in the presence of 5% $CO_2$, and as a result, approximately 25 to approximately 30 or more days later, ES-like colonies can be generated. Desirably, a method of using somatic cells themselves to be reprogrammed (Takahashi K, et al. (2009), PLoS One. 4: e8067 or WO 2010/137746) or an extracellular substrate (e.g., Laminin-5 (WO2009/123349) and Matrigel (BD)), instead of feeder cells, can be applied as an example.

Other than this method, a method of culturing somatic cells using a serum-free medium can also be applied (Sun N, et al. (2009), Proc Natl Acad Sci USA. 106: 15720-15725). Moreover, in order to enhance establishment efficiency, iPS cells may be established under hypoxic conditions (an oxygen concentration of 0.1% or more and 15% or less) (Yoshida Y, et al. (2009), Cell Stem Cell. 5: 237-241, or WO 2010/013845).

During the aforementioned culture, from the second day after initiation of the culture, the culture medium is replaced with fresh medium one once a day. In addition, the number of somatic cells used for nuclear reprogramming is not limited, and it is in the range of approximately $5 \times 10^3$ to approximately $5 \times 10^6$ cells per 100-$cm^2$ culture dish.

iPS cells can be selected based on the shape of a formed colony. On the other hand, in a case in which a drug resistance gene, which is expressed in conjunction with a gene expressed when somatic cells are reprogrammed (e.g., Oct3/4 or Nanog), is introduced as a marker gene into cells, iPS cells established by culturing the cells in a culture medium comprising the corresponding drug (a selective culture medium) can be selected. Moreover, in a case in which such a marker gene is a fluorescent protein gene, iPS cells can be selected by observing under a fluorescence microscope, or in a case in which the marker gene is a luciferase gene, iPS cells can be selected by adding a luminescent substrate thereto, or in a case in which the marker gene is a chromogenic gene, iPS cells can be selected by adding a chromogenic substrate thereto.

The term "somatic cells" is used in the present description to mean all types of animal cells (preferably, the cells of mammals including humans), except for germ line cells such as an ovum, oocytes and ES cells, and totipotent cells. Such somatic cells include, but are not limited to, all of fetal (young) somatic cells, neonatal (young) somatic cells, and mature, healthy or diseased somatic cells. In addition, such somatic cells also include primary cultured cells, subcultured cells, and established cells. Specific examples of the somatic cells include (1) tissue stem cells (somatic stem cells), such as neural stem cells, hematopoietic stem cells, mesenchymal stem cells, or pulp stem cells, (2) tissue progenitor cells, and (3) differentiated cells, such as lymphocytes, epithelial cells, endothelial cells, muscle cells, fibroblasts (skin cells, etc.), hair cells, hepatocytes, gastric mucosa cells, intestinal cells, splenic cells, pancreatic cells (pancreatic exocrine cells, etc.), brain cells, lung cells, kidney cells and fat cells.

Furthermore, when iPS cells are used as materials for cells to be transplanted, from the viewpoint of prevention of rejection reaction, it is desirable to use somatic cells having an HLA genotype that is identical to or substantially identical to that of a transplantation destination. Herein, "substantially identical" means that their HLA genotypes are identical to each other to such an extent that the immune response can be suppressed by applying an immunosuppressant to the transplanted cells. Such cells are, for example, somatic cells having an HLA genotype, in which three alleles, HLA-A, HLA-B and HLA-DR are identical, or four alleles, namely, the above three alleles and HLA-C are identical between them.

(E) ES cells derived from cloned embryo obtained by nuclear transplantation

ES cells derived from a cloned embryo obtained by nuclear transplantation (nt ES cells) are ES cells derived from a cloned embryo produced by a nuclear transplantation technique, and these cells have almost the same properties as those of ES cells derived from a fertilized egg (T. Wakayama et al. (2001), Science, 292: 740-743; S. Wakayama et al. (2005), Biol. Reprod., 72: 932-936; J. Byrne et al. (2007), Nature, 450: 497-502). That is, ES cells established from the internal cell mass of a blastocyst derived from a cloned embryo that is obtained by replacing the nucleus of an unfertilized egg with the nucleus of a somatic cell are nt ES (nuclear transfer ES) cells. In order to produce such nt ES cells, a combination of a nuclear transplantation technique (J. B. Cibelli et al. (1998), Nature Biotechnol., 16: 642-646) with an ES cell production technique can be utilized (S. Wakayama et al. (2008), Jikken Igakru (Experimental Medicine), Vol. 26, No. 5 (extra number), pp. 47-52). In nuclear transplantation, reprogramming can be carried out by injecting the nucleus of a somatic cell into an unfertilized egg of a mammal, from which the nucleus has been removed, and culturing it for a few hours.

(F) Multilineage-Differentiating Stress Enduring Cells

Multilineage-differentiating Stress Enduring cells (Muse cells) are pluripotent stem cells produced by the method described in WO 2011/007900, and more specifically, Muse cells are cells having pluripotency obtained by subjecting fibroblasts or bone marrow stromal cells to a trypsin treatment for a long period of time, preferably for 8 hours or 16 hours, and then subjecting the resulting cells to suspension culture. The cells are positive to SSEA-3 and CD105.

Myocardial Differentiation Induction Method

The term "cardiomyocytes" is used in the present invention to mean, at least, cells which express cardiac troponin (cTnT) or αMHC. In the case of human, an example of cTnT is Accession number: NM_000364 assigned by NCBI, and in the case of mouse, it is Accession number: NM_001130174 assigned by NCBI. In the case of human, an example of caMHC is Accession number: NM_002471 assigned by NCBI, and in the case of mouse, it is Accession number: NM_001164171 assigned by NCBI. The origin of cardiomyocytes is not particularly limited in the present invention. For example, it may be cells comprised in peripheral blood, heart, bone marrow tissues, adipose tissues, skeletal muscle tissues, amniotic tissues, placental tissues, umbilical cord blood and the like, which are obtained by any given methods. In addition, it may also be induced and differentiated cells from pluripotent stem cells.

As a method of inducing differentiation of cells into cardiomyocytes applied in the present invention, cardiomyocytes can be produced from pluripotent stem cells, for example, according to the method reported by Laflamme M A et al. (Laflamme M A & Murry C E, Nature 2011, Review). Other than this method, examples of the differentiation induction method include, but are not limited to, a method of producing cardiomyocytes, which comprises subjecting induced pluripotent stem cells to suspension culture to form a cell mass (embryoid body), a method of producing cardiomyocytes in the presence of a substance that suppresses BMP signaling (WO 2005/033298), a method of producing cardiomyocytes, which comprises successive addition of Activin A and BMP (WO 2007/002136), a method of producing cardiomyocytes in the presence of a substance that promotes activation of a canonical Wnt signaling pathway (WO 2007/126077), and a method of producing cardiomyocytes in the presence of cyclosporine A, which comprises isolation of Flk/KDR-positive cells from induced pluripotent stem cells (WO 2009/118928).

The method of inducing differentiation of cells into cardiomyocytes is not particularly limited in the present invention. For example, the following method is applied.

<Step of Dissociating Pluripotent Stem Cells to Form Embryoid Body: Step (1)>

In the present invention, in the step of dissociating pluripotent stem cells, cells that adhere to one another to form a population are dissociated (separated) into individual cells. Examples of such a method of dissociating pluripotent stem cells include a method of mechanically dissociating the cells and a dissociation method using a dissociation solution having both protease activity and collagenase activity (e.g., Accutase™ and Accumax™, etc.) or a dissociation solution having only collagenase activity. Preferably, a method of dissociating pluripotent stem cells using a dissociation solution having both protease activity and collagenase activity (particularly preferably, Accumax) is applied.

In the present invention, an example of a method of forming an embryoid body is a method which comprises subjecting the dissociated pluripotent stem cells to a suspension culture, using a culture dish having a surface that has not been artificially treated for the purpose of improving adhesion with cells (e.g., a coating treatment using Matrigel (BD), collagen, gelatin, laminin, heparan sulfate proteoglycan, or entactin), or a culture dish having a surface that has been subjected to a treatment for artificially suppressing adhesion (e.g., a coating treatment using polyhydroxyethyl methacrylate (poly-HEMA)).

<Step of Culturing Embryoid Body in Culture Medium Containing Activin a, BMP4 and bFGF: Step (2)>

The culture medium used in the present step can be prepared by adding activin A, BMP4 and bFGF to a medium used in the culture of animal cells (a basal medium). Examples of the basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, Neurobasal Medium (Life Technologies), StemPro34 (Invitrogen), and a mixed medium thereof. The medium may comprise serum, or it may be a serum-free medium. As necessary, the medium may comprise, for example, one or more serum alternatives, such as albumin, transferrin, Knockout Serum Replacement (KSR) (a serum alternative of FBS upon the culture of ES cells), an N2 supplement (Invitrogen), a B27 supplement (Invitrogen), fatty acid, insulin, a collagen precursor, a trace element, 2-mercaptoethanol, and 1-thiolglycerol. The medium may also comprise one or more substances, such as lipid, amino acid, L-glutamine, Glutamax (Invitrogen), non-essential amino acid, vitamin, a growth factor, a low-molecular-weight compound, an antibiotic, an antioxidant, pyruvic acid, buffer, and inorganic salts. A preferred basal medium is StemPro34 comprising transferrin, 1-thiolglycerol, L-glutamine and ascorbic acid.

The concentration of activin A used in the present step is preferably 1 ng/ml to 100 ng/ml, and examples of the activin A concentration used in the present step include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. It is particularly preferably 12 ng/ml.

The concentration of BMP4 used in the present step is preferably 1 ng/ml to 100 ng/ml, and examples of the BMP4 concentration used in the present step include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. It is particularly preferably 18 ng/ml.

The concentration of bFGF used in the present step is preferably 1 ng/ml to 100 ng/ml, and examples of the bFGF concentration used in the present step include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. It is particularly preferably 10 ng/ml.

With regard to culture conditions, the culture temperature is not limited, and it is approximately 30° C. to 40° C., and preferably approximately 37° C., and the culture is desirably carried out under hypoxic conditions. Herein, the hypoxic conditions are conditions, in which an oxygen partial pressure lower than the oxygen partial pressure (20%) in the atmosphere is applied. For example, it is an oxygen partial pressure between 1% and 15%, and examples of such an oxygen partial pressure include 10%, 9%, 8%, 7%, 6%, 5%, 4%, 3%, 2%, and 1%. More preferably, it is 5%. The culture is carried out in an atmosphere containing $CO_2$ and $N_2$. The $CO_2$ concentration is preferably approximately 2% to 5%, and the $N_2$ concentration is preferably approximately 85% to 95%. In the present invention, the culture can be carried out most preferably under conditions in which an Oz concentration is 5%, $CO_2$ is 5%, and $N_2$ is 90%.

An example of the culture period is 1 day or more and 7 days or less. If taking into account the efficiency of establishing cardiomyocytes, examples of the culture period include 1 day or more and 5 days or less, and 2 days or more and 4 days or less.

<Step of Culturing Embryoid Body in Culture Medium Containing VEGF and Wnt Inhibitor: Step (3)>

The culture medium used in the present step can be prepared by adding VEGF and a Wnt inhibitor to a medium used in the culture of animal cells (a basal medium). Examples of the basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, Neurobasal Medium (Life Technologies), StemPro34 (Invitrogen), and a mixed medium thereof. The medium may comprise serum, or it may be a serum-free medium. As necessary, the medium may comprise, for example, one or more serum alternatives, such as albumin, transferrin, Knockout Serum Replacement (KSR) (a serum alternative of FBS upon the culture of ES cells), an N2 supplement (Invitrogen), a B27 supplement (Invitrogen), fatty acid, insulin, a collagen precursor, a trace element, 2-mercaptoethanol, and 1-thiolglycerol. The medium may also comprise one or more substances, such as lipid, amino acid, L-glutamine, Glutamax (Invitrogen), non-essential amino acid, vitamin, a growth factor, a low-molecular-weight compound, an antibiotic, an antioxidant, pyruvic acid, buffer, and inorganic salts. A preferred basal medium is StemPro34 comprising transferrin, 1-thiolglycerol, L-glutamine and ascorbic acid.

In the present invention, the Wnt inhibitor means a substance that inhibits signaling from the binding of Wnt to a receptor to accumulation of β catenin. The Wnt inhibitor is not particularly limited, as long as it is a substance that inhibits the binding of Wnt to a Frizzled family as a receptor or a substance that promotes decomposition of 0 catenin. Examples of the Wnt inhibitor include a DKK 1 protein (e.g., in the case of human, NCBI Accession number: NM_012242), sclerostin (e.g., in the case of human, NCBI Accession number: NM_025237), 1WR-1 (Merck Millipore), IWP-2 (Sigma-Aldrich), IWP-3 (Sigma-Aldrich), IWP-4 (Sigma-Aldrich), PNU-74654 (Sigma-Aldrich), XAV939 (Sigma-Aldrich), and a derivative thereof.

The Wnt inhibitor used in the present step may preferably be IWP-3 or IWP-4.

The concentration of the Wnt inhibitor such as IWP-3 or IWP-4 in a culture medium is not particularly limited, as long as it is a concentration in which Wnt is inhibited. The concentration of the Wnt inhibitor is preferably 1 nM to 50 μM, and examples of the concentration of the Wnt inhibitor include, but are not limited to, 1 nM, 10 nM, 50 nM, 100 nM, 500 nM, 750 nM, 1 μM, 2 μM, 3 μM, 4 μM, 5 μM, 6 M, 7 M, 8 M, 9 M, 10 M, 15 μM, 20 μM, 25 μM, 30 μM, 40 μM, and 50 μM. It is more preferably 1 μM.

The concentration of VEGF used in the present step is preferably 1 ng/ml to 100 ng/ml, and examples of the VEGF concentration used in the present step include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. It is more preferably 10 ng/ml.

With regard to culture conditions, the culture temperature is not limited, and it is approximately 30° C. to 40° C., and preferably approximately 37° C., and the culture is desirably carried out under hypoxic conditions. Herein, the hypoxic conditions are conditions, in which an oxygen partial pressure lower than the oxygen partial pressure (20%) in the atmosphere is applied. For example, it is an oxygen partial pressure between 1% and 15%, and examples of such an oxygen partial pressure include 10%, 9%, 8%, 7%, 6%, 5%, 4%, 3%, 2%, and 10%. More preferably, it is 5%. The culture is carried out in an atmosphere containing $CO_2$ and $N_2$. The $CO_2$ concentration is preferably approximately 2% to 5%, and the $N_2$ concentration is preferably approximately 85% to 95%. In the present invention, the culture can be carried out most preferably under conditions in which an $O_2$ concentration is 5%, $CO_2$ is 5%, and $N_2$ is 90%.

The upper limit of the culture period is not particularly determined, since a long-term culture does not affect the establishment of cardiomyocytes. The culture is preferably carried out for 4 days or more. Examples of the culture period include 4 days, 5 days, 6 days, 7 days, 8 days, 9 days, and 10 days.

<Step of Culturing Embryoid Body in Culture Medium Containing VEGF and bFGF: Step (4)>

The culture medium used in the present step can be prepared by adding VEGF and bFGF to a medium used in the culture of animal cells (a basal medium). Examples of the basal medium include IMDM medium, Medium 199 medium, Eagle's Minimum Essential Medium (EMEM) medium, aMEM medium, Dulbecco's modified Eagle's Medium (DMVEM) medium, Ham's F12 medium, RPMI 1640 medium, Fischer's medium, Neurobasal Medium (Life Technologies), StemPro34 (Invitrogen), and a mixed medium thereof. The medium may comprise serum, or it may be a serum-free medium. As necessary, the medium may comprise, for example, one or more serum alternatives, such as albumin, transferrin, Knockout Serum Replacement (KSR) (a serum alternative of FBS upon the culture of ES cells), N2 supplement (Invitrogen), B27 supplement (Invitrogen), fatty acid, insulin, collagen precursor, trace element, 2-mercaptoethanol, and 1-thiolglycerol. The medium may also comprise one or more substances, such as lipid, amino acid, L-glutamine, Glutamax (Invitrogen), non-essential amino acid, vitamin, a growth factor, a low-molecular-weight compound, an antibiotic, an antioxidant, pyruvic acid, buffer, and inorganic salts. A preferred basal medium is StemPro34 comprising transferrin, 1-thiolglycerol, L-glutamine and ascorbic acid.

The concentration of VEGF used in the present step is preferably 1 ng/ml to 100 ng/ml, and examples of the VEGF concentration used in the present step include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. It is more preferably 10 ng/ml.

The concentration of bFGF used in the present step is preferably 1 ng/ml to 100 ng/ml, and examples of the VEGF concentration used in the present step include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. It is more preferably 5 ng/ml.

With regard to culture conditions, the culture temperature is not limited, and it may be approximately 30° C. to 40° C., and preferably approximately 37° C. Herein, the hypoxic conditions are conditions, in which an oxygen partial pressure lower than the oxygen partial pressure (20%) in the atmosphere is applied. For example, it is an oxygen partial pressure between 1% and 15%, and examples of such an oxygen partial pressure include 10%, 9%, 8%, 7%, 6%, 5%, 4%, 3%, 2%, and 1%. More preferably, it is 5%. In the present step, the oxygen partial pressure may be equivalent to that in the atmosphere in the middle of the step. In this case, the upper limit of the culture period is not particularly determined, since the efficiency of inducing cardiomyocytes is not changed by carrying out the culture, particularly under hypoxic conditions. The culture is preferably carried out for 4 days or more under hypoxic conditions in the early stage of the step. In the present invention, preferably, the culture is carried out under conditions of 5% $O_2$, 5% $CO_2$ and 90% $N_2$ in the primary period of the step, and then, in the subsequent period, the culture is carried out in an air atmosphere containing 5% $CO_2$.

The upper limit of the culture period is not particularly determined, since a long-term culture does not affect the establishment of cardiomyocytes. The culture is preferably carried out for 12 days or more. Examples of the culture period include 8 days, 9 days, 10 days, 11 days, 12 days, 13 days, 14 days, 15 days, 16 days, 17 days, 18 days, 19 days, 20 days, 21 days, 22 days, and more days.

In the present invention, miRNA-responsive mRNA to be introduced into a cell group is preferably miRNA-responsive mRNA to be introduced into a cell group that has been subjected to a step of inducing differentiation of pluripotent stem cells into cardiomyocytes. The period, at which miRNA-responsive mRNA is introduced into the cell group that has been subjected to a step of inducing differentiation of pluripotent stem cells into cardiomyocytes, is not particularly limited, as long as it is a period at which cells are intended to be selected out. In a case in which a step of inducing differentiation of the cells is carried out using the method specifically mentioned in the above described section regarding a myocardial differentiation induction method, the period is preferably the 10th to 25th day from formation of an embryoid body, and more preferably 18th day from the embryoid body formation.

The miRNA-responsive mRNA to be introduced into the cell group consists of a sequence comprising (i) a nucleic acid that is specifically recognized by miRNA specifically expressed in cardiomyocytes and (ii) a nucleic acid corresponding to the coding region of a gene, wherein translation of (ii) the nucleic acid corresponding to the coding region of a gene into protein is regulated by the nucleic acid sequence in (i) above.

The miRNA-responsive mRNA consisting of a sequence comprising the above described (i) and (ii) is preferably mRNA comprising a nucleic acid corresponding to the coding region of a gene operably linked to a sequence specifically recognized by miRNA specifically expressed in cardiomyocytes (hereinafter referred to as a "miRNA target sequence"). The phrase "translation of (ii) the nucleic acid corresponding to the coding region of a gene into protein is regulated by the nucleic acid sequence in (i) above" is used to mean that, when miRNA specifically expressed in cardiomyocytes is present, translation of the nucleic acid corresponding to the coding region of a gene into protein is regulated depending on the abundance thereof. Preferably, it is mRNA, in which when miRNA specifically expressed in cardiomyocytes is present, translation of (ii) the nucleic acid corresponding to the coding region of a gene is suppressed depending on the abundance thereof, so that the translation level of the protein translated from (ii) the nucleic acid corresponding to the coding region of a gene is reduced. In the present invention, as described above, the miRNA-responsive mRNA that functions to suppress translation into protein, depending on the abundance of miRNA molecules specifically binding to a miRNA target sequence, is referred to as "miRNA-responsive OFF switch mRNA." That is to say, in the case of using the miRNA-responsive OFF switch mRNA, cells in which the translation level of the gene in (ii) above comprised in the mRNA is small can be selected as cardiomyocytes.

The "miRNA" of the present invention means short-chain non-coding RNA (20-25 nucleotides) present in a cell, which is associated with regulation of gene expression through inhibition of translation of mRNA into protein or decomposition of mRNA. This miRNA is transcribed as a single-stranded pri-miRNA capable of forming a hairpin loop structure comprising a region ranging from DNA to miRNA and a complementary strand thereof, and a portion thereof is then cleaved by an enzyme called "Drosha" in the nucleus. The portion is transported as pre-miRNA from the nucleus, and it is further cleaved by Dicer, so that it becomes functional.

The "miRNA specifically expressed in cardiomyocytes" in (i) above, which is used in the present invention, is not particularly limited, as long as it is miRNA that is expressed in cardiomyocytes at a higher level than in cells other than the cardiomyocytes. For instance, it may be miRNA that is highly expressed in cardiomyocytes at a percentage of 10% or more, 20% or more, 30% or more, 40% or more, 500/% or more, 60% or more, 70% or more, 80% or more, 90% or more, or a higher percentage, than in cells other than the cardiomyocytes. However, examples of the miRNA are not limited thereto. Such miRNA can be appropriately selected from miRNAs registered in the information in the database, and/or miRNAs described in publication information described in the database. Examples of such miRNA include the miRNAs shown in Table 1, but are not limited thereto. In the present invention, the "miRNA specifically expressed in cardiomyocytes" in (i) above may preferably be miR-1, miR-143-3p, miR-208a, miR-208b, and miR-499a-5p.

TABLE 1 miRNAs specifically expressed in cardiomyocytes and sequences thereof

| miRNA specifically expressed in cardiomyocytes | Sequence of miRNA (5' → 3') | SEQ ID NO: |
|---|---|---|
| hsa-miR-1 | uggaauguaaagaaguauguau | 1 |
| hsa-miR-22-5p | aguucuucaguggcaagcuuua | 2 |
| hsa-miR-133a | uuuggucccuucaaccagcug | 3 |
| hsa-miR-133b | uuuggucccuucaaccagcua | 4 |
| hsa-miR-143-3p | ugagaugaagcacuguagcuc | 5 |
| hsa-miR-145-3p | ggauuccuggaaauacuguucu | 6 |
| hsa-miR-208a | auaagacgagcaaaaagcuugu | 7 |
| hsa-miR-490-3p | caaccuggaggacuccaugcug | 8 |
| hsa-miR-490-5p | ccauggaucuccaggugggu | 9 |
| hsa-miR-499a-5p | uuaagacuugcagugauguuu | 10 |
| hsa-miR-1271-5p | cuuggcaccuagcaagcacuca | 11 |
| hsa-miR-3907 | aggugcuccaggcuggcucaca | 12 |
| hsa-miR-4324 | cccugagacccuaaccuuaa | 13 |
| hsa-let-7e-5p | ugagguaggagguuguauaguu | 14 |
| hsa-miR-208b | auaagacgaacaaaagguuugu | 65 |

In the present invention, the phrase "specifically recognized by miRNA specifically expressed in cardiomyocytes" in (i) above is used to mean that there is miRNA, which interacts with a plurality of certain proteins and forms an RNA-induced silencing complex (RISC).

In the present invention, the target sequence of miRNA is preferably a sequence completely complementary to the miRNA, for example. Otherwise, the miRNA target sequence may have a mismatch with a completely complementary sequence, as long as it can be recognized by miRNA. The mismatch with the sequence completely complementary to the miRNA is not particularly limited, as long as it is a mismatch that can be generally recognized by miRNA. With regard to the original function in cells in a living body, the aforementioned mismatch may be a mismatch of approximately 40% to 50%. Such a mismatch is not particularly limited, and for example, it is a mismatch that is 1%, 5%, 10%, 20%, 300/%  or 40% of 1 nucleotide, 2 nucleotides, 3 nucleotides, 4 nucleotides, 5 nucleotides, 6 nucleotides, 7 nucleotides, 8 nucleotides, 9 nucleotides, 10 nucleotides or the entire recognition sequence. In particular, like a miRNA target sequence on mRNA possessed by a cell, a portion other than a seed region, namely, a region on the 5'-side in a target sequence corresponding to approximately 16 nucleotides on the 3'-side of miRNA may particularly comprise a large number of mismatches. The seed region may not comprise such a mismatch, or may comprise a mismatch of 1 nucleotide, 2 nucleotides or 3 nucleotides. Such a sequence may have a base length comprising nucleotides to which the RISC specifically binds, and thus, the length is not particularly limited. It is a sequence consisting of preferably 18 nucleotides or more and less than 24 nucleotides, and more preferably 20 nucleotides or more and less than 22 nucleotides. In the present invention, the target sequence of miRNA can be appropriately determined and used by introducing miRNA-responsive mRNA having the aforementioned sequence into cardiomyocytes and cells other than the cardiomyocytes, and then confirming that the expression of the corresponding marker gene is suppressed only in the cardiomyocytes. In the present invention, the target sequences of preferred miRNAs that correspond to the "miRNAs specifically expressed in cardiomyocytes" are shown in Table 2.

TABLE 2 miRNAs specifically expressed in cardiomyocytes and target sequences thereof

| miRNA specifically expressed in cardiomyocytes | Target sequence of miRNA (5' → 3') | SEQ ID NO: |
|---|---|---|
| hsa-miR-1 | auacauacuucuuuacauucca | 15 |
| hsa-miR-22-5p | uaaagcuugccacugaagaacu | 16 |
| hsa-miR-133a | cagcugguugaaggggaccaaa | 17 |
| hsa-miR-133b | uagcugguugaaggggaccaaa | 18 |
| hsa-miR-143-3p | gagcuacagugcuucaucuca | 19 |
| hsa-miR-145-3p | agaacaguauuuccaggaaucc | 20 |
| hsa-miR-208a | acaagcuuuuugcucgucuuau | 21 |
| hsa-miR-490-3p | cagcauggaguccuccagguug | 22 |
| hsa-miR-490-5p | acccaccuggagauccaugg | 23 |
| hsa-miR-499a-5p | aaacaucacugcaagucuuaa | 24 |
| hsa-miR-1271-5p | ugagugcuugcuaggugccaag | 25 |
| hsa-miR-3907 | ugugagccagccuggagcaccu | 26 |
| hsa-miR-4324 | uuaagguuagggucucaggg | 27 |
| hsa-let-7e-5p | aacuauacaaccuccuaccuca | 28 |
| hsa-miR-208b | acaaaccuuuuguucgucuuau | 66 |

The above described (ii) "nucleic acid corresponding to the coding region of a gene" used in the present invention is a nucleic acid gene encoding a protein that is translated in a cell and enables the sorting of cardiomyocytes. As an example, the "gene" may be a marker gene. The "marker gene" is a gene encoding any given protein that is translated in a cell, functions as a marker, and enables the sorting of cardiomyocytes. Examples of the protein that is translated in a cell and is able to function as a marker include, but are not limited to, a gene encoding a protein that can be visualized and quantified by supporting fluorescence, luminescence, color development, or the fluorescence, luminescence or color development of fluorescent protein, a membrane protein, and genes encoding proteins that kill cells by their expression, such as an apoptosis-inducing gene and a suicide gene. In combination with such an apoptosis-inducing gene, an apoptosis-suppressing gene can be used as a marker gene.

In the present description, a protein translated from mRNA comprising a nucleic acid corresponding to the coding region of the marker gene is referred to as a marker protein.

In the present invention, examples of the fluorescent protein include: blue fluorescent proteins such as Sirius, BFP, or EBFP; cyan fluorescent proteins such as mTurquoise, TagCFP, AmCyan, mTFP1, MidoriishiCyan, or CFP; green fluorescent proteins such as TurboGFP, AcGFP, TagGFP, Azami-Green (e.g. hmAG1), ZsGreen, EmGFP, EGFP, GFP2, or HyPer; yellow fluorescent proteins such as TagYFP, EYFP, Venus, YFP, PhiYFP, PhiYFP-m, TurboYFP, ZsYellow, or mBanana; orange fluorescent proteins such as KusabiraOrange (e.g. hmKO2) or mOrange; red fluorescent proteins such as TurboRFP, DsRed-Express, DsRed2, TagRFP, DsRed-Monomer, AsRed2, or mStrawberry; and near infrared fluorescent proteins such as TurboFP602, mRFPI, JRed, KillerRed, mCherry, HcRed, KeimaRed (e.g. hdKeimaRed), mRasberry, or mPlum, but examples of the fluorescent protein are not limited thereto.

In the present invention, an example of the luminescent protein is aequorin, but examples are not limited thereto. In addition, examples of the protein supporting fluorescence, luminescence or color development include enzymes decomposing fluorescence, luminescence or color development precursors, such as luciferase, phosphatase, peroxidase, or 3 lactamase, but examples of this protein are not limited thereto. In the present invention, when the substance supporting fluorescence, luminescence or color development is used as a marker gene, sorting of a cardiomyocyte is carried out by allowing a cell group to come into contact with a corresponding precursor, or by introducing such a corresponding precursor into a cell group.

In the present invention, the apoptosis-inducing gene means a gene encoding a protein having an apoptosis-inducing activity on cells. Examples of the apoptosis-inducing gene include IκB, Smac/DIABLO, ICE, HtrA2/OMI, AIF, endonuclease G, Bax, Bak, Noxa, Hrk (harakiri), Mtd, Bim, Bad, Bid, PUMA, activated caspase-3, Fas, and Tk, but the examples are not limited thereto. In the present invention, Bim is preferably used as such an apoptosis-inducing gene.

In the present invention, the suicide gene means a gene whose expression in a cell is fatal to the cell. In the present invention, the suicide gene may be a gene bringing cell death to a cell by itself (e.g., diphtheria toxin A), or may also be a gene whose expression allows a cell to be sensitive to a specific drug (e.g., the expression of a herpes simplex thymidine kinase gene allows cells to be sensitive to an antiviral compound). Examples of the suicide gene include genes encoding diphtheria toxin A, herpes simplex thymidine kinase (HSV-TK), carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella-zoster virus thymidine kinase (VZV-TK), and xanthine-guanine phosphoribosyl transferase (XGPRT), but the examples are not limited thereto. In the present invention, HSV-TK is preferably used as such a suicide gene.

In the present invention, the above described marker gene may comprise a gene encoding a localization signal. Examples of such a localization signal include a nuclear localization signal, a cell membrane localization signal, a mitochondrial localization signal, and a protein secretion signal. Specific examples include a classical nuclear localization sequence (NLS), an M9 sequence, a mitochondrial target sequence (MTS), and an endoplasmic reticulum localization sequence, but examples are not limited thereto. Such a localization signal is particularly advantageous, when the sorting step in the after-mentioned method for producing cardiomyocytes is carried out on an image, in the below-mentioned imaging cytometry or the like.

In the present invention, the phrase "a marker gene is operably linked to the target sequence of miRNA" means that at least one target sequence of miRNA is comprised in the 5'-UTR and 3'-UTR of an open reading frame encoding the marker gene (including an initiation codon), and/or in the open reading frame. The miRNA-responsive mRNA preferably comprises, in the direction from the 5'-terminus to the 3'-terminus, a Cap structure (7-methylguanosine 5'-phosphate), an open reading frame encoding the marker gene, and poly(A) tail, and also comprises, in the 5'-UTR, in the 3'-UTR, and/or in the open reading frame, at least one target sequence of miRNA. The position of the target sequence of miRNA in the mRNA may be either 5'-UTR or 3'-UTR, or may also be in the open reading frame (on the 3'-terminal side of the initiation codon). Otherwise, the mRNA may comprise target sequences of miRNA in all of these positions. Accordingly, the number of miRNA target sequences may be 1, 2, 3, 4, 5, 6, 7, 8, or more.

Preferably, in miRNA-responsive mRNA, the nucleic acids (i) and (ii) are linked to each other in the direction from 5' to 3' in this order. Accordingly, it is adequate if only one target sequence of miRNA may be present in the 5'-UTR. This is because it can achieve efficient translational inhibition. At this time, the number of nucleotides and the type of nucleotides between the cap structure and the target sequence of miRNA may be freely determined, as long as they do not constitute a stem structure or a steric structure. For instance, the cap structure and the miRNA target sequence can be designed, such that the number of nucleotides between the cap structure and the miRNA target sequence can be 0 to 50 nucleotides, and preferably 10 to 30 nucleotides. Moreover, the number of nucleotides and the type of nucleotides between the miRNA target sequence and the initiation codon may be freely determined, as long as they do not constitute a stem structure or a steric structure. The location of the miRNA target sequence and the initiation codon can be designed, such that the number of nucleotides between the miRNA target sequence and the initiation codon is 0 to 50 nucleotides, and preferably 10 to 30 nucleotides.

In the present invention, it is preferable that AUG acting as an initiation codon not be present in the miRNA target sequence in the miRNA-responsive mRNA. For example, in a case in which the target sequence of miRNA is present in the 5'-UTR and the target sequence comprises AUG therein, in relation to a marker gene linked to the 3' side, it is preferably designed to be in-frame. Otherwise, in a case in which the target sequence comprises AUG therein, it is also possible to convert AUG in the target sequence to GUG and then to use it. Moreover, in order to keep the influence of AUG in the target sequence to a minimum, the location of the target sequence in the 5'-UTR can be changed, as appropriate. For instance, the location of the target sequence in the 5'-UTR can be designed, so that the number of nucleotides between a cap structure and the AUG sequence in the target sequence can be 0 to 60 nucleotides, for example, 0 to 15 nucleotides, 10 to 20 nucleotides, 20 to 30 nucleotides, 30 to 40 nucleotides, 40 to 50 nucleotides, or 50 to 60 nucleotides.

The mRNA of the present invention preferably comprises modified nucleotides such as pseudo uridine and 5-methylcytidine, instead of ordinary uridine and cytidine. This is because of reduction in cytotoxicity. Such modified nucleotides can be positioned independently or as a part of the mRNA, in both cases of uridine and cytidine. In the case of being comprised as a part, the nucleotides can be positioned randomly at any given ratio.

In the present invention, when the target sequence of miRNA is present in the 5'-UTR, the following sequences can be adopted, for example.

TABLE 3 miRNAs specifically expressed in cardiomyocytes, and 5'-UTR sequences in miRNA-responsive mRNAs corresponding thereto

| miRNA specifically expressed in cardiomyocytes | Sequence of 5'-UTR in miRNA-responsivemRNA (5' → 3') (AUG at 3'-end indicates initiation codon) | SEQ ID NO: |
|---|---|---|
| hsa-miR-1 | GGUUCCGCGAUCGCGGAUCCAUACAUACUUCUUUACAUUCCAAGAUCACACCGGUCGCCACCAUG | 29 |
| hsa-miR-22-5p | GGUUCCGCGAUCGCGGAUCCUAAAGCUUGCCACUGAAGAACUAGAUCACACCGGUCGCCACCAUG | 30 |
| hsa-miR-133a | GGUUCCGCGAUCGCGGAUCCCAGCUGGUUGAAGGGGACCAAAAGAUCACACCGGUCGCCACCAUG | 31 |
| hsa-miR-133b | GGUUCCGCGAUCGCGGAUCCUAGCUGGUUGAAGGGGACCAAAAGAUCACACCGGUCGCCACCAUG | 32 |
| hsa-miR-143-3p | GGUUCCGCGAUCGCGGAUCCGAGCUACAGUGCUUCAUCUCAAGAUCAACACCGGUCGCCACCAUG | 33 |
| hsa-miR-145-3p | GGUUCCGCGAUCGCGGAUCCAGAACAGUAUUUCCAGGAAUCCAGAUCACACCGGUCGCCACCAUG | 34 |
| hsa-miR-208a | GGUUCCGCGAUCGCGGAUCCACAAGCUUUUUGCUCGUCUUAUAGAUCACACCGGUCGCCACCAUG | 35 |
| hsa-miR-490-3p | GGUUCCGCGAUCGCGGAUCCACCCACCUGGAGAUCCAUGGAGAUCAAACACCGGUCGCCACCAUG | 36 |
| hsa-miR-490-5p | GGUUCCGCGAUCGCGGAUCCCAGCAUGGAGUCCUCCAGGUUGAGAUCACACCGGUCGCCACCAUG | 37 |
| hsa-miR-499a-5p | GGUUCCGCGAUCGCGGAUCCAAACAUCACUGCAAGUCUUAAAGAUCAACACCGGUCGCCACCAUG | 38 |
| hsa-miR-1271-5p | GGUUCCGCGAUCGCGGAUCCUGAGUGCUUGCUAGGUGCCAAGAGAUCACACCGGUCGCCACCAUG | 39 |
| hsa-miR-3907 | GGUUCCGCGAUCGCGGAUCCUGUGAGCCAGCCUGGAGCACCUAGAUCACACCGGUCGCCACCAUG | 40 |
| hsa-miR-4324 | GGUUCCGCGAUCGCGGAUCCUUAAGGUUAGGGUCUCAGGGAGAUCAAACACCGGUCGCCACCAUG | 41 |
| hsa-let-7e-5p | GGUUCCGCGAUCGCGGAUCCAACUAUACAACCUCCUACCUCAAGAUCACACCGGUCGCCACCAUG | 42 |
| hsa-miR-208b | GGUUCCGCGAUCGCGGAUCCACAAACCUUUUGUUCGUCUUAUAGAUCACACCGGUCGCCACCAUG | 67 |

In the present invention, when the target sequence of miRNA is present in the 5'-UTR, for example, the following sequence can be adopted as downstream of the subsequent marker gene (i.e., 3'-UTR). At this time, as a marker gene located between the 5'-UTR and the 3'-UTR, any given genes described above can be used.

TABLE 4

3'-UTR sequence

| Sequence of 3'-UTR | SEQ ID NO: |
|---|---|
| CCUGUGAUGCAGAAGAAAACACUCGGCUGGGAGGCCUUCACCGAGACGCUGUACCCCGCUGACGGCGGCCUGGAAGGCAGAAACGACAUGGCCCUGAAGCUCGUGGGCGGGAGCCAUCUGAUCGCAAACAUCAAGACCACAUAUAGAUCCAAGAAACCCGCUAAGAACCUCAAGAUGCCUGGCGUCUACUAUGUGGACUACAGACUGGAAAGAAUCAAGGAGGCCAACAACGAGACCUACGUCGAGCAGCACGAGGUGGCAGUGGCCAGAUACUGCGACCUCCCUGACAAACUGGGGCACAGAUCUCAUAUGCAUCUCGAGUGAUAGUCUAGACCUUCUGCGGGGC | 43 |

TABLE 4-continued

3'-UTR sequence

| Sequence of 3'-UTR | SEQ ID NO: |
|---|---|
| UUGCCUUCUGGCCAUGCCCUUCUUCUCUCCCUUGCACCUGUACCUCUUGGUCUUUGAAUAAAGCCUGAGUAGGAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAAA | |

In the present invention, when a gene encoding BFP can be used as a marker gene, for example, the following sequences can be adopted as full-length miRNA-responsive mRNAs in the present invention, for each miRNAs specifically expressed in cardiomyocytes.

TABLE 5 miRNAs specifically expressed in cardiomyocytes and full-length miRNA-responsive mRNAs corresponding thereto

| miRNA specifically expressed in cardiomyocytes | Full length of miRNA-responsive mRNA | SEQ ID NO: |
|---|---|---|
| hsa-miR-1 | GGUUCCUUAAUCGCGGAUCCAUACAUACUUCUUU ACAUUCCAAGAUCACACCGGUCGCCACCAUGGGA UCCAGCGAGCUGAUUAAGGAGAACAUGCACAUGA AGCUGUACAUGGAGGGCACCGUGGACAACCAUCA CUUCAAGUGCACAUCCGAGGGCGAAGGCAAGCCC UACGAGGGCACCCAGACCAUGAGAAUCAAGGUGG UCGAGGGCGGCCCUCUCCCCUUCGCCUUCGACAUC CUGGCUACUAGCUUCCUCUACGGCAGCAAGACCU UCAUCAACCACACCCAGGGCAUCCCCGACUUCUUC AAGCAGUCCUUCCCUGAGGGCUUCACAUGGGAGA GAGUCACCACAUACGAAGACGGGGGCGUGCUGAC CGCUACCCAGGACACCAGCCUCCAGGACGGCUGCC UCAUCUACAACGUCAAGAUCAGAGGGGUGAACUU CACAUCCAACGGCCCUGUGAUGCAGAAGAAAACA CUCGGCUGGGAGGCCUUCACCGAGACGCUGUACC CCGCUGACGGCGGCCUGGAAGGCAGAAACGACAU GGCCCUGAAGCUCGUGGGCGGGAGCCAUCUGAUC GCAAACAUCAAGACCACAUAUAGAUCCAAGAAAC CCGCUAAGAACCUCAAGAUGCCUGGCGUCUACUA UGUGGACUACAGACUGGAAAGAAUCAAGGAGGCC AACAACGAGACCUACGUCGAGCAGCACGAGGUGG CAGUGGCCAGAUACUGCGACCUCCCUAGCAAACU GGGGCACAGAUCUCAUAUGCAUCUCGAGUGAUAG UCUAGACCUUCUGCGGGGCUUGCCUUCUGGCCAU GCCCUUCUUCUCUCCCUUGCACCUGUACCUCUUGG UCUUUGAAUAAAGCCUGAGUAGGAAAAAAAAAAA AAAAAAAAAAAAAAAAAAAAAAAAAAAAAAA AAAAAAAAAAAAAAAAAAAAAAAAAAAAAAA AAAAAAAAAAAAAAAAAAAAAAAAAAAAAAA AAAAAAAAA | 44 |
| hsa-miR-22-5p | GGUUCCUUAAUCGCGGAUCCUAAAGCUUGCCACU GAAGAACUAGAUCACACCGGUCGCCACCAUGGGA UCCAGCGAGCUGAUUAAGGAGAACAUGCACAUGA AGCUGUACAUGGAGGGCACCGUGGACAACCAUCA CUUCAAGUGCACAUCCGAGGGCGAAGGCAAGCCC UACAGGGGCACCCAGACCAUGAGAAUCAAGGUGG UCGAGGGCGGCCCUCUCCCCUUCGCCUUCGACAUC CUGGCUACUAGCUUCCUCUACGGCAGCAAGACCU UCAUCAACCACACCCAGGGCAUCCCCGACUUCUUC AAGCAGUCCUUCCCUGAGGGCUUCACAUGGGAGA GAGUCACCACAUACGAAGACGGGGGCGUGCUGAC CGCUACCCAGGACACCAGCCUCCAGGACGGCUGCC UCAUCUACAACGUCAAGAUCAGAGGGGUGAACUU CACAUCCAACGGCCCUGUGAUGCAGAAGAAAACA CUCGGCUGGGAGGCCUUCACCGAGACGCUGUACC CCGCUGACGGCGGCCUGGAAGGCAGAAACGACAU GGCCCUGAAGCUCGUGGGCGGGAGCCAUCUGAUC GCAAACAUCAAGACCACAUAUAGAUCCAAGAAAC CCGCUAAGAACCUCAAGAUGCCUGGCGUCUACUA UGUGGACUACAGACUGGAAAGAAUCAAGGAGGCC AACAACGAGACCUACGUCGAGCAGCACGAGGUGG CAGUGGCCAGAUACUGCGACCUCCCUAGCAAACU GGGGCACAGAUCUCAUAUGCAUCUCGAGUGAUAG UCUAGACCUUCUGCGGGGCUUGCCUUCUGGCCAU GCCCUUCUUCUCUCCCUUGCACCUGUACCUCUUGG UCUUUGAAUAAAGCCUGAGUAGGAAAAAAAAAAA AAAAAAAAAAAAAAAAAAAAAAAAAAAAAAA AAAAAAAAAAAAAAAAAAAAAAAAAAAAAAA AAAAAAAAAAAAAAAAAAAAAAAAAAAAAAA AAAAAAAAA | 45 |
| hsa-miR-133a-3p | GGUUCCUUAAUCGCGGAUCCCAGCUGGUUGAAGG GGACCAAAAGAUCACACCGGUCGCCACCAUGGGA UCCAGCGAGCUGAUUAAGGAGAACAUGCACAUGA AGCUGUACAUGGAGGGCACCGUGGACAACCAUCA CUUCAAGUGCACAUCCGAGGGCGAAGGCAAGCCC UACGAGGGCACCCAGACCAUGAGAAUCAAGGUGG UCGAGGGCGGCCCUCUCCCCUUCGCCUUCGACAUC CUGGCUACUAGCUUCCUCUACGGCAGCAAGACCU UCAUCAACCACACCCAGGGCAUCCCCGACUUCUUC AAGCAGUCCUUCCCUGAGGGCUUCACAUGGGAGA | 46 |

TABLE 5-continued miRNAs specifically expressed in cardiomyocytes and
full-length miRNA-responsive mRNAs corresponding thereto

| miRNA specifically expressed in cardiomyocytes | Full length of miRNA-responsive mRNA | SEQ ID NO: |
|---|---|---|
| | GAGUCACCACAUACGAAGACGGGGGCGUGCUGAC<br>CGCUACCCAGGACACCAGCCUCCAGGACGGCUGCC<br>UCAUCUACAACGUCAAGAUCAGAGGGGUGAACUU<br>CACAUCCAACGGCCCUGUGAUGCAGAAGAAAACA<br>CUCGGCUGGGAGGCCUUCACCGAGACGCUGUACC<br>CCGCUGACGGCGGCCUGGAAGGCAGAAACGACAU<br>GGCCCUGAAGCUCGUGGGCGGGAGCCAUCUGAUC<br>GCAAACAUCAAGACCACAUAUAGAUCCAAGAAAC<br>CCGCUAAGAACCUCAAGAUGCCUGGCGUCUACUA<br>UGUGGACUACAGACUGGAAAGAAUCAAGGAGGCC<br>AACAACGAGACCUACGUCGAGCAGCACGAGGUGG<br>CAGUGGCCAGAUACUGCGACCUCCCUAGCAAACU<br>GGGGCACAGAUCUCAUAUGCAUCUCGAGUGAUAG<br>UCUAGACCUUCUGCGGGGCUUGCCUUCUGGCCAU<br>GCCCUUCUUCUCUCCCUUGCACCUGUACCUCUUGG<br>UCUUUGAAUAAAGCCUGAGUAGGAAAAAAAAAAA<br>AAAAAAAAAAAAAAAAAAAAAAAAAAAAAAAA<br>AAAAAAAAAAAAAAAAAAAAAAAAAAAAAAAA<br>AAAAAAAAAAAAAAAAAAAAAAAAAAAAAAAA<br>AAAAAAAAAA | |
| hsa-miR-133b | GGUUCCUUAAUCGCGGAUCCUAGCUGGUUGAAGG<br>GGACCAAAAGAUCACACCGGUCGCCACCAUGGGA<br>UCCAGCGAGCUGAUUAAGGAGAACAUGCACAUGA<br>AGCUGUACAUGGAGGGCACCGUGGACAACCAUCA<br>CUUCAAGUGCACAUCCGAGGGCGAAGGCAAGCCC<br>UACGAGGGCACCCAGACCAUGAGAAUCAAGGUGG<br>UCGAGGGCGGCCCUCUCCCCUUCGCCUUCGACAUC<br>CUGGCUACUAGCUUCCUCUACGGCAGCAAGACCU<br>UCAUCAACCACACCCAGGGCAUCCCCGACUUCUUC<br>AAGCAGUCCUUCCCUGAGGGCUUCACAUGGGAGA<br>GAGUCACCACAUACGAAGACGGGGGCGUGCUGAC<br>CGCUACCCAGGACACCAGCCUCCAGGACGGCUGCC<br>UCAUCUACAACGUCAAGAUCAGAGGGGUGAACUU<br>CACAUCCAACGGCCCUGUGAUGCAGAAGAAAACA<br>CUCGGCUGGGAGGCCUUCACCGAGACGCUGUACC<br>CCGCUGACGGCGGCCUGGAAGGCAGAAACGACAU<br>GGCCCUGAAGCUCGUGGGCGGGAGCCAUCUGAUC<br>GCAAACAUCAAGACCACAUAUAGAUCCAAGAAAC<br>CCGCUAAGAACCUCAAGAUGCCUGGCGUCUACUA<br>UGUGGACUACAGACUGGAAAGAAUCAAGGAGGCC<br>AACAACGAGACCUACGUCGAGCAGCACGAGGUGG<br>CAGUGGCCAGAUACUGCGACCUCCCUAGCAAACU<br>GGGGCACAGAUCUCAUAUGCAUCUCGAGUGAUAG<br>UCUAGACCUUCUGCGGGGCUUGCCUUCUGGCCAU<br>GCCCUUCUUCUCUCCCUUGCACCUGUACCUCUUGG<br>UCUUUGAAUAAAGCCUGAGUAGGAAAAAAAAAAA<br>AAAAAAAAAAAAAAAAAAAAAAAAAAAAAAAA<br>AAAAAAAAAAAAAAAAAAAAAAAAAAAAAAAA<br>AAAAAAAAAAAAAAAAAAAAAAAAAAAAAAAA<br>AAAAAAAAAA | 47 |
| hsa-miR-143-3p | GGUUCCUUAAUCGCGGAUCCGAGCUACAGUGCUU<br>CAUCUCAAGAUCAACACCGGUCGCCACCAUGGGA<br>UCCAGCGAGCUGAUUAAGGAGAACAUGCACAUGA<br>AGCUGUACAUGGAGGGCACCGUGGACAACCAUCA<br>CUUCAAGUGCACAUCCGAGGGCGAAGGCAAGCCC<br>UACGAGGGCACCCAGACCAUGAGAAUCAAGGUGG<br>UCGAGGGCGGCCCUCUCCCCUUCGCCUUCGACAUC<br>CUGGCUACUAGCUUCCUCUACGGCAGCAAGACCU<br>UCAUCAACCACACCCAGGGCAUCCCCGACUUCUUC<br>AAGCAGUCCUUCCCUGAGGGCUUCACAUGGGAGA<br>GAGUCACCACAUACGAAGACGGGGGCGUGCUGAC<br>CGCUACCCAGGACACCAGCCUCCAGGACGGCUGCC<br>UCAUCUACAACGUCAAGAUCAGAGGGGUGAACUU<br>CACAUCCAACGGCCCUGUGAUGCAGAAGAAAACA<br>CUCGGCUGGGAGGCCUUCACCGAGACGCUGUACC<br>CCGCUGACGGCGGCCUGGAAGGCAGAAACGACAU<br>GGCCCUGAAGCUCGUGGGCGGGAGCCAUCUGAUC<br>GCAAACAUCAAGACCACAUAUAGAUCCAAGAAAC<br>CCGCUAAGAACCUCAAGAUGCCUGGCGUCUACUA<br>UGUGGACUACAGACUGGAAAGAAUCAAGGAGGCC | 48 |

TABLE 5-continued miRNAs specifically expressed in cardiomyocytes and full-length miRNA-responsive mRNAs corresponding thereto

| miRNA specifically expressed in cardiomyocytes | Full length of miRNA-responsive mRNA | SEQ ID NO: |
|---|---|---|
| | AACAACGAGACCUACGUCGAGCAGCACGAGGUGG CAGUGGCCAGAUACUGCGACCUCCCUAGCAAACU GGGGCACAGAUCUCAUAUGCAUCUCGAGUGAUAG UCUAGACCUUCUGCGGGGCUUGCCUUCUGGCCAU GCCCUUCUUCUCUCCCUUGCACCUGUACCUCUUGG UCUUUGAAUAAAGCCUGAGUAGGAAAAAAAAAA AAAAAAAAAAAAAAAAAAAAAAAAAAAAA AAAAAAAAAAAAAAAAAAAAAAAAAAAAA AAAAAAAAAAAAAAAAAAAAAAAAAAAAA AAAAAAAAA | |
| hsa-miR-145-3p | GGUUCCUUAAUCGCGGAUCCAGAACAGUAUUUCC AGGAAUCCAGAUCACACCGGUCGCCACCAUGGGA UCCAGCGAGCUGAUUAAGGAGAACAUGCACAUGA AGCUGUACAUGGAGGGCACCGUGGACAACCAUCA CUUCAAGUGCACAUCCGAGGGCGAAGGCAAGCCC UACGAGGGCACCCAGACCAUGAGAAUCAAGGUGG UCGAGGGCGGCCCUCUCCCCUUCGCCUUCGACAUC CUGGCUACUAGCUUCCUCUACGGCAGCAAGACCU UCAUCAACCACACCCAGGGCAUCCCCGACUUCUUC AAGCAGUCCUUCCCUGAGGGCUUCACAUGGGAGA GAGUCACCACAUACGAAGACGGGGGCGUGCUGAC CGCUACCCAGGACACCAGCCUCCAGGACGGCUGCC UCAUCUACAACGUCAAGAUCAGAGGGGUGAACUU CACAUCCAACGGCCCUGUGAUGCAGAAGAAAACA CUCGGCUGGGAGGCCUUCACCGAGACGCUGUACC CCGCUGACGGCGCCUGGAAGGCAGAAACGACAU GGCCCUGAAGCUCGUGGGCGGGAGCCAUCUGAUC GCAAACAUCAAGACCACAUAUAGAUCCAAGAAAC CCGCUAAGAACCUCAAGAUGCCUGGCGUCUACUA UGUGGACUACAGACUGGAAAGAAUCAAGGAGGCC AACAACGAGACCUACGUCGAGCAGCACGAGGUGG CAGUGGCCAGAUACUGCGACCUCCCUAGCAAACU GGGGCACAGAUCUCAUAUGCAUCUCGAGUGAUAG UCUAGACCUUCUGCGGGGCUUGCCUUCUGGCCAU GCCCUUCUUCUCUCCCUUGCACCUGUACCUCUUGG UCUUUGAAUAAAGCCUGAGUAGGAAAAAAAAAA AAAAAAAAAAAAAAAAAAAAAAAAAAAAA AAAAAAAAAAAAAAAAAAAAAAAAAAAAA AAAAAAAAAAAAAAAAAAAAAAAAAAAAA AAAAAAAAA | 49 |
| hsa-miR-208a-3p | GGUUCCUUAAUCGCGGAUCCACAAGCUUUUUGCU CGUCUUAUAGAUCACACCGGUCGCCACCAUGGGA UCCAGCGAGCUGAUUAAGGAGAACAUGCACAUGA AGCUGUACAUGGAGGGCACCGUGGACAACCAUCA CUUCAAGUGCACAUCCGAGGGCGAAGGCAAGCCC UACGAGGGCACCCAGACCAUGAGAAUCAAGGUGG UCGAGGGCGGCCCUCUCCCCUUCGCCUUCGACAUC CUGGCUACUAGCUUCCUCUACGGCAGCAAGACCU UCAUCAACCACACCCAGGGCAUCCCCGACUUCUUC AAGCAGUCCUUCCCUGAGGGCUUCACAUGGGAGA GAGUCACCACAUACGAAGACGGGGGCGUGCUGAC CGCUACCCAGGACACCAGCCUCCAGGACGGCUGCC UCAUCUACAACGUCAAGAUCAGAGGGGUGAACUU CACAUCCAACGGCCCUGUGAUGCAGAAGAAAACA CUCGGCUGGGAGGCCUUCACCGAGACGCUGUACC CCGCUGACGGCGCCUGGAAGGCAGAAACGACAU GGCCCUGAAGCUCGUGGGCGGGAGCCAUCUGAUC GCAAACAUCAAGACCACAUAUAGAUCCAAGAAAC CCGCUAAGAACCUCAAGAUGCCUGGCGUCUACUA UGUGGACUACAGACUGGAAAGAAUCAAGGAGGCC AACAACGAGACCUACGUCGAGCAGCACGAGGUGG CAGUGGCCAGAUACUGCGACCUCCCUAGCAAACU GGGGCACAGAUCUCAUAUGCAUCUCGAGUGAUAG UCUAGACCUUCUGCGGGGCUUGCCUUCUGGCCAU GCCCUUCUUCUCUCCCUUGCACCUGUACCUCUUGG UCUUUGAAUAAAGCCUGAGUAGGAAAAAAAAAA AAAAAAAAAAAAAAAAAAAAAAAAAAAAA AAAAAAAAAAAAAAAAAAAAAAAAAAAAA AAAAAAAAAAAAAAAAAAAAAAAAAAAAA AAAAAAAAA | 50 |

TABLE 5-continued miRNAs specifically expressed in cardiomyocytes and
full-length miRNA-responsive mRNAs corresponding thereto

| miRNA specifically expressed in cardiomyocytes | Full length of miRNA-responsive mRNA | SEQ ID NO: |
|---|---|---|
| hsa-miR-490-3p | GGUUCCUUAAUCGCGGAUCCCAGCAUGGAGUCCU<br>CCAGGUUGAGAUCACACCGGUCGCCACCAUGGGA<br>UCCAGCGAGCUGAUUAAGGAGAACAUGCACAUGA<br>AGCUGUACAUGGAGGGCACCGUGGACAACCAUCA<br>CUUCAAGUGCACAUCCGAGGGCGAAGGCAAGCCC<br>UACGAGGGCACCCAGACCAUGAGAAUCAAGGUGG<br>UCGAGGGCGGCCCUCUCCCCUUCGCCUUCGACAUC<br>CUGGCUACUAGCUUCCUCUACGGCAGCAAGACCU<br>UCAUCAACCACACCCAGGGCAUCCCCGACUUCUUC<br>AAGCAGUCCUUCCCUGAGGGCUUCACAUGGGAGA<br>GAGUCACCACAUACGAAGACGGGGGCGUGCUGAC<br>CGCUACCCAGGACACCAGCCUCCAGGACGGCUGCC<br>UCAUCUACAACGUCAAGAUCAGAGGGGUGAACUU<br>CACAUCCAACGGCCCUGUGAUGCAGAAGAAAACA<br>CUCGGCUGGGAGGCCUUCACCGAGACGCUGUACC<br>CCGCUGACGGCGGCCUGGAAGGCAGAAACGACAU<br>GGCCCUGAAGCUCGUGGGCGGGAGCCAUCUGAUC<br>GCAAACAUCAAGACCACAUAUAGAUCCAAGAAAC<br>CCGCUAAGAACCUCAAGAUGCCUGGCGUCUACUA<br>UGUGGACUACAGACUGGAAAGAAUCAAGGAGGCC<br>AACAACGAGACCUACGUCGAGCAGCACGAGGUGG<br>CAGUGGCCAGAUACUGCGACCUCCCUAGCAAACU<br>GGGGCACAGAUCUCAUAUGCAUCUCGAGUGAUAG<br>UCUAGACCUUCUGCGGGGCUUGCCUUCUGGCCAU<br>GCCCUUCUUCUCUCCCUUGCACCUGUACCUCUUGG<br>UCUUUGAAUAAAGCCUGAGUAGGAAAAAAAAAAA<br>AAAAAAAAAAAAAAAAAAAAAAAAAAAAAAAAA<br>AAAAAAAAAAAAAAAAAAAAAAAAAAAAAAAAA<br>AAAAAAAAAAAAAAAAAAAAAAAAAAAAAAAAA<br>AAAAAAAAAA | 51 |
| hsa-miR-490-5p | GGUUCCUUAAUCGCGGAUCCACCCACCUGGAGAU<br>CCAUGGAGAUCAAACACCGGUCGCCACCAUGGGA<br>UCCAGCGAGCUGAUUAAGGAGAACAUGCACAUGA<br>AGCUGUACAUGGAGGGCACCGUGGACAACCAUCA<br>CUUCAAGUGCACAUCCGAGGGCGAAGGCAAGCCC<br>UACGAGGGCACCCAGACCAUGAGAAUCAAGGUGG<br>UCGAGGGCGGCCCUCUCCCCUUCGCCUUCGACAUC<br>CUGGCUACUAGCUUCCUCUACGGCAGCAAGACCU<br>UCAUCAACCACACCCAGGGCAUCCCCGACUUCUUC<br>AAGCAGUCCUUCCCUGAGGGCUUCACAUGGGAGA<br>GAGUCACCACAUACGAAGACGGGGGCGUGCUGAC<br>CGCUACCCAGGACACCAGCCUCCAGGACGGCUGCC<br>UCAUCUACAACGUCAAGAUCAGAGGGGUGAACUU<br>CACAUCCAACGGCCCUGUGAUGCAGAAGAAAACA<br>CUCGGCUGGGAGGCCUUCACCGAGACGCUGUACC<br>CCGCUGACGGCGGCCUGGAAGGCAGAAACGACAU<br>GGCCCUGAAGCUCGUGGGCGGGAGCCAUCUGAUC<br>GCAAACAUCAAGACCACAUAUAGAUCCAAGAAAC<br>CCGCUAAGAACCUCAAGAUGCCUGGCGUCUACUA<br>UGUGGACUACAGACUGGAAAGAAUCAAGGAGGCC<br>AACAACGAGACCUACGUCGAGCAGCACGAGGUGG<br>CAGUGGCCAGAUACUGCGACCUCCCUAGCAAACU<br>GGGGCACAGAUCUCAUAUGCAUCUCGAGUGAUAG<br>UCUAGACCUUCUGCGGGGCUUGCCUUCUGGCCAU<br>GCCCUUCUUCUCUCCCUUGCACCUGUACCUCUUGG<br>UCUUUGAAUAAAGCCUGAGUAGGAAAAAAAAAAA<br>AAAAAAAAAAAAAAAAAAAAAAAAAAAAAAAAA<br>AAAAAAAAAAAAAAAAAAAAAAAAAAAAAAAAA<br>AAAAAAAAAAAAAAAAAAAAAAAAAAAAAAAAA<br>AAAAAAAAAA | 52 |
| hsa-miR-499a-5p | GGUUCCUUAAUCGCGGAUCCAAACAUCACUGCAA<br>GUCUUAAAGAUCAACACCGGUCGCCACCAUGGGA<br>UCCAGCGAGCUGAUUAAGGAGAACAUGCACAUGA<br>AGCUGUACAUGGAGGGCACCGUGGACAACCAUCA<br>CUUCAAGUGCACAUCCGAGGGCGAAGGCAAGCCC<br>UACGAGGGCACCCAGACCAUGAGAAUCAAGGUGG<br>UCGAGGGCGGCCCUCUCCCCUUCGCCUUCGACAUC<br>CUGGCUACUAGCUUCCUCUACGGCAGCAAGACCU<br>UCAUCAACCACACCCAGGGCAUCCCCGACUUCUUC | 53 |

TABLE 5-continued miRNAs specifically expressed in cardiomyocytes and full-length miRNA-responsive mRNAs corresponding thereto

| miRNA specifically expressed in cardiomyocytes | Full length of miRNA-responsive mRNA | SEQ ID NO: |
|---|---|---|
| | AAGCAGUCCUUCCCUGAGGGCUUCACAUGGGAGA GAGUCACCACAUACGAAGACGGGGGCGUGCUGAC CGCUACCCAGGACACCAGCCUCCAGGACGGCUGCC UCAUCUACAACGUCAAGAUCAGAGGGGUGAACUU CACAUCCAACGGCCCUGUGAUGCAGAAGAAAACA CUCGGCUGGGAGGCCUUCACCGAGACGCUGUACC CCGCUGACGGCGGCCUGGAAGGCAGAAACGACAU GGCCCUGAAGCUCGUGGGCGGGAGCCAUCUGAUC GCAAACAUCAAGACCACAUAUAGAUCCAAGAAAC CCGCUAAGAACCUCAAGAUGCCUGGCGUCUACUA UGUGGACUACAGACUGGAAAGAAUCAAGGAGGCC AACAACGAGACCUACGUCGAGCAGCACGAGGUGG CAGUGGCCAGAUACUGCGACCUCCCUAGCAAACU GGGGCACAGAUCUCAUAUGCAUCUCGAGUGAUAG UCUAGACCUUCUGCGGGGCUUGCCUUCUGGCCAU GCCCUUCUUCUCUCCCUUGCACCUGUACCUCUUGG UCUUUGAAUAAAGCCUGAGUAGGAAAAAAAAAAA AAAAAAAAAAAAAAAAAAAAAAAAAAAAAA AAAAAAAAAAAAAAAAAAAAAAAAAAAAAA AAAAAAAAAAAAAAAAAAAAAAAAAAAAAA AAAAAAAAA | |
| hsa-miR-1271-5p | GGUUCCUUAAUCGCGGAUCCUGAGUGCUUGCUAG GUGCCAAGAGAUCACACCGGUCGCCACCAUGGGA UCCAGCGAGCUGAUUAAGGAGAACAUGCACAUGA AGCUGUACAUGGAGGGCACCGUGGACAACCAUCA CUUCAAGUGCACAUCCGAGGGCGAAGGCAAGCCC UACGAGGGCACCCAGACCAUGAGAAUCAAGGUGG UCGAGGGCGGCCCUCUCCCCUUCGCCUUCGACAUC CUGGCUACUAGCUUCCUCUACGGCAGCAAGACCU UCAUCAACCACACCCAGGGCAUCCCCGACUUCUUC AAGCAGUCCUUCCCUGAGGGCUUCACAUGGGAGA GAGUCACCACAUACGAAGACGGGGGCGUGCUGAC CGCUACCCAGGACACCAGCCUCCAGGACGGCUGCC UCAUCUACAACGUCAAGAUCAGAGGGGUGAACUU CACAUCCAACGGCCCUGUGAUGCAGAAGAAAACA CUCGGCUGGGAGGCCUUCACCGAGACGCUGUACC CCGCUGACGGCGGCCUGGAAGGCAGAAACGACAU GGCCCUGAAGCUCGUGGGCGGGAGCCAUCUGAUC GCAAACAUCAAGACCACAUAUAGAUCCAAGAAAC CCGCUAAGAACCUCAAGAUGCCUGGCGUCUACUA UGUGGACUACAGACUGGAAAGAAUCAAGGAGGCC AACAACGAGACCUACGUCGAGCAGCACGAGGUGG CAGUGGCCAGAUACUGCGACCUCCCUAGCAAACU GGGGCACAGAUCUCAUAUGCAUCUCGAGUGAUAG UCUAGACCUUCUGCGGGGCUUGCCUUCUGGCCAU GCCCUUCUUCUCUCCCUUGCACCUGUACCUCUUGG UCUUUGAAUAAAGCCUGAGUAGGAAAAAAAAAAA AAAAAAAAAAAAAAAAAAAAAAAAAAAAAA AAAAAAAAAAAAAAAAAAAAAAAAAAAAAA AAAAAAAAAAAAAAAAAAAAAAAAAAAAAA AAAAAAAAA | 54 |
| hsa-miR-3907 | GGUUCCUUAAUCGCGGAUCCUGUGAGCCAGCCUG GAGCACCUAGAUCACACCGGUCGCCACCAUGGGA UCCAGCGAGCUGAUUAAGGAGAACAUGCACAUGA AGCUGUACAUGGAGGGCACCGUGGACAACCAUCA CUUCAAGUGCACAUCCGAGGGCGAAGGCAAGCCC UACGAGGGCACCCAGACCAUGAGAAUCAAGGUGG UCGAGGGCGGCCCUCUCCCCUUCGCCUUCGACAUC CUGGCUACUAGCUUCCUCUACGGCAGCAAGACCU UCAUCAACCACACCCAGGGCAUCCCCGACUUCUUC AAGCAGUCCUUCCCUGAGGGCUUCACAUGGGAGA GAGUCACCACAUACGAAGACGGGGGCGUGCUGAC CGCUACCCAGGACACCAGCCUCCAGGACGGCUGCC UCAUCUACAACGUCAAGAUCAGAGGGGUGAACUU CACAUCCAACGGCCCUGUGAUGCAGAAGAAAACA CUCGGCUGGGAGGCCUUCACCGAGACGCUGUACC CCGCUGACGGCGGCCUGGAAGGCAGAAACGACAU GGCCCUGAAGCUCGUGGGCGGGAGCCAUCUGAUC GCAAACAUCAAGACCACAUAUAGAUCCAAGAAAC CCGCUAAGAACCUCAAGAUGCCUGGCGUCUACUA | 55 |

TABLE 5-continued miRNAs specifically expressed in cardiomyocytes and full-length miRNA-responsive mRNAs corresponding thereto

| miRNA specifically expressed in cardiomyocytes | Full length of miRNA-responsive mRNA | SEQ ID NO: |
|---|---|---|
| | UGUGGACUACAGACUGGAAAGAAUCAAGGAGGCC<br>AACAACGAGACCUACGUCGAGCAGCACGAGGUGG<br>CAGUGGCCAGAUACUGCGACCUCCCUAGCAAACU<br>GGGGCACAGAUCUCAUAUGCAUCUCGAGUGAUAG<br>UCUAGACCUUCUGCGGGGCUUGCCUUCUGGCCAU<br>GCCCUUCUUCUCUCCCUUGCACCUGUACCUCUUGG<br>UCUUUGAAUAAAGCCUGAGUAGGAAAAAAAAAA<br>AAAAAAAAAAAAAAAAAAAAAAAAAAAAAA<br>AAAAAAAAAAAAAAAAAAAAAAAAAAAAAA<br>AAAAAAAAAAAAAAAAAAAAAAAAAAAAAA<br>AAAAAAAAAA | |
| hsa-miR-4324 | GGUUCCUUAAUCGCGGAUCCUUAAGGUUAGGGUC<br>UCAGGGAGAUCAAACACCGGUCGCCACCAUGGGA<br>UCCAGCGAGCUGAUUAAGGAGAACAUGCACAUGA<br>AGCUGUACAUGGAGGGCACCGUGGACAACCAUCA<br>CUUCAAGUGCACAUCCGAGGGCGAAGGCAAGCCC<br>UACGAGGGCACCCAGACCAUGAGAAUCAAGGUGG<br>UCGAGGGCGGCCCUCUCCCCUUCGCCUUCGACAUC<br>CUGGCUACUAGCUUCCUCUACGGCAGCAAGACCU<br>UCAUCAACCACACCCAGGGCAUCCCCGACUUCUUC<br>AAGCAGUCCUUCCCUGAGGGCUUCACAUGGGAGA<br>GAGUCACCACAUACGAAGACGGGGGCGUGCUGAC<br>CGCUACCCAGGACACCAGCCUCCAGGACGGCUGCC<br>UCAUCUACAACGUCAAGAUCAGAGGGGUGAACUU<br>CACAUCCAACGGCCCUGUGAUGCAGAAGAAAACA<br>CUCGGCUGGGAGGCCUUCACCGAGACGCUGUACC<br>CCGCUGACGGCGGCCUGGAAGGCAGAAACGACAU<br>GGCCCUGAAGCUCGUGGGCGGGAGCCAUCUGAUC<br>GCAAACAUCAAGACCACAUAUAGAUCCAAGAAAC<br>CCGCUAAGAACCUCAAGAUGCCUGGCGUCUACUA<br>UGUGGACUACAGACUGGAAAGAAUCAAGGAGGCC<br>AACAACGAGACCUACGUCGAGCAGCACGAGGUGG<br>CAGUGGCCAGAUACUGCGACCUCCCUAGCAAACU<br>GGGGCACAGAUCUCAUAUGCAUCUCGAGUGAUAG<br>UCUAGACCUUCUGCGGGGCUUGCCUUCUGGCCAU<br>GCCCUUCUUCUCUCCCUUGCACCUGUACCUCUUGG<br>UCUUUGAAUAAAGCCUGAGUAGGAAAAAAAAAA<br>AAAAAAAAAAAAAAAAAAAAAAAAAAAAAA<br>AAAAAAAAAAAAAAAAAAAAAAAAAAAAAA<br>AAAAAAAAAAAAAAAAAAAAAAAAAAAAAA<br>AAAAAAAAAA | 56 |
| hsa-let-7e-5p | GGUUCCUUAAUCGCGGAUCCAACUAUACAACCUC<br>CUACCUCAAGAUCACACCGGUCGCCACCAUGGGA<br>UCCAGCGAGCUGAUUAAGGAGAACAUGCACAUGA<br>AGCUGUACAUGGAGGGCACCGUGGACAACCAUCA<br>CUUCAAGUGCACAUCCGAGGGCGAAGGCAAGCCC<br>UACGAGGGCACCCAGACCAUGAGAAUCAAGGUGG<br>UCGAGGGCGGCCCUCUCCCCUUCGCCUUCGACAUC<br>CUGGCUACUAGCUUCCUCUACGGCAGCAAGACCU<br>UCAUCAACCACACCCAGGGCAUCCCCGACUUCUUC<br>AAGCAGUCCUUCCCUGAGGGCUUCACAUGGGAGA<br>GAGUCACCACAUACGAAGACGGGGGCGUGCUGAC<br>CGCUACCCAGGACACCAGCCUCCAGGACGGCUGCC<br>UCAUCUACAACGUCAAGAUCAGAGGGGUGAACUU<br>CACAUCCAACGGCCCUGUGAUGCAGAAGAAAACA<br>CUCGGCUGGGAGGCCUUCACCGAGACGCUGUACC<br>CCGCUGACGGCGGCCUGGAAGGCAGAAACGACAU<br>GGCCCUGAAGCUCGUGGGCGGGAGCCAUCUGAUC<br>GCAAACAUCAAGACCACAUAUAGAUCCAAGAAAC<br>CCGCUAAGAACCUCAAGAUGCCUGGCGUCUACUA<br>UGUGGACUACAGACUGGAAAGAAUCAAGGAGGCC<br>AACAACGAGACCUACGUCGAGCAGCACGAGGUGG<br>CAGUGGCCAGAUACUGCGACCUCCCUAGCAAACU<br>GGGGCACAGAUCUCAUAUGCAUCUCGAGUGAUAG<br>UCUAGACCUUCUGCGGGGCUUGCCUUCUGGCCAU<br>GCCCUUCUUCUCUCCCUUGCACCUGUACCUCUUGG<br>UCUUUGAAUAAAGCCUGAGUAGGAAAAAAAAAA<br>AAAAAAAAAAAAAAAAAAAAAAAAAAAAAA | 57 |

TABLE 5-continued miRNAs specifically expressed in cardiomyocytes and full-length miRNA-responsive mRNAs corresponding thereto

| miRNA specifically expressed in cardiomyocytes | Full length of miRNA-responsive mRNA | SEQ ID NO: |
|---|---|---|
| | AAAAAAAAAAAAAAAAAAAAAAAAAAAAAAAAA<br>AAAAAAAAAAAAAAAAAAAAAAAAAAAAAAAAA<br>AAAAAAAAAA | |
| hsa-miR-208b | GGUUCCUUAAUCGCGGAUCCACAAACCUUUUGUU<br>CGUCUUAUAGAUCACACCGGUCGCCACCAUGGGA<br>UCCAGCGAGCUGAUUAAGGAGAACAUGCACAUGA<br>AGCUGUACAUGGAGGGCACCGUGGACAACCAUCA<br>CUUCAAGUGCACAUCCGAGGGCGAAGGCAAGCCC<br>UACGAGGGCACCCAGACCAUGAGAAUCAAGGUGG<br>UCGAGGGCGGCCCUCUCCCCUUCGCCUUCGACAUC<br>CUGGCUACUAGCUUCCUCUACGGCAGCAAGACCU<br>UCAUCAACCACACCCAGGGCAUCCCCGACUUCUUC<br>AAGCAGUCCUUCCCUGAGGGCUUCACAUGGGAGA<br>GAGUCACCACAUACGAAGACGGGGGCGUGCUGAC<br>CGCUACCCAGGACACCAGCCUCCAGGACGGCUGCC<br>UCAUCUACAACGUCAAGAUCAGAGGGGUGAACUU<br>CACAUCCAACGGCCCUGUGAUGCAGAAGAAAACA<br>CUCGGCUGGGAGGCCUUCACCGAGACGCUGUACC<br>CCGCUGACGGCGGCCUGGAAGGCAGAAACGACAU<br>GGCCCUGAAGCUCGUGGGCGGGAGCCAUCUGAUC<br>GCAAACAUCAAGACCACAUAUAGAUCCAAGAAAC<br>CCGCUAAGAACCUCAAGAUGCCUGGCGUCUACUA<br>UGUGGACUACAGACUGGAAAGAAUCAAGGAGGCC<br>AACAACGAGACCUACGUCGAGCAGCACGAGGUGG<br>CAGUGGCCAGAUACUGCGACCUCCCUAGCAAACU<br>GGGGCACAGAUCUCAUAUGCAUCUCGAGUGAUAG<br>UCUAGACCUUCUGCGGGGCUUGCCUUCUGGCCAU<br>GCCCUUCUUCUCUCCCUUGCACCUGUACCUCUUGG<br>UCUUUGAAUAAAGCCUGAGUAGGAAAAAAAAAAA<br>AAAAAAAAAAAAAAAAAAAAAAAAAAAAAAAAA<br>AAAAAAAAAAAAAAAAAAAAAAAAAAAAAAAAA<br>AAAAAAAAAAAAAAAAAAAAAAAAAAAAAAAAA<br>AAAAAAAAAA | 68 |

In the present invention, when a suicide gene (e.g., Bim) is used as a marker gene, for example, the following sequence can be adopted as miRNA-responsive mRNA in the present invention.

TABLE 6 mRNA_miR-1-HsBimEL

| miRNA-responsive mRNA | Sequence | SEQ ID NO: |
|---|---|---|
| mRNA_miR-1-HsBimEL | GGUUCCUUAAUCGCGGAUCCAUACAUACUUCUUU<br>ACAUUCCAAGAUCACACCGGUCGCCACCAUGGCA<br>AAGCAACCUUCUGAUGUAAGUUCUGAGUGUGACC<br>GAGAAGGUAGACAAUUGCAGCCUGCGGAGAGGCC<br>UCCCCAGCUCAGACCUGGGGCCCCUACCUCCCUAC<br>AGACAGAGCCACAAGGUAAUCCUGAAGGCAAUCA<br>CGGAGGUGAAGGGGACAGCUGCCCCACGGCAGC<br>CCUCAGGGCCCGCUGGCCCCACCUGCCAGCCCUGG<br>CCCUUUUGCUACCAGAUCCCCGCUUUUCAUCUUU<br>AUGAAGAAUCCUCCCUGCUGUCUCGAUCCUCCA<br>GUGGGUAUUUCUCUUUUGACACAGACAGGAGCCC<br>AGCACCCAUGAGUUGUGACAAAUCAACACAAACC<br>CCAAGUCCUCCUUGCCAGGCCUUCAACCACUAUCU<br>CAGUGCAAUGGCUUCCAUGAGGCAGGCUGAACCU<br>GCAGAUAUGCGCCCAGAGAUAUGGAUCGCCCAAG<br>AGUUGCGGCGUAUCGGAGACGAGUUUAACGCUUA<br>CUAUGCAAGGAGGGUAUUUUGAAUAAUUACCAA<br>GCAGCCGAAGACCACCCACGAAUGGUUAUCUUAC<br>GACUGUUACGUUACAUUGUCCGCCUGGUGUGGAG<br>AAUGCAUUGAUUCUAGACCUUCUGCGGGGCUUGC | 58 |

TABLE 6-continued mRNA_miR-1-HsBimEL

| miRNA-responsive mRNA | Sequence | SEQ ID NO: |
|---|---|---|
| | CUUCUGGCCAUGCCCUUCUUCUCUCCCUUGCACCU<br>GUACCUCUUGGUCUUUGAAUAAAGCCUGAGUAGG<br>AAAAAAAAAAAAAAAAAAAAAAAAAAAAAAAAA<br>AAAAAAAAAAAAAAAAAAAAAAAAAAAAAAAAA<br>AAAAAAAAAAAAAAAAAAAAAAAAAAAAAAAAA<br>AAAAAAAAAAAAAAAAAAAA | |

After the sequence of the miRNA-responsive mRNA has been determined as described above, a person skilled in the art is able to synthesize the miRNA-responsive reporter mRNA according to an any given existing genetic engineering method. In particular, the miRNA-responsive reporter mRNA can be obtained according to an in vitro synthesis method, using template DNA comprising a promoter sequence as a template.

It is to be noted that, before the sorting method according to the present embodiment is carried out, a screening step may be carried out to examine the effectiveness of the sorting. Specifically, as given above, multiple types of miRNA-responsive mRNAs each having 5'-UTR, which can be candidates, are produced, and then, each miRNA-responsive mRNA is introduced into a cardiomyocyte group whose purity has been already known, and thereafter, the target sequence of miRNA and miRNA-responsive mRNA, which have high effectiveness in selecting, can be determined. Such a step will be described in detail also in Example 3.

There is a case in which only one type of miRNA-responsive mRNA is used, or there is another case in which two or more types of, for example, three types, four types, five types, six types, seven types, or eight types or more of miRNA-responsive mRNAs are used. For example, in the case of using two or more types of miRNA-responsive mRNAs, it is desirable that both miRNA target sequences and marker genes comprised in individual miRNA-responsive mRNAs be different from one another. In addition, in the case of using two or more types of miRNA-responsive mRNAs, the number of miRNA target sequences comprised in the miRNA-responsive mRNA, the distance of the miRNA target sequence from the 5'-terminus, and other structural characteristics of the miRNA-responsive mRNA may be the same or different among individual miRNA-responsive mRNAs. Otherwise, it is also possible to use miRNA-responsive mRNAs, in which their miRNA target sequences are identical to each other but their marker genes are different from each other. For example, it is possible to use miRNA-responsive mRNAs, in which apoptosis-inducing genes that transduce signals through different pathways, such as Fas and Bim, are combined with an identical miRNA target sequence. In this case, it can be anticipated that undesired cells (cells other than cardiomyocytes) are efficiently removed.

In the present invention, in the case of using a plurality of miRNA-responsive mRNAs, for example, mRNA comprising BFP as a marker gene, as shown in the above Table 5, can be used in combination with mRNA comprising Keima-Red as a marker gene, as shown in the following Table 7.

TABLE 7 mRNA_miR-208a-3p_hdKeima-Red and
mRNA_miR-499a-5p_hdKeima-Red

| miRNA-responsive mRNA | Sequence | SEQ ID NO: |
|---|---|---|
| mRNA_miR-208a-3p_hdKeima-Red | GGUUCCUUAAUCGCGGAUCCACAAGCUUUUUGCU CGUCUUAUAGAUCACACCGGUCGCCACCAUGGUG AGCGUGAUCGCCAAGCAGAUGACCUACAAGGUGU ACAUGUCCGGCACCGUGAACGGCCACUACUUCGA GGUGGAGGGCGACGGCAAGGGCAAGCCCUACGAG GGCGAGCAGACCGUGAAGCUGACCGUGACCAAGG GCGGCCCCCUGCCCUUCGCCUGGGACAUCCUGUCC CCCCUGUUCCAGUACGGCAGCAUCCCCUUCACCAA GUACCCCGAGGACAUCCCCGACUACGUGAAGCAG AGCUUCCCCGAGGGCUACACCUGGGAGAGGACCA UGAACUUCGAGGACGGCGCCGUGUGCACCGUGAG CAACGACUCCAGCAUCCAGGGCAACUGCUUCAUC UACAACGUGAAGAUCAGCGGCACCAACUUCCCCC CCAACGGCCCCGUGAUGCAGAAGAAGACCCAGGG CUGGGAGCCCAGCACCGAGAGGCUGUUCGCCAGG GACGGAAUGCUGAUCGGCAACGACUACAUGGCCC UGAAGCUGGAGGGCGGCGGCCACUACCUGUGCGA GUUCAAGUCCACCUACAAGGCCAAGAAGCCCGUG AGGAUGCCCGGCUACCACUACAUCGACAGGAAGC UGGACGUGACCAGCCACAACAGGGACUACACCUC CGUGGAGCAGUGCGAGAUCGCCAUCGCCAGGCAC AGCCUGCUGGGCGGCAGCAGCGGCGGAUCCGGUG AUGAAGUCGAAGGAGUGGAAGAAGUAGCUAAGAA GAAGAGUAAAAAGGAAAAGGAUAAAAAGUAAAUA GUCUAGACCUUCUGCGGGGCUUGCCUUCUGGCCA UGCCCUUCUUCUCUCCCUUGCACCUGUACCUCUUG GUCUUUGAAUAAAGCCUGAGUAGGAAAAAAAAAA AAAAAAAAAAAAAAAAAAAAAAAAAAAAAAAA AAAAAAAAAAAAAAAAAAAAAAAAAAAAAAAA AAAAAAAAAAAAAAAAAAAAAAAAAAAAAAAA AAAAAAAAAA | 59 |
| mRNA_miR-499a-5p_hdKeima-Red | GGUUCCUUAAUCGCGGAUCCAAACAUCACUGCAA GUCUUAAAGAUCAACACCGGUCGCCACCAUGGUG AGCGUGAUCGCCAAGCAGAUGACCUACAAGGUGU ACAUGUCCGGCACCGUGAACGGCCACUACUUCGA GGUGGAGGGCGACGGCAAGGGCAAGCCCUACGAG GGCGAGCAGACCGUGAAGCUGACCGUGACCAAGG GCGGCCCCCUGCCCUUCGCCUGGGACAUCCUGUCC CCCCUGUUCCAGUACGGCAGCAUCCCCUUCACCAA GUACCCCGAGGACAUCCCCGACUACGUGAAGCAG AGCUUCCCCGAGGGCUACACCUGGGAGAGGACCA UGAACUUCGAGGACGGCGCCGUGUGCACCGUGAG CAACGACUCCAGCAUCCAGGGCAACUGCUUCAUC UACAACGUGAAGAUCAGCGGCACCAACUUCCCCC CCAACGGCCCCGUGAUGCAGAAGAAGACCCAGGG CUGGGAGCCCAGCACCGAGAGGCUGUUCGCCAGG GACGGAAUGCUGAUCGGCAACGACUACAUGGCCC UGAAGCUGGAGGGCGGCGGCCACUACCUGUGCGA GUUCAAGUCCACCUACAAGGCCAAGAAGCCCGUG AGGAUGCCCGGCUACCACUACAUCGACAGGAAGC | 60 |

TABLE 7-continued mRNA_miR-208a-3p_hdKeima-Red and
mRNA_miR-499a-5p_hdKeima-Red

| miRNA-responsive mRNA | Sequence | SEQ ID NO: |
|---|---|---|
| | UGGACGUGACCAGCCACAACAGGGACUACACCUC CGUGGAGCAGUGCGAGAUCGCCAUCGCCAGGCAC AGCCUGCUGGGCGGCAGCAGCGGCGGAUCCGGUG AUGAAGUCGAAGGAGUGGAAGAAGUAGCUAAGAA GAAGAGUAAAAAGGAAAAGGAUAAAAAGUAAUA GUCUAGACCUUCUGCGGGGCUUGCCUUCUGGCCA UGCCCUUCUUCUCUCCCUUGCACCUGUACCUCUUG GUCUUUGAAUAAAGCCUGAGUAGGAAAAAAAAA AAAAAAAAAAAAAAAAAAAAAAAAAAAAAAA AAAAAAAAAAAAAAAAAAAAAAAAAAAAAAA AAAAAAAAAAAAAAAAAAAAAAAAAAAAAAA AAAAAAAAAA | |

In the present invention, in the step of introducing miRNA-responsive mRNA into a cell group, one or more types of miRNA-responsive mRNAs are directly introduced into cells included in a cell group, by applying a lipofection method, a liposome method, an electroporation method, a calcium phosphate co-precipitation method, a DEAE dextran method, a microinjection method, a gene gun method, etc. In the case of introduction of two or more different types of miRNA-responsive mRNAs, or in the case of using miRNA-responsive mRNA and the after mentioned mRNA used as a control (hereinafter also referred to as "control mRNA"), a plurality of mRNAs are preferably co-introduced into a cell group. This is because, since the ratio of the co-introduced two or more types of mRNAs in cells is maintained in individual cells, the activity ratio of proteins expressed from these mRNAs becomes constant in a cell population. The amount of mRNA introduced at this time is different depending on a cell group into which the mRNA is introduced, the introduced mRNA, the introduction method, and the type of the introduction reagent. In order to obtain a desired translation level, a person skilled in the art can appropriately select these conditions.

In the present invention, an example of the control mRNA is mRNA consisting of a sequence comprising a nucleic acid corresponding to the coding region of a marker gene or a sequence comprising a nucleic acid corresponding to the coding region of a drug resistance gene, wherein the mRNA does not have the target site of miRNA. In a preferred embodiment, such control mRNA is introduced, together with miRNA-responsive mRNA, into a cell group, and then, it is able to function as a control for confirming and identifying cells into which the miRNA-responsive mRNA has been introduced. Moreover, the control mRNA is also able to function as a control upon quantifying the signal strength of fluorescence or luminescence from the miRNA-responsive mRNA. In order to obtain a desired translation level, the amount of the control mRNA introduced can also be selected by a person skilled in the art, as appropriate.

The "drug resistance gene" used in the present invention is not particularly limited, as long as it is a gene expressing a protein for resistance to the corresponding drug. An example of the drug resistance gene is an antibiotic resistance gene, but the example is not limited thereto. Examples of the antibiotic resistance gene include a kanamycin resistance gene, an ampicillin resistance gene, a puromycin resistance gene, a blasticidin resistance gene, a gentamicin resistance gene, a kanamycin resistance gene, a tetracycline resistance gene, and a chloramphenicol resistance gene. In the present invention, a puromycin resistance gene or a blasticidin resistance gene is preferably used as an antibiotic resistance gene.

The selecting method according to one embodiment of the present invention more preferably comprises a step of simultaneously introducing miRNA-responsive mRNA and control mRNA into a cell group comprising cardiomyocytes. Such a step can be preferably carried out by co-introduction of miRNA-responsive mRNA and control mRNA. By using control mRNA, cells, in which a low translation level of marker protein or no marker proteins are translated from miRNA-responsive mRNA, can be sorted as cardiomyocytes, even in a case in which the efficiency of introducing the miRNA-responsive mRNA into the cells is low.

In the present invention, in the case of using control mRNA, a marker gene comprised in the control mRNA is preferably different from a marker gene comprised in miRNA-responsive mRNA. For example, in a case in which the marker gene comprised in the miRNA-responsive mRNA is an apoptosis-inducing gene or a suicide gene, the marker gene comprised in the control mRNA can be a gene encoding a fluorescent protein. In this case, cells in which fluorescence is confirmed are selectively separated from other cells by sorting, for example, using FACS, and thereafter, cells in which the expression of an apoptosis-inducing gene or a suicide gene is suppressed are sorted as cardiomyocytes, so as to improve the precision of sorting. Moreover, control mRNA consisting of a sequence comprising a nucleic acid corresponding to the coding region of a drug resistance gene can be used together with miRNA-responsive mRNA consisting of a nucleic acid corresponding to the coding region of any given marker gene. In this case, regardless of the type of a marker gene, cells into which miRNA-responsive mRNA has been introduced selectively have drug resistance, and thus, it is possible to improve the precision of sorting.

On the other hand, genes of the same types can be used as both a marker gene comprised in miRNA-responsive mRNA and a marker gene comprised in control mRNA. For example, genes encoding fluorescent proteins can be used as both a marker gene comprised in miRNA-responsive mRNA and a marker gene comprised in control mRNA, and in this case, the fluorescence wavelengths of both fluorescent proteins are desirably different from each other.

Further, instead of using the genes encoding fluorescent proteins, it is also possible to use genes encoding luminescence proteins or proteins supporting fluorescence, luminescence or color development, in the same combination as described above.

The control mRNA used in the present invention is not particularly limited. The following mRNAs can be used, for example.

TABLE 8 control mRNA

| Control mRNA | Sequence | SEQ ID NO: |
|---|---|---|
| mRNA_tagBFP | GGGCGAAUUAAGAGAGAAAAGAAGAGUAAGAAG AAAUAUAAGACACCGGUCGCCACCAUGGGAUCCA GCGAGCUGAUUAAGGAGAACAUGCACAUGAAGCU GUACAUGGAGGGCACCGUGGACAACCAUCACUUC AAGUGCACAUCCGAGGGCGAAGGCAAGCCCUACG AGGGCACCCAGACCAUGAGAAUCAAGGUGGUCGA GGGCGGCCCUCUCCCCUUCGCCUUCGACAUCCUGG CUACUAGCUUCCUCUACGGCAGCAAGACCUUCAU CAACCACACCCAGGGCAUCCCCGACUUCUUCAAGC AGUCCUUCCCUGAGGGCUUCACAUGGGAGAGAGU CACCACAUACGAAGACGGGGCGUGCUGACCGCU ACCCAGGACACCAGCCUCCAGGACGGCUGCCUCAU CUACAACGUCAAGAUCAGAGGGGUGAACUUCACA UCCAACGGCCCUGUGAUGCAGAAGAAAACACUCG GCUGGGAGGCCUUCACCGAGACGCUGUACCCCGC UGACGGCGGCCUGGAAGGCAGAAACGACAUGGCC CUGAAGCUCGUGGGCGGGAGCCAUCUGAUCGCAA ACAUCAAGACCACAUAUAGAUCCAAGAAACCCGC UAAGAACCUCAAGAUGCCUGGCGUCUACUAUGUG GACUACAGACUGGAAAGAAUCAAGGAGGCCAACA ACGAGACCUACGUCGAGCAGCACGAGGUGGCAGU GGCCAGAUACUGCGACCUCCCUAGCAAACUGGGG CACAGAUCUCAUAUGCAUCUCGAGUGAUAGUCUA GACCUUCUGCGGGCUUGCCUUCUGGCCAUGCCC UUCUUCUCUCCCUUGCACCUGUACCUCUUGGUCU UUGAAUAAAGCCUGAGUAGGAAAAAAAAAAAAAA AAAAAAAAAAAAAAAAAAAAAAAAAAAAAAAAA AAAAAAAAAAAAAAAAAAAAAAAAAAAAAAAAA AAAAAAAAAAAAAAAAAAAAAAAAAAAAAAAAA AAAAAAA | 61 |
| mRNA_EGFP | GGGCGAAUUAAGAGAGAAAAGAAGAGUAAGAAG AAAUAUAAGACACCGGUCGCCACCAUGGGAUCCG UGAGCAAGGGCGAGGAGCUGUUCACCGGGGUGGU GCCCAUCCUGGUCGAGCUGGACGGCGACGUAAAC GGCCACAAGUUCAGCGUGUCCGGCGAGGGCGAGG GCGAUGCCACCUACGGCAAGCUGACCCUGAAGUU CAUCUGCACCACCGGCAAGCUGCCCGUGCCCUGGC CCACCCUCGUGACCACCCUGACCUACGGCGUGCAG UGCUUCAGCCGCUACCCCGACCACAUGAAGCAGC ACGACUUCUUCAAGUCCGCCAUGCCCGAAGGCUA CGUCCAGGAGCGCACCAUCUUCUUCAAGGACGAC GGCAACUACAAGACCCGCGCCGAGGUGAAGUUCG AGGGCGACACCCUGGUGAACCGCAUCGAGCUGAA GGGCAUCGACUUCAAGGAGGACGGCAACAUCCUG GGGCACAAGCUGGAGUACAACUACAACAGCCACA ACGUCUAUAUCAUGGCCGACAAGCAGAAGAACGG CAUCAAGGUGAACUUCAAGAUCCGCCACAACAUC GAGGACGGCAGCGUGCAGCUCGCCGACCACUACC AGCAGAACACCCCCAUCGGCGACGGCCCCGUGCUG CUGCCCGACAACCACUACCUGAGCACCCAGUCCGC CCUGAGCAAAGACCCCAACGAGAAGCGCGAUCAC AUGGUCCUGCUGGAGUUCGUGACCGCCGCCGGGA UCACUCUCGGCAUGGACGAGCUGUACAAGAGAUC UCAUAUGCAUCUCGAGUGAUAGUCUAGACCUUCU GCGGGGCUUGCCUUCUGGCCAUGCCCUUCUUCUC UCCCUUGCACCUGUACCUCUUGGUCUUUGAAUAA AGCCUGAGUAGGAAAAAAAAAAAAAAAAAAAAA AAAAAAAAAAAAAAAAAAAAAAAAAAAAAAA AAAAAAAAAAAAAAAAAAAAAAAAAAAAAAA AAAAAAAAAAAAAAAAAAAAAAAAAAAAAAA | 62 |
| mRNA_Blastcidin | GGGCGAAUUAAGAGAGAAAAGAAGAGUAAGAAGA AAUAUAAGACACCGGUCGCCACCAUGGCCAAGCCU UUGUCUCAAGAAGAAUCCACCCUCAUUGAAAGAGC AACGGCUACAAUCAACAGCAUCCCCAUCUCUGAAG ACUACAGCGUCGCCAGCGCAGCUCUCUCUAGCGAC GGCCGCAUCUUCACUGGUGUCAAUGUAUAUCAUUU UACUGGGGGACCUUGUGCAGAACUCGUGGUGCUGG GCACUGCUGCUGCUGCGGCAGCUGGCAACCUGACU | 63 |

TABLE 8-continued control mRNA

| Control mRNA | Sequence | SEQ ID NO: |
|---|---|---|
| | UGUAUCGUCGCGAUCGGAAAUGAGAACAGGGGCAU<br>CUUGAGCCCCUGCGGACGGUGCCGACAGGUGCUUC<br>UCGAUCUGCAUCCUGGGAUCAAAGCCAUAGUGAAG<br>GACAGUGAUGGACAGCCGACGGCAGUUGGGAUUCG<br>UGAAUUGCUGCCCUCUGGUUAUGUGUGGGAGGGCU<br>AAUCUAGACCUUCUGCGGGGCUUGCCUUCUGGCCA<br>UGCCCUUCUUCUCUCCCUUGCACCUGUACCUCUUG<br>GUCUUUGAAUAAAGCCUGAGUAGGAAAAAAAAAA<br>AAAAAAAAAAAAAAAAAAAAAAAAAAAAAAAA<br>AAAAAAAAAAAAAAAAAAAAAAAAAAAAAAAA<br>AAAAAAAAAAAAAAAAAAAAAAAAAAAAAAAA<br>AAAAAAAA | |
| mRNA_Puromycin | GGGCGAAUUAAGAGAGAAAAGAAGAGUAAGAAGA<br>AAUAUAAGACACCGGUCGCCACCAUGACCGAGUAC<br>AAGCCCACGGUGCGCCUCGCCACCCGCGACGACGUC<br>CCCCGGGCCGUACGCACCCUCGCCGCCGCGUUCGCC<br>GACUACCCCGCCACGCGCCACACCGUCGAUCCGGAC<br>CGCCACAUCGAGCGGGUCACCGAGCUGCAAGAACU<br>CUUCCUCACGCGCGUCGGGCUCGACAUCGGCAAGG<br>UGUGGGUCGCGGACGACGGCGCCGCGGUGGCGGUC<br>UGGACCACGCCGGAGAGCGUCGAAGCGGGGCGGU<br>GUUCGCCGAGAUCGGCCCGCGCAUGGCCGAGUUGA<br>GCGGUUCCCGGCUGGCCGCGCAGCAACAGAUGGAA<br>GGCCUCCUGGCGCCGCACCGGCCCAAGGAGCCCGCG<br>UGGUUCCUGGCCACCGUCGGCGUCUCGCCCGACCA<br>CCAGGGCAAGGGUCUGGGCAGCGCCGUCGUGCUCC<br>CCGGAGUGGAGGCGGCCGAGCGCGCCGGGGUGCCC<br>GCCUUCCUGGAGACCUCCGCGCCCCGCAACCUCCCC<br>UUCUACGAGCGGCUCGGCUUCACCGUCACCGCCGA<br>CGUCGAGGUGCCCGAAGGACCGCGCACCUGGUGCA<br>UGACCCGCAAGCCCGGUGCCUGAUCUAGACCUUCU<br>GCGGGGCUUGCCUUCUGGCCAUGCCCUUCUUCUCU<br>CCCUUGCACCUGUACCUCUUGGUCUUUGAAUAAAG<br>CCUGAGUAGGAAAAAAAAAAAAAAAAAAAAAA<br>AAAAAAAAAAAAAAAAAAAAAAAAAAAAAAAA<br>AAAAAAAAAAAAAAAAAAAAAAAAAAAAAAAA<br>AAAAAAAAAAAAAAAAAAAAAAAAAA | 64 |

According to the sorting method of one embodiment of the present invention, by performing a step of introducing miRNA-responsive mRNA, and optionally, control mRNA into a cell group, cardiomyocytes can be put into a state in which the cardiomyocytes can be sorted from the cell group possibly comprising the same. That is to say, desired cardiomyocytes can be put into a state in which the cardiomyocytes present detectable signal information that is different from those of other cell types, from the cell group comprising two or more types of cells possibly comprising cardiomyocytes. By further performing a sorting step in the below-mentioned production method, cardiomyocytes can be selectively separated.

[Method for Producing Cardiomyocytes (1)]

In one aspect of the present invention, a method involving sorting using FACS is provided. Specifically, the present invention provides a method for producing cardiomyocytes, comprising the following steps (a) and (b):
(a) a step of introducing miRNA-responsive mRNA into a cell group, and
(b) a step of sorting the cardiomyocytes based on the translation level of a protein from the miRNA-responsive mRNA of the step (a), wherein
the miRNA-responsive mRNA consists of a sequence comprising the following (i) and (ii):
(i) a nucleic acid specifically recognized by miRNA specifically expressed in cardiomyocytes, and
(ii) a nucleic acid corresponding to the coding region of a gene, wherein high-purity cardiomyocytes can be recovered compared with a case in which the steps (a) and (b) are not carried out. It is to be noted that the cardiomyocytes can be recovered by selecting cells in which the translation level of the gene in (ii) above comprised in the miRNA-responsive mRNA is smaller.

In the present invention, the step (a) can be carried out in the same manner as the introduction step explained in the above described method for sorting cardiomyocytes. Accordingly, (i) the target sequence of miRNA or the like in the configuration of miRNA-responsive mRNA is also the same as described above. In the present step, preferably, control mRNA comprising a gene encoding a fluorescent protein as a marker gene and miRNA-responsive mRNA are co-introduced into cells, or two or more types of miRNA-responsive mRNAs comprising, as marker genes, those encoding fluorescent proteins having different fluorescence wavelengths are co-introduced into cells. Thereby, the translation level of a protein from miRNA-responsive mRNA can be more precisely obtained.

The "gene" in (ii) above, which is used in the present invention, may be the same marker gene as described above. Preferably, a gene encoding a fluorescent protein can be used. The fluorescent protein is also the same as described above, and a gene encoding BFP is preferably used as a gene encoding a fluorescent protein.

The cell group of the step (a) used in the present invention may be any given cell group, and it may be, for example, a cell group induced to differentiate from pluripotent stem cells, or a cell population removed from a living body. In the present invention, it is preferably a cell group that has been subjected to a step of inducing differentiation of pluripotent stem cells into cardiomyocytes. The period, at which miRNA-responsive mRNA is introduced into a cell group that has been subjected to a step of inducing differentiation from pluripotent stem cells, is not particularly limited, as long as it is a period in which cells are intended to be sorted. In a case in which a step of inducing differentiation of the cells is carried out using the method specifically mentioned in the above described section regarding a myocardial differentiation induction method, the period is preferably the 10th to 25th day from formation of an embryoid body, and more preferably the 18th day from the embryoid body formation.

In the step (b), cardiomyocytes can be sorted using, as an indicator, the translation level of a marker protein translated from miRNA-responsive mRNA. That is to say, this step can be a step of sorting cells, in which the translation level of a marker protein translated from miRNA-responsive mRNA is low or undetectable. Such cells, in which the expression level of miRNA used as an indicator is low, can be determined by comparing the cells with cells other than cardiomyocytes, in terms of the translation level of a marker protein.

Specifically, the sorting step can be carried out by detecting signals from a marker protein that is a product translated from a marker gene, using a predetermined detector. Examples of such a detector include a flow cytometer, an imaging cytometer, a fluorescence microscope, a luminescence microscope, and a CCD camera, but the examples are not limited thereto. As such a detector, one skilled in the art can use a suitable detector depending on the type of a marker protein. For example, when the marker is a fluorescent protein or a luminescent protein, sorting can be carried out using a flow cytometer. When the marker is a protein supporting fluorescence, luminescence or color development, colored cells or the like are irradiated with light using a microscope, using a culture dish prepared by the coating of a light-responsive cell culture substrate. Cells can be sorted out by utilizing the phenomenon in which unirradiated cells are removed from the culture dish. When the marker protein is a membrane-localized protein, a method of quantifying a marker protein can be applied using a detection reagent specific to a cell surface protein, such as an antibody, and the above described detector, and further, a method of isolating cells without subjecting the cells to a process of quantifying a marker protein, using a magnetic cell separation device (MACS), can also be applied. When such a marker protein is a drug resistance gene, a method comprising detecting the expression of a marker gene by drug administration, and then isolating living cells, can be applied.

The cardiomyocytes can be obtained by the production method of the present invention at a higher purity than that obtained by an ordinary differentiation induction method that does not involve a step of sorting cells using miRNA-responsive mRNA. In the present invention, the purity of cardiomyocytes is not particularly limited, as long as it is higher than the purity obtained in the case of not subjecting cells to a sorting step of using miRNA-responsive mRNA. The purity of cardiomyocytes is preferably 60% or more, and examples of the purity include 60%, 70%, 80%, 81%, 82%, 83%, 84%, 85%, 86%, 87%, 88%, 89%, 90%, 91%, 92%, 93%, 94%, 95%, 96%, 97%, 98%, 99% and 100%. In this case, the purity means a value obtained using, as an indicator, TNT specifically expressed in cardiomyocytes. Specifically, the purity can be confirmed by adding a substance capable of being detected with a sorting device such as a flow cytometer to a cell group as a sorting target, so as to label TNT with the substance. Such a substance capable of being detected with a sorting device is not particularly limited, and an example of the substance is a combination of a primary antibody and a secondary antibody. In the present invention, confirmation of the purity using TNT as an indicator is carried out by immobilizing a cell group used as a sorting target with paraformaldehyde, then adding a primary antibody reacting with TNT to the cell group, and then adding a secondary antibody comprising a substance capable of being detected with a sorting device to the cell group. Preferably, clone 13-11 (Thermo) is used as a primary antibody reacting with TNT, and APC goat anti-mouse Ig (BD Pharmingen) is used as a secondary antibody reacting therewith. After addition of the antibodies, by applying a sorting device such as a flow cytometer, the purity can be obtained.

[Method for Producing Cardiomyocytes (2)]

In another aspect of the present invention, a method that does not need sorting using FACS is provided. Specifically, the present invention provides a method for producing cardiomyocytes, comprising the following steps (a) and (b):
(a) a step of introducing miRNA-responsive mRNA and mRNA consisting of a sequence comprising a nucleic acid corresponding to the coding region of a drug resistance gene into a cell group, and
(b) a step of culturing the cell group obtained in the step (a) in the presence of a drug corresponding to the drug resistance gene of the step (a), wherein
the miRNA-responsive mRNA consists of a sequence comprising the following (i) and (ii):
(i) a nucleic acid specifically recognized by miRNA specifically expressed in cardiomyocytes, and
(ii) a nucleic acid corresponding to the coding region of a gene, wherein
high-purity cardiomyocytes can be recovered compared with a case in which the steps (a) and (b) are not carried out.

In the present invention, the step (a) can be carried out in the same manner as the introduction step explained in the above described method for sorting cardiomyocytes. Accordingly, the target sequence of miRNA in (i) above or the like in the configuration of miRNA-responsive mRNA can also be the same as described above.

The "gene" in (ii) above, which is used in the present embodiment, may be the same marker gene as described above. Preferably, an apoptosis-inducing gene or a suicide gene can be used. The apoptosis-inducing gene and the suicide gene are also the same as described above. Preferably, Bim is used as an apoptosis-inducing gene, and HSV-TK is used as a suicide gene.

The "drug resistance gene" used in the present invention is the same as described above, and preferably, a puromycin resistance gene or a blasticidin resistance gene is used. The mRNA consisting of a sequence comprising a nucleic acid corresponding to the coding region of a drug resistance gene is control mRNA that does not have the target sequence of miRNA. In the step (a), the miRNA-responsive mRNA and the mRNA consisting of a sequence comprising a nucleic acid corresponding to the coding region of a drug resistance gene are preferably co-introduced into a cell group.

The cell group of the step (a) used in the present embodiment may be the same as the cell group of the step (a) in the method for producing cardiomyocytes (1).

The drug resistance gene of the step (a) and the drug of the step (b) corresponding thereto, which are used in the present invention, may have any given concentrations, as long as these are concentrations in which cells that do not have a drug resistance gene cannot survive when the cells are cultured in the presence of the corresponding drug. For example, when the drug resistance gene is a puromycin resistance gene, the concentration of control mRNA to be co-introduced is preferably 1 to 40 ng/ml, and examples of the concentration of control mRNA include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, and 40 ng/ml. More preferably, it is 4 ng/ml. In addition, in this case, the concentration of puromycin to be added to a medium is preferably 1 to 40 µg/ml, and examples of the concentration of puromycin include 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 11 µg/ml, 12 µg/ml, 13 µg/ml, 14 µg/ml, 15 µg/ml, 16 µg/ml, 17 µg/ml, 18 µg/ml, 19 µg/ml, 20 µg/ml, 30 µg/ml 1, and 40 µg/ml. More preferably, it is 4 µg/ml.

[Kit for Purifying Cardiomyocytes]

In another aspect, the present invention provides a kit for sorting at high purity or producing cardiomyocytes. The cardiomyocyte-purifying kit used in the present invention can be a kit comprising miRNA-responsive mRNA. The miRNA-responsive mRNA included in the kit of the present invention is not particularly limited, and miRNA-responsive OFF switch mRNA is preferably used. A specific configuration of the miRNA-responsive mRNA is as mentioned in the method for sorting cardiomyocytes and the method for producing cardiomyocytes, as described above. The kit of the present invention may comprise all combinations of the miRNA-responsive mRNA described in these methods and a plurality of miRNA-responsive mRNAs.

The kit of the present invention may further comprise control mRNA. When the present kit comprises control mRNA, a preferred combination of the miRNA-responsive mRNA and the control mRNA is as explained in the above described method for sorting cardiomyocytes. The kit of the present invention may comprise all combinations of the miRNA-responsive mRNAs, a plurality of miRNA-responsive mRNAs, and control mRNAs, which are described in the method for sorting cardiomyocytes and the method for producing cardiomyocytes, as described above. In particular, the kit for carrying out the method for producing cardiomyocytes (2) comprises control mRNA consisting of a sequence comprising a nucleic acid corresponding to the coding region of a drug resistance gene.

The kit used in the present invention may include a reagent for introducing miRNA-responsive mRNA, as well as the miRNA. In addition to these, the present kit can also comprise reagents necessary for purification of cardiomyocytes, an instruction manual for carrying out the sorting method or production method of the present invention, and the like, as appropriate.

The cell group used as a target of the kit of the present invention may be the same cell group as those described in the above described method for sorting cardiomyocytes and method for producing cardiomyocytes, or may also be induced and differentiated cells from pluripotent stem cells, or may also be a cell population removed from a living body. The kit used in the present invention can be used to sort out cardiomyocytes from a population comprising a plurality of cells, or can also be used to confirm the purity of cardiomyocytes in a certain cell population. The method for producing miRNA-responsive mRNA, and optionally, control mRNA, which are comprised in the kit, and the method for using them, are as described in the aforementioned method for sorting cardiomyocytes and method for producing cardiomyocytes.

[Therapeutic Agent for Heart Disease]

The cardiomyocytes obtained in the present invention can be used as a therapeutic agent for the heart disease of an animal (preferably, a human), directly as cardiomyocytes obtained in the sorting step, or optionally, by an ordinary method, after being subjected to a step of removing dead cells or impurities from a cell group comprising the cardiomyocytes obtained in the sorting step. As a method for treating heart disease, for example, the obtained cardiomyocytes may be suspended in normal saline or the like, and then, the suspension may be directly administered to the myocardial layer of the heart. Otherwise, the obtained cardiomyocytes may be processed into a sheet, and the sheet may be then attached to the heart of a patient. In the former case, the cells alone may be administered, and preferably, the cells may be administered together with a scaffolding material that promotes adhesion. Herein, examples of the scaffolding material include organism-derived components such as collagen, and synthetic polymers alternative for the organism-derived components, such as polylactic acid, but the examples are not limited thereto. When a myocardial sheet is administered, administration is achieved by arranging the sheet, such that it covers a desired portion. Herein, the arrangement of the sheet such that it covers a desired portion can be carried out by applying a technique that is well known in the present technical field. Upon arranging the sheet, if the desired portion is large, the sheet may be arranged such that it surrounds the tissues. In addition, upon administration, in order to obtain desired effects, the sheet may also be arranged to an identical portion several times. When the sheet is arranged several times, the arrangement is desirably carried out after a sufficient time interval, so that desired cells adhere to tissues and angiogenesis then takes place. Such a mechanism of treating heart disease may be the effect caused by adhesion of the myocardial sheet to the desired portion, or may also be an indirect action that is not dependent on such adhesion of cells (for example, the effect of mobilization of recipient-derived cells to a damaged portion by secretion of an attractant). When a myocardial sheet is used in the treatment of heart disease, the sheet may comprise cell scaffolding materials (scaffolds) such as collagen, fibronectin, laminin and the like, as well as cardiomyocytes. Alternatively, the myocardial sheet may also comprise any given types of cells (wherein multiple types of cells are possible), as well as cardiomyocytes. Examples of the heart disease that can be treated in the present invention include diseases such as heart failure, ischemic heart disease, myocardial infarction, cardiomyopathy, myocarditis, hypertrophic cardiomyopathy, dilated phase of hypertrophic cardiomyopathy and dilated cardiomyopathy, and deficits caused by disorders, but the examples are not limited thereto.

In the present invention, the number of cardiomyocytes used for the treatment of heart disease is not particularly limited, as long as the number of the cells constitutes an amount in which cardiomyocytes or a myocardial sheet to be administered can exhibit effects in the treatment of heart disease. The cardiomyocytes may be prepared, while the number of the cells is appropriately increased or decreased depending on the size of an affected area or the size of the body of a patient.

EXAMPLES

The present invention will be more specifically described in the following examples. However, these examples are not intended to limit the scope of the present invention.

Example 1

Pluripotent Stem Cells

As a 201B7 line (Takahashi K, et al. Cell. 131: 861-72, 2007), a 409B2 line, a 947A2 line, and a KhES1 line, the following lines were used.
(1) The 201B7 line was produced by the method described in Takahashi K, et al. Cell. 131: 861-72, 2007.
(2) 409B2 line Based on the method described in Okita. K, et al., Stem Cells. 2012 Nov. 29., an episomal vector (pCXLE-hOCT3/4-shp53-F, pCXLE-hSK, pCXLE-hUL) was introduced into human skin cells according to electroporation, and thereafter, the resulting cells were cultured on a mitomycin-treated mouse embryonic fibroblast feeder, so as to produce the iPS cell line. The culture was carried out by conventional methods (Takahashi K, et al. Cell. 131: 861-72, 2007 and Nakagawa M, et al. Nat Biotechnol. 26: 101-6, 2008).
(3) 947A2 line By applying the same method as that for the aforementioned 409B2 line, an iPS cell line was produced from human peripheral blood cells. For culture, the same method as that for the aforementioned 409B2 line was applied.
(4) KhES line As human ES cells, the KhES1 line established at Field of Stem Cell Research, Institute for Frontier Medical Sciences, Kyoto University was used, and the cells were cultured by a conventional method (Suemori H, et al. Biochem Biophys Res Commun. 345:926-32, 2006).

Method for Inducing Cardiomyocytes

The 201B7 cell line, 409B2 line, 947A2 line or KhES1 line was treated with CTK solution (ReproCELL) for 2 minutes, and the solution was then removed. The residue was treated with Accumax (Innovative Cell Technologies) for 5 minutes, and the resultant was then dissociated into single cells by pipetting. The cells were recovered by centrifugation and were then transferred into a low-adhesion 6-well dish (Corning), and thereafter, the cells were cultured in 1.5 ml/well STEMPRO 34 (Invitrogen), to which 2 mM L-Glutamine, 150 µg/mL Transferrin, 50 µg/mL Ascorbic Acid (sigma), $4 \times 10^{-4}$ M monothioglycerol (MTG) and 2 ng/mL BMP4 (R & D) had been added, under conditions of 37° C. and 5% oxygen, so as to form EB (day 0).

On the following day (day 1), STEMPRO34, to which 1% L-Glutamine, 150 µg/mL Transferrin, 50 µg/mL Ascorbic Acid, $4 \times 10^4$ M MTG, 18 ng/mL BMP4, 10 ng/mL bFGF and 12 ng/mL Activin A had been added, was added in an equal amount to the 6-well plate in which the culture of EB was carrying out, and the obtained mixture was then cultured under conditions of 37° C. and 5% oxygen for 3 days.

Subsequently (day 4), the obtained EB was washed with IMDM (Invitrogen), and STEMPRO 34, to which 1% L-Glutamine, 150 µg/mL Transferrin, 50 µg/mL Ascorbic Acid, $4 \times 10^4$ M MTG, 10 ng/mL VEGF and 1 µM IWP-3 had been added, was added to the dish. The obtained mixture was cultured under conditions of 37° C. and 5% oxygen for 4 days.

Thereafter (day 8), the medium was exchanged with STEMPRO 34, to which 1% L-Glutamine, 150 µg/mL Transferrin, 50 µg/mL Ascorbic Acid, $4 \times 10^4$ M MTG, 10 ng/mL VEGF and 5 ng/mL bFGF had been added, and the obtained mixture was then cultured under conditions of 37° C. and 5% oxygen for 4 days. During the culture, the medium was replaced with fresh medium with the same conditions as those described above, once in two days.

Thereafter (day 12), the resultant was transferred into an incubator having an ordinary oxygen concentration, and it was then cultured for 8 days. During the culture, the medium was replaced with fresh medium with the same conditions as those described above, once in two days.

Example 2

Screening for Candidate Substance for Cardiomyocyte-Specific miRNA (1) Sorting of Cardiomyocytes Using MYH6-EIP4 First, an iPS cell line, into which an EGFP cassette operably binding to an MYH6 promoter (MYH6-EIP4) had been introduced, was produced. The MYH6-EIP4-introduced iPS cell line was produced by introducing a vector, in which an EGFP cassette had been operably bound to a site downstream of a MYH (myosin heavy chain)-promoter, into 201B7 using a PiggyBac transposon system. In order to induce differentiation of the cells into cardiomyocytes, the obtained MYH6-EIP4-introduced iPS cell line was cultured in STEMPRO 34 (Invitrogen), to which 1% L-Glutamine, 150 pig/mL Transferrin, 50 µg/mL Ascorbic Acid (sigma), $4 \times 10^{-4}$ M monothioglycerol (MTG), 10 uM Rock inhibitor, 0.5% Matrigel and 2 ng/mL BMP4 (R & D) had been added, under conditions of 37° C. and 5% oxygen, thereby forming EB (day 0). Thereafter, the cells were induced to differentiate into cardiomyocytes by the same method as the method for inducing the cells to differentiate into cardiomyocytes applied in Example 1. The cells were analyzed on the 8th day after initiation of the culture. As a result, EGFP-positive cells were observed. These results suggested that cells that had differentiated into cardiomyocytes were present at this stage (data not shown).

On the 8th and 20th days after initiation of the culture, the cells were recovered, and were then divided into EGFP-positive cells and EGFP-negative cells, using FACS. Briefly, the cell populations (EB) recovered on the 8th and 20th days were treated with collagenase type I for 1 hour, and then with trypsin for 5 to 10 minutes. Thereafter, 50% FBS/IMDM was added to the resulting cells to neutralize trypsin, and the EB was gently agitated by pipetting, so that the cells were dissociated. Thereafter, the cells were centrifuged at 1000 rpm for 5 minutes, and were then re-suspended in PBS to which 2% FBS had been added. The cells were sorted using FACS Arial II cell sorter (BD Biosciences), and thereafter, the expression of Troponin T (TNT) was analyzed.

As a result, it was found that a majority of EGFP-positive cells, which had been sorted on the 8th and 20th days, expressed TNT that is a myocardium-specific marker (data not shown).

(2) miRNA Microarray Analysis

Subsequently, in order to compare the EGFP-positive cells and the EGFP-negative cells, which had been each sorted on the 8th day and the 20th day, in terms of the expression profile of miRNA, a miRNA microarray analysis was carried out. Briefly, the EGFP-positive cells and the EGFP-negative cells, which had been each sorted on the 8th day and the 20th day, were dissolved using QIAzol lysis reagent (Qiagen) in accordance with manufacturer's instructions, and thereafter, total RNA was purified using miRNA Mini Kit. The A260/280 ratio was measured using Nanodrop instrument (Thermo Scientific), so that the total RNA concentration and purity were determined. For the microarray, the RNA amount was confirmed using 2100 Bioanalyzer (Agilent Technologies). Subsequently, using Agilent Technologies human miRNA microarray release 19.0, the expression profiling of miRNA was carried out in accordance with the protocols of the manufacturer. The obtained data were analyzed using GeneSpring GX 12.6 software program, and 46064 technology version was selected.

Figure 1B:
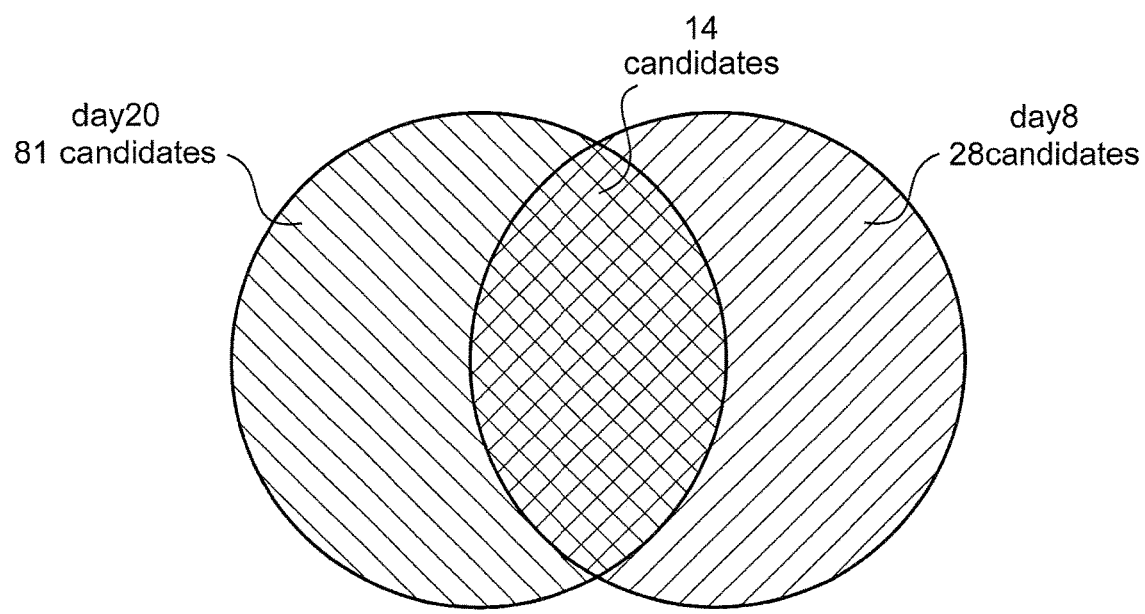

As a result, 28 miRNAs, of which expression was higher in the EGFP-positive cells than in the EGFP-negative cells, were found on the 8th day, and the same 81 miRNAs as described above were found on the 20th day, and further, 14 miRNAs whose expression level was high on both the 8th and 20th days were identified (FIG. 1 and Table 2).

(3) Production of miRNA-Responsive OFF Switch mRNA

A list of primer sequences used for constructing individual structural components of miRNA-responsive OFF switch mRNA is shown in the following table. The symbol "fwd" indicates a forward primer, and "rev" indicates a reverse primer.

TABLE 9

| Name of primer | Sequence (5' → 3') | SEQ ID NO: |
|---|---|---|
| tagBFP fwd | CACCGGTCGCCACCATGGGATCCAGCGAG | 69 |
| TAPEGFP_IVTfwd | CACCGGTCGCCACCATGGGATCCGTGAGCAAGGGC | 70 |
| TAP_IVTrev | GCCCCGCAGAAGGTCTAGACTATCACTCGAGATGCATATGAGATC | 71 |
| hdKeimaRed_IVTfwd | CACCGGTCGCCACCATGGTGAGCGTGATCGCCAAG | 72 |
| pNP-hdKeima-Red rev | GCCCCGCAGAAGGTCTAGACTATTACTTTTTATCCTTTTCCTTTTTACTCTTCTTC | 73 |
| TAP_T7_G3C fwd primer | CAGTGAATTGTAATACGACTCACTATAGGGC | 74 |
| Rev5UTR primer | CATGGTGGCGACCGGTGTCTTATATTTCTTCTTACTC | 75 |
| IVT_5prime_UTR | CAGTGAATTGTAATACGACTCACTATAGGGCGAATTAAGAGAGAAAAGAAGAGTAAGAAGAAATATAAGACACCGGTCGCCACCATG | 76 |
| Fwd3UTR primer | TCTAGACCTTCTGCGGGGC | 77 |
| Rev3UTR2T20 | TTTTTTTTTTTTTTTTTTTTCCTACTCAGGCTTTATTCAAAGACCAAG | 78 |
| 3UTR120A rev primer | TTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTCCTACTCAGGCTTTATTCA | 79 |
| IVT_3prime_UTR | TCTAGACCTTCTGCGGGGCTTGCCTTCTGGCCATGCCCTTCTTCTCCCTTGCACCTGTACCTCTTGGTCTTTGAATAAAGCCTGAGTAGG | 80 |
| GCT7pro_5UTR2 | GCTAATACGACTCACTATAGGTTCCTTAATCGCGGATCC | 81 |
| ORF Blastcidin Fwd | CACCGGTCGCCACCATGGCCAAGCCTTTGTC | 82 |
| ORF Blastcidin Rev | GCCCCGCAGAAGGTCTAGATTAGCCCTCCCACACATAACCAG | 83 |
| ORF Puromycin Fwd | CACCGGTCGCCACCATGACCGAGTACAAGCCCACG | 84 |
| ORF Puromycin Rev | GCCCCGCAGAAGGTCTAGATCAGGCACCGGGCTTGC | 85 |
| Clontech_IVTfwd | CACCGGTCGCCACCATG | 86 |
| BimEL_IVTrev | GCCCCGCAGAAGGTCTAGAATCAATGCATTCTCCACACCAG | 87 |

Each plasmid DNA used as a template upon production of miRNA-responsive OFF switch mRNA can be acquired or produced, as described below.

(a) pTAP-tagBFP

Using pTagBFP-Tubulin (Evrogen) as a template, and employing, as primers, TagBFP_Tfwd (5'-GCCAC-CATGGGATCCAGCGAGCTGATTAAGGAGAAC-3') (SEQ ID NO:88) and TagBFP_Trev (5'-ACTCGAGATCT-GTGCCCCAGTTTGCTAG-3') (SEQ ID NO:89), a fragment was amplified by a PCR method. The obtained fragment was inserted into a cloning vector pGEM-TAP of the inventors' own making. pGEM-TAP was produced by PCR mutagenesis using pGEM-Teasy (Promega) as a template, and employing, as primers, pGEMTAP_MCS_Rev
(SEQ ID NO: 90)
(5'-GGGATCCCATGGTGTCGACCTGCAGCATATGAGCTCCTGAATTCGC CCTATAGTGAGTCG-3')
and pGEMTAP_MCS_Fwd
(SEQ ID NO: 91)
(5'-GGGAGATCTCATATGCATCTCGAGTGATAGTCTAGACAAGCTTGAG

TATTCTATAGTGTCACC-3').

(b) pNP-hdKeima-Red pNP-hdKeima-Red was purchased from MEDICAL & BIOLOGICAL LABORATORIES CO., LTD. (MBL) (#AM-V0274).

(c) pCTp-EGFP

Using pEGFP-N1 (Clontech) as a template, and employing, as primers, YF128_EXFP_Tfwd (5'-GAAC-CATGGGATCCGTGAGCAAGGGCGAGG-3') (SEQ ID NO:92) and YF129_EXFP_Trev (5'-TATGAGATCTCTTG-TACAGCTCGTCCATG-3') (SEQ. ID NO:93), a fragment was amplified by a PCR method. The obtained fragment was inserted into a cloning vector pCM-TAP of the inventors' own making. pCM-TAP was produced by ligating a DraI fragment of the above described pGEM-TAP to a NheI-AgeI blunt-end fragment of pLysSRARE2 (Novagen).

(d) pLenti6/Ubc/V5-DEST (Blastcidin vector)

pLenti6/Ubc/V5-DEST was purchased from Life Technologies (#V499-10).

(e) pPyCAG-Nanog-IP (Puromycin vector)

As pPyCAG-Nanog-IP, Plasmid #13838 from Addgene was used.

(f) pcDNA3. I-HsBimEL pcDNA3.1-HsBimEL was obtained by the method described in Saito H, et al., Nat Commun. 18; 2: 160 (2011).

(3-1) Construction of Sequences Comprising Nucleic Acids Corresponding to Protein Coding Regions of Gene Encoding Fluorescent Protein, Apoptosis-Inducing Gene, and Drug Resistance Gene Sequences comprising nucleic acids corresponding to protein coding regions of a gene encoding a fluorescent protein, an apoptosis-inducing gene, and a drug resistance gene were constructed through PCR amplification from individual template plasmids, using the primers shown in Table 6.

(a) tagBFP

The following solution was prepared using KOD-Plus-Neo (KOD-401, TOYOBO) in accordance with manufacturer's instructions.

TABLE 10

| Structural components | Final concentration |
| --- | --- |
| 10 × kod-plus-Neo buffer | 1× |
| 2 mM dNTPs | 200 µM |
| 25 mM MgSO$_4$ aq | 1.5 mM |
| tagBFP fwd | 0.3 µM |
| TAP_IVTrev | 0.3 µM |
| pTAP-tagBFP | 1.0 ng/µL |
| 1 U/µL Kod + polymerase | 0.02 U/µL |
| D2W | |
| Final volume | 50 µL |

The prepared solution was subjected to PCR amplification under the following reaction conditions.

TABLE 11

| 94° C. | 2 minutes | |
| --- | --- | --- |
| 98° C. | 10 seconds | 20 cycles |
| 68° C. | 30 seconds | |
| 15° C. | ∞ | |

The amplified PCR product was treated using Dpn I (TOYOBO) at 37° C. for 30 minutes, and thereafter, using MiniElute PCR purification Kit (QIAGEN), the reaction product was purified in accordance with manufacturer's instructions.

(b) EGFP

PCR amplification was carried out by the same method as that in (a) above. Instead of tagBFP fwd, TAPEGFP_IVTfwd was used as a primer for PCR. In addition, instead of pTAP-tagBFP, pCTp-EGFP was used as a template.

(c) hdKeima-Red

PCR amplification was carried out by the same method as that in (a) above. Instead of tagBFP fwd and TAP_IVTrev, hdKeimaRed_IVTfwd and pNP-hdKeima-Red rev were used as primers for PCR. In addition, instead of pTAP-tagBFP, pNP-hdKeima-Red was used as a template.

(d) Bim

PCR amplification was carried out by the same method as that in (a) above. Instead of tagBFP fwd and TAP_IVTrev, Clontech_IVTfwd and BimEL_IVTrev were used as primers for PCR. In addition, instead of pTAP-tagBFP, pcDNA3.1-HsBimEL human was used as a template.

(e) Puromycin

PCR amplification was carried out by the same method as that in (a) above. Instead of tagBFP fwd and TAP_IVTrev, ORF Puromycin Fwd and ORF Puromycin Rev were used as primers for PCR. In addition, instead of pTAP-tagBFP, pPyCAG-Nanog-IP was used as a template.

(f) Blastcidin

PCR amplification was carried out by the same method as that in (a) above. Instead of tagBFP fwd and TAP_IVTrev, ORF Blastcidin Fwd and ORF Blastcidin Rev were used as primers for PCR. In addition, instead of pTAP-tagBFP, pLenti6/Ubc/V5-DEST was used as a template.

(3-2) Construction of 5'-UTR and 3'-UTR Sequences

5'-UTR and 3'-UTR sequences were constructed through PCR amplification from individual templates, using the primers shown in Table 6.

(a) 5'-UTR

The following solution was prepared using KOD-Plus-Neo (KOD-401, TOYOBO) in accordance with manufacturer's instructions.

TABLE 12

| Structural components | Final concentration |
| --- | --- |
| 10 × kod-plus-Neo buffer | 1× |
| 2 mM dNTPs | 200 μM |
| 25 mM MgSO₄ aq | 1.5 mM |
| TAP_T7_G3C fwd primer | 0.3 μM |
| Rev5UTR primer | 0.3 μM |
| IVT_5prime_UTR | 1.0 ng/μL |
| 1 U/μL Kod + polymerase | 0.02 U/μL |
| D2W | |
| Final volume | 50 μL |

The prepared solution was subjected to PCR amplification under the following reaction conditions.

TABLE 13

| | | |
| --- | --- | --- |
| 94° C. | 2 minutes | |
| 98° C. | 10 seconds | 20 cycles |
| 68° C. | 10 seconds | |
| 15° C. | ∞ | |

The amplified PCR product was purified using MiniElute PCR purification Kit (QIAGEN) in accordance with manufacturer's instructions.

(d) 3'-UTR

PCR amplification was carried out by the same method as that in (a) above. Instead of the TAP_T7_G3C fwd primer and the Rev5UTR primer, Fwd3UTR primer and Rev3UTR2T20 were used as primers for PCR. In addition, instead of IVT_S5prime_UTR, IVT_3prime_UTR was used as a template.

(3-3) Construction of IVT Template DNA of Control mRNA

The IVT template of control mRNA was constructed by performing PCR amplification, using the primers shown in Table 6 and the above-amplified PCR product.

(a) IVT_tagBFP

The following solution was prepared using KOD-Plus-Neo (KOD-401, TOYOBO) in accordance manufacturer's instructions.

TABLE 14

| Structural components | Final concentration |
| --- | --- |
| 10 × kod-plus-Neo buffer | 1× |
| 2 mM dNTPs | 200 μM |

TABLE 14-continued

| Structural components | Final concentration |
| --- | --- |
| 25 mM MgSO₄ aq | 1.5 mM |
| TAP_T7_G3C fwd primer | 0.3 μM |
| 3UTR120A rev primer | 0.3 μM |
| tagBFP PCT product | 0.2 ng/μL |
| 5'-UTR PCR product | 10 nM |
| 3'-UTR PCR product | 10 nM |
| 1 U/μL Kod + polymerase | 0.02 U/μL |
| D2W | |
| Final volume | 50 μL |

The prepared solution was subjected to PCR amplification under the following reaction conditions.

TABLE 15

| | | |
| --- | --- | --- |
| 94° C. | 2 minutes | |
| 98° C. | 10 seconds | 20 cycles |
| 68° C. | 45 seconds | |
| 15° C. | ∞ | |

The amplified PCR product was treated using Dpn I (TOYOBO) at 37° C. for 30 minutes, and thereafter, using MiniElute PCR purification Kit (QIAGEN), the reaction product was purified in accordance with manufacturer's instructions.

(b) IVT_EGFP PCR amplification was carried out by the same method as that in (a) above. Instead of the tagBFP PCR product, an EGFP PCR product was used as a template.

(c) IVT Puromycin

PCR amplification was carried out by the same method as that in (a) above. Instead of the tagBFP PCR product, a Puromycin PCR product was used as a template.

(d) IVT_Blasticidin

PCR amplification was carried out by the same method as that in (a) above. Instead of the tagBFP PCR product, a Blasticidin PCR product was used as a template.

(3-4) Construction of IVT Template of miRNA-Responsive mRNA

The IVT template of miRNA-responsive mRNA was constructed by performing PCR amplification, using the primers shown in Table 6 and the above-amplified PCR product. Moreover, instead of the 5'-UTR PCR product as used above, the 5'-UTR primers corresponding to miRNAs shown in the following Table 16 were used.

TABLE 16

| Name of primer | Sequence of 5'-UTR primer | SEQ ID NO: |
| --- | --- | --- |
| 5UTRtemp_let-7e-5p | CGACTCACTATAGGTTCCGCGATCGCGGATCCAACTATA<br>CAACCTCCTACCTCAAGATCACACCGGTCGCCACCATG | 94 |
| 5UTRtemp_T1 | CGACTCACTATAGGTTCCGCGATCGCGGATCCATACATA<br>CTTCTTTACATTCCAAGATCACACCGGTCGCCACCATG | 95 |
| 5UTRtemp_T22-5p | CGACTCACTATAGGTTCCGCGATCGCGGATCCTAAAGCT<br>TGCCACTGAAGAACTAGATCACACCGGTCGCCACCATG | 96 |
| 5UTRtemp_T133a-3p | CGACTCACTATAGGTTCCGCGATCGCGGATCCCAGCTGG<br>TTGAAGGGGACCAAAAGATCACACCGGTCGCCACCATG | 97 |
| 5UTRtemp_T133b | CGACTCACTATAGGTTCCGCGATCGCGGATCCTAGCTGG<br>TTGAAGGGGACCAAAAGATCACACCGGTCGCCACCATG | 98 |
| 5UTRtemp_T143-3p | CGACTCACTATAGGTTCCGCGATCGCGGATCCGAGCTAC<br>AGTGCTTCATCTCAAGATCAACACCGGTCGCCACCATG | 99 |
| 5UTRtemp_T145-3p | CGACTCACTATAGGTTCCGCGATCGCGGATCCAGAACAG<br>TATTTCCAGGAATCCAGATCACACCGGTCGCCACCATG | 100 |

TABLE 16-continued

| Name of primer | Sequence of 5'-UTR primer | SEQ ID NO: |
|---|---|---|
| 5UTRtemp_T208a-3p | CGACTCACTATAGGTTCCGCGATCGCGGATCCACAAGCT TTTTGCTCGTCTTATAGATCACACCGGTCGCCACCATG | 101 |
| 5UTRtemp_T490-5p | CGACTCACTATAGGTTCCGCGATCGCGGATCCACCCACC TGGAGATCCATGGAGATCAAACACCGGTCGCCACCATG | 102 |
| 5UTRtemp_T490-3p | CGACTCACTATAGGTTCCGCGATCGCGGATCCCAGCATG GAGTCCTCCAGGTTGAGATCACACCGGTCGCCACCATG | 103 |
| 5UTRtemp_T499a-5p | CGACTCACTATAGGTTCCGCGATCGCGGATCCAAACATC ACTGCAAGTCTTAAAGATCAACACCGGTCGCCACCATG | 104 |
| 5UTRtemp_T1271-5p | CGACTCACTATAGGTTCCGCGATCGCGGATCCTGAGTGC TTGCTAGGTGCCAAGAGATCACACCGGTCGCCACCATG | 105 |
| 5UTRtemp_T3907 | CGACTCACTATAGGTTCCGCGATCGCGGATCCTGTGAGC CAGCCTGGAGCACCTAGATCACACCGGTCGCCACCATG | 106 |
| 5UTRtemp_T4324 | CGACTCACTATAGGTTCCGCGATCGCGGATCCTTAAGGT TAGGGTCTCAGGGAGATCAAACACCGGTCGCCACCATG | 107 |
| 5UTRtemp_T208b | CGACTCACTATAGGTTCCGCGATCGCGGATCCACAAACC TTTTGTTCGTCTTATAGATCACACCGGTCGCCACCATG | 108 |

(a) IVT_tagBFP

The following solution was prepared using KOD-Plus-Neo (KOD-401, TOYOBO) in accordance with manufacturer's instructions.

TABLE 17

| Structural components | Final concentration |
|---|---|
| 10 × kod-plus-Neo buffer | 1× |
| 2 mM dNTPs | 200 µM |
| 25 mM MgSO$_4$ aq | 1.5 mM |
| TAP_T7_G3C fwd primer | 0.3 µM |
| 3UTR120A rev primer | 0.3 µM |
| tagBFP PCT product | 0.2 ng/µL |
| miRNA-responsive 5'-UTR PCR product | 10 nM |
| 3'-UTR PCR product | 10 nM |
| 1 U/µL Kod + polymerase | 0.02 U/µL |
| D2W | |
| Final volume | 50 µL |

The prepared solution was subjected to PCR amplification under the following reaction conditions.

TABLE 18

| 94° C. | 2 minutes | |
| 98° C. | 10 seconds | 20 cycles |
| 68° C. | 45 seconds | |
| 15° C. | ∞ | |

The amplified PCR product was treated using Dpn I (TOYOBO) at 37° C. for 30 minutes, and thereafter, using MiniElute PCR purification Kit (QIAGEN), the reaction product was purified in accordance with manufacturer's instructions.

(b) IVT_hdKeima-Red

PCR amplification was carried out by the same method as that in (a) above. Instead of the tagBFP PCR product, a hdKeima-Red PCR product was used as a template.

(c) IVT_Bim

PCR amplification was carried out by the same method as that in (a) above. Instead of the tagBFP PCR product, a Bim PCR product was used as a template.

(3-5) Synthesis and Generation of mRNA

Applying the protocols described in Warren L, et al., Cell Stem Cell. 7(5): 618-30 (2010), miRNA-responsive OFF switch mRNA was produced using MEGAscript T7 kit (Ambion). In this reaction, pseudo uridine-5'-triphosphate and methylcytidine-5'-triphosphate (TriLink BioTechnologies) were used, instead of uridine triphosphate and cytidine triphosphate, respectively. Before the IVT reaction (the synthesis of mRNA), guanidine-5'-triphosphate was 5-fold diluted with Anti Reverse Cap Analog (New England Biolabs). The reaction mixture was incubated at 37° C. for 5 hours, and TURBO DNase (Amibion) was then added to the resultant. Thereafter, the thus obtained mixture was further incubated at 37° C. for 30 minutes. Thereafter, the obtained mRNA was purified with FavorPrep Blood/Cultured Cells total RNA extraction column (Favorgen Biotech), and the resultant was then incubated at 37° C. for 30 minutes, using Antarctic Phosphatase (New England Biolabs). Thereafter, the resultant was further purified using RNeasy MiniElute Cleanup Kit (QIAGEN).

(4) Analysis Using miRNA-Responsive OFF Switch mRNA

In order to evaluate the produced miRNA-responsive OFF switch mRNA, the miRNA-responsive OFF switch mRNA, together with EGFP mRNA, was introduced into cardiomyocytes derived from hiPSC (201B7 line). Briefly, the cell population (EB) on the 16th day after initiation of the culture was treated with collagenase type I for 1 hour, and was then treated with trypsin for 5 to 10 minutes. To the thus treated cells, 50% FBS/IMDM was added to neutralize trypsin, and then, EB was gently agitated by pipetting, so as to dissociate the cells. Thereafter, the cells were centrifuged at 1000 rpm for 5 minutes and were then re-suspended in StemPro-34, to which 10 ng/ml VEGF and 5 ng/ml bFGF had been added. Thereafter, the cells were seeded in a concentration of 2×10$^5$ cells/well on a 24-well plate coated with fibronectin and were then incubated at 37° C. in 5% CO$_2$ for 2 days. Subsequently, using Stemfect RNA transfection kit, miRNA-responsive OFF switch mRNA was introduced into the cells in accordance with manufacturer's instructions (Stemgent). Specifically, 12.5 µl/tube Stemfect Transfection Buffer was placed in each of two sterilized 1.5-ml tubes. After that, 1.0 µl of Stemfect RNA Transfection Reagent was added to one tube, and it was then mixed with the buffer. To the other tube, 1.0 μl of 100 ng/μl miRNA-responsive OFF switch mRNA and 1.0 μl of 100 ng/μl EGFP mRNA were added, and were then mixed with the buffer. The diluted Transfection Reagent solution was added to the diluted mRNA solution, and the two solutions were mixed with each other. The obtained mixture was incubated at a room temperature for 15 minutes to complete an mRNA complex. During this operation, the culture medium was replaced with 500 μl of a fresh medium (StemPro-34 (not containing antibiotics), to which 10 ng/ml VEGF and 5 ng/ml bFGF had been added), and 15 minutes after the replacement of the medium, the mRNA complex was added to a well, and it was then incubated at 37° C. in 5% $CO_2$ for 4 hours. Thereafter, the medium was removed, the cells were washed once with IMDM, and 500 μl of a fresh medium (StemPro-34 (containing antibiotics), to which 10 ng/ml VEGF and 5 ng/ml bFGF had been added) was added to the well. The obtained mixture was cultured for 2 days, and thereafter, the fluorescence intensity of BFP was analyzed by FACS. In the FACS analysis, briefly speaking, the recovered cell population (EB) was treated with trypsin for 2 minutes, and then, 50% FBS/LMDM was added to the treated cell population to neutralize trypsin. Thereafter, the cells were centrifuged at 1000 rpm for 5 minutes and were then re-suspended in PBS to which 2% FBS had been added. Thereafter, the cells were subjected to the FACS analysis.

Figure 2:
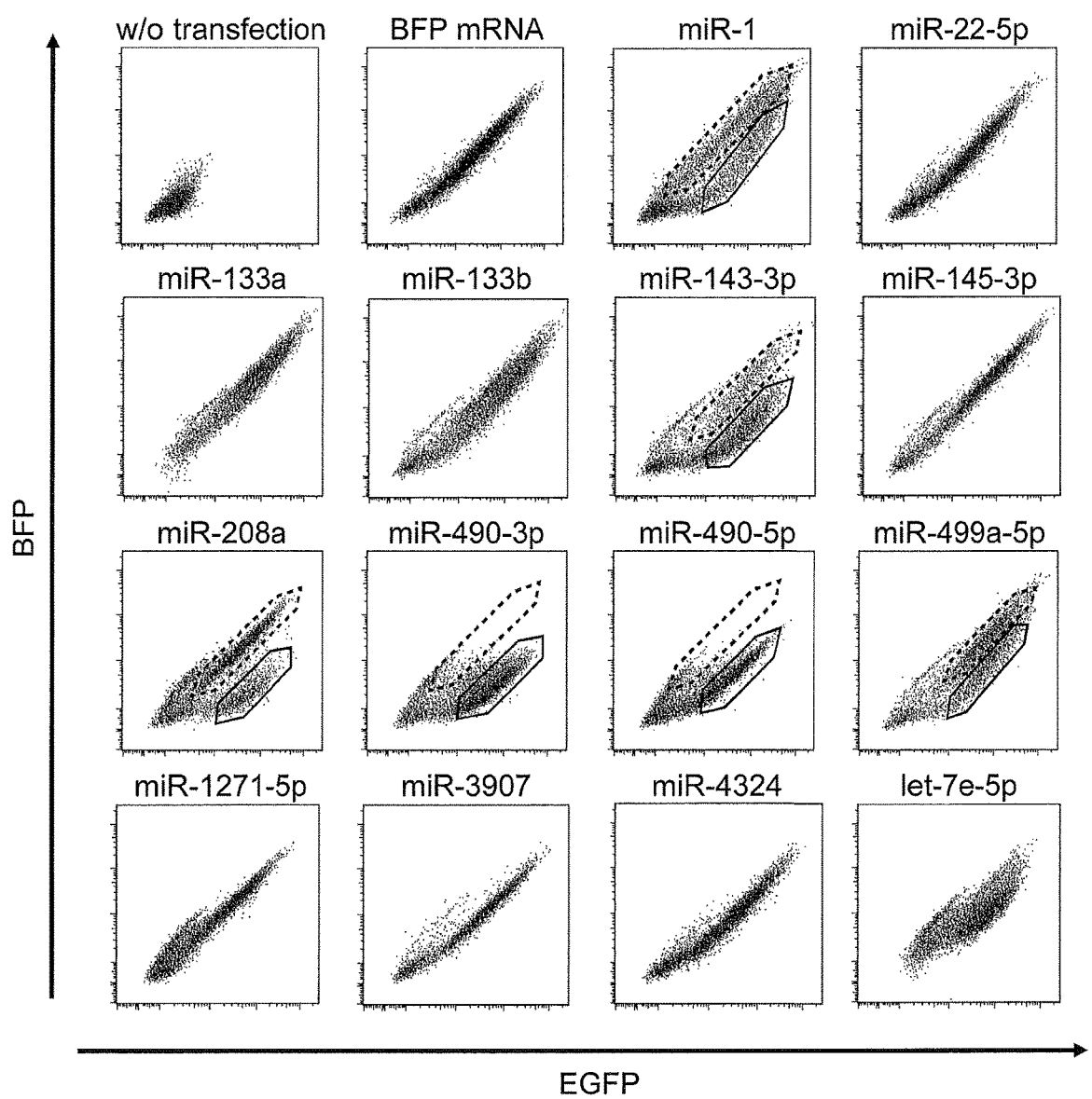
FIG. 2 shows the results of an analysis using miRNA-responsive OFF switch mRNA.

As a result, some cells, into which each of miR-1-, miR-143-3p-, miR-208a-, and miR-499a-5p-responsive OFF switch mRNAs had been introduced, had the fluorescence intensity of TagBFP that was lower than that in the case of introducing TagBFP mRNA (control) (FIG. 2). On the other hand, a majority of cells, into which each of miR-490-3p and -490-5p-responsive OFF switch mRNAs had been introduced, had the fluorescence intensity of Tag-BFP that was lower than that in the case of introducing TagBFP mRNA (control), and cells, into which each of 8 other miRNA-responsive OFF switch mRNAs had been introduced, did not show such reactions (FIG. 2). Therefore, miR-1-, miR-143-3p-, miR-208a-, and miR-499a-5p-responsive OFF switch mRNAs were identified as candidate substances for purification of cardiomyocytes.

Example 3

Purification of Cardiomyocytes (1-1)

In order to examine the effectiveness of miR-1-, miR-143-3p-, miR-208a-, and miR-499a-5p-responsive OFF switch mRNAs in purification of cardiomyocytes, an experiment was continuously carried out. The 201B7 line was induced to differentiate into cardiomyocytes according to the method for inducing cells to differentiate into cardiomyocytes of Example 1, and on the 20th day after the induction, cells with reduced TagBFP signals were sorted by FACS, and the expression of TNT was then analyzed. Briefly, the expression of TNT was analyzed as follows. The sorted cell group was immobilized with 4% paraformaldehyde in PBS and was then stained with an anti-myocardial TNT isoform (clone 13-11; Thermo; 1:200) in PBS containing 2% FBS and 0.5% saponin (Sigma). As a secondary antibody, APC goat anti-mouse Ig (BD Pharmingen; 1:100) was used. Responsive OFF switch mRNA was introduced into cells by the same method as that described in Example 2(4).

Figure 3A:
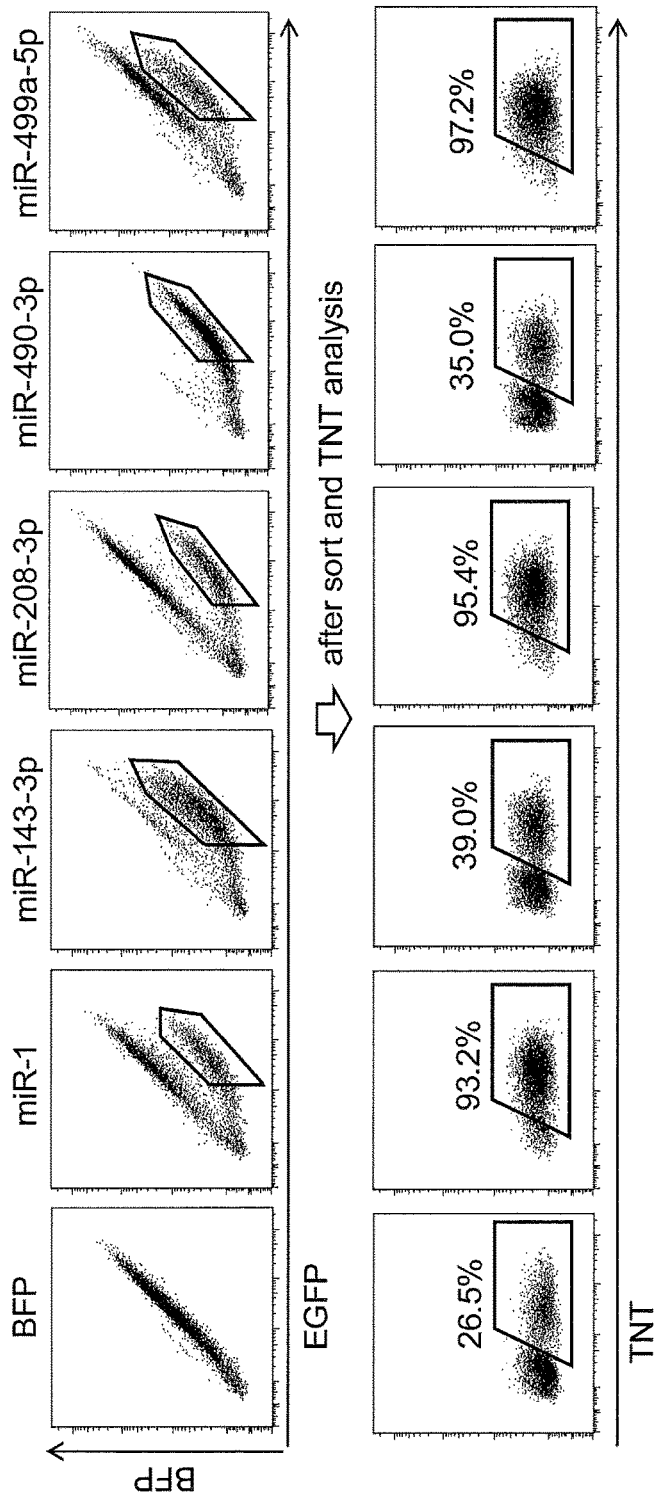
FIGS. 3(A) and 3(B) show the results obtained by examining the effectiveness of miRNA-responsive OFF switch mRNA in purification of cardiomyocytes. 3(A): Using, as an indicator, TNT specifically expressed in cardiomyocytes, the degree of purification of cardiomyocytes was examined. 3(B): shows that miR-143-3p and miR-490-3p-responsive OFF switch mRNAs provided the same level of purification degree as in a case in which the cells were not sorted.
Figure 3B:
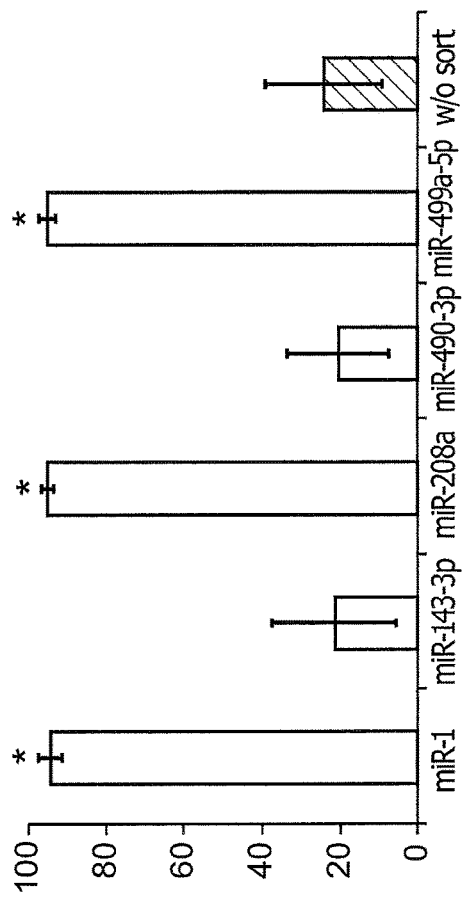

As a result of the flow cytometric analysis, miR-1-, miR-208a-, and miR-499a-5p-responsive OFF switch mRNAs were effective for TNT-positive cardiomyocytes to show a high degree of purification. On the other hand, miR-143-3p and miR-490-3p-responsive OFF switch mRNAs provided the same level of purification degree as in a case in which the cells were not sorted (FIGS. 3(A) and 3(B)).

Figure 4A:
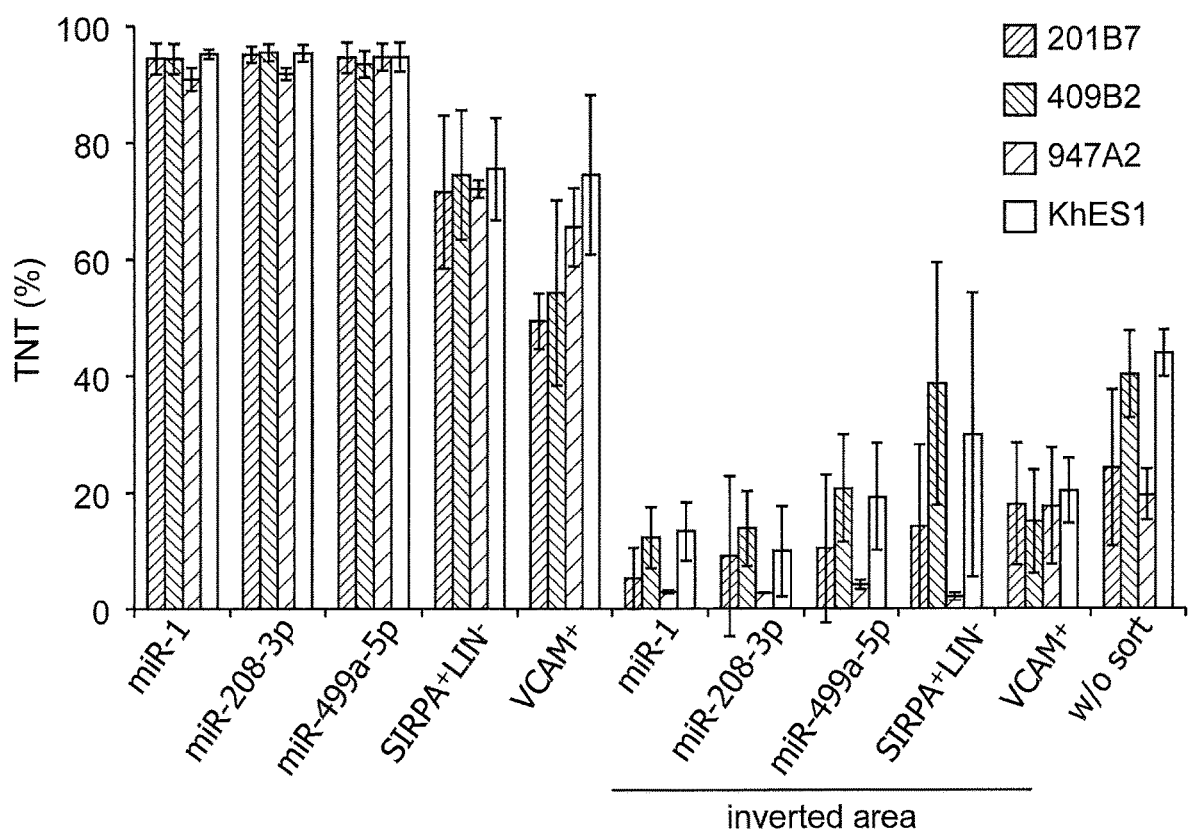
FIGS. 4(A) and 4(B) show the results obtained by examining the effectiveness of miRNA-responsive OFF switch mRNA in a cell population that has been subjected to a step of inducing differentiation of various types of pluripotent stem cells (PSCs) into cardiomyocytes. 4(A): shows that miR-1-, miR-208a-, and miR-499a-5p-responsive OFF switch mRNAs also functions in hPSC lines other than the 201B7 line, and an analysis was carried out using two different types of hiPSC lines (409B2 and 947A2) and one type of hESC line (KhES1). 4(B): Using, as an indicator, TNT specifically expressed in cardiomyocytes, the degree of purification of cardiomyocytes was examined. The mRNA that does not comprise a miRNA-responsive sequence was used as a control.
Figure 4B:
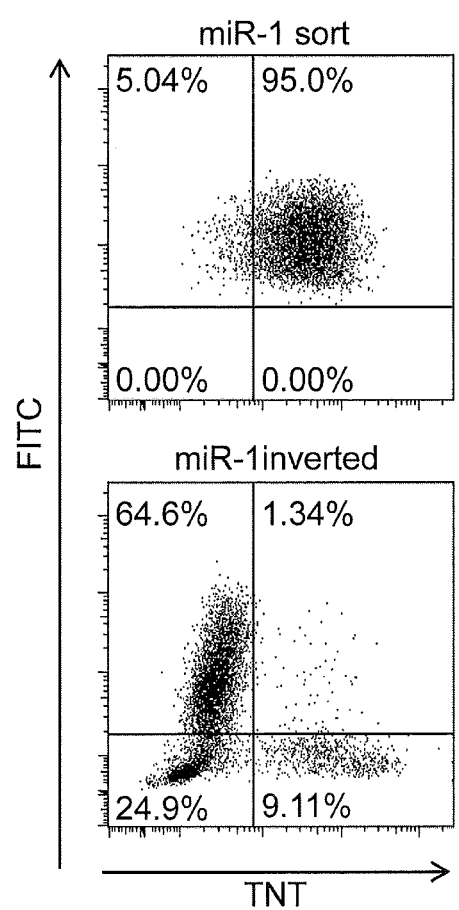

Subsequently, in order to confirm that miR-1-, miR-208a-, and miR-499a-5p-responsive OFF switch mRNAs also function in hPSC lines other than the 201B7 line, an analysis was carried out, using two different types of hiPSC lines (409B2 and 947A2) and one type of hESC line (KhES1). As a result, as in the case of using the 201B7 line, a TNT-positive cardiomyocyte population could be sorted at high purity (FIGS. 4(A) and 4(B)).

Figure 5:
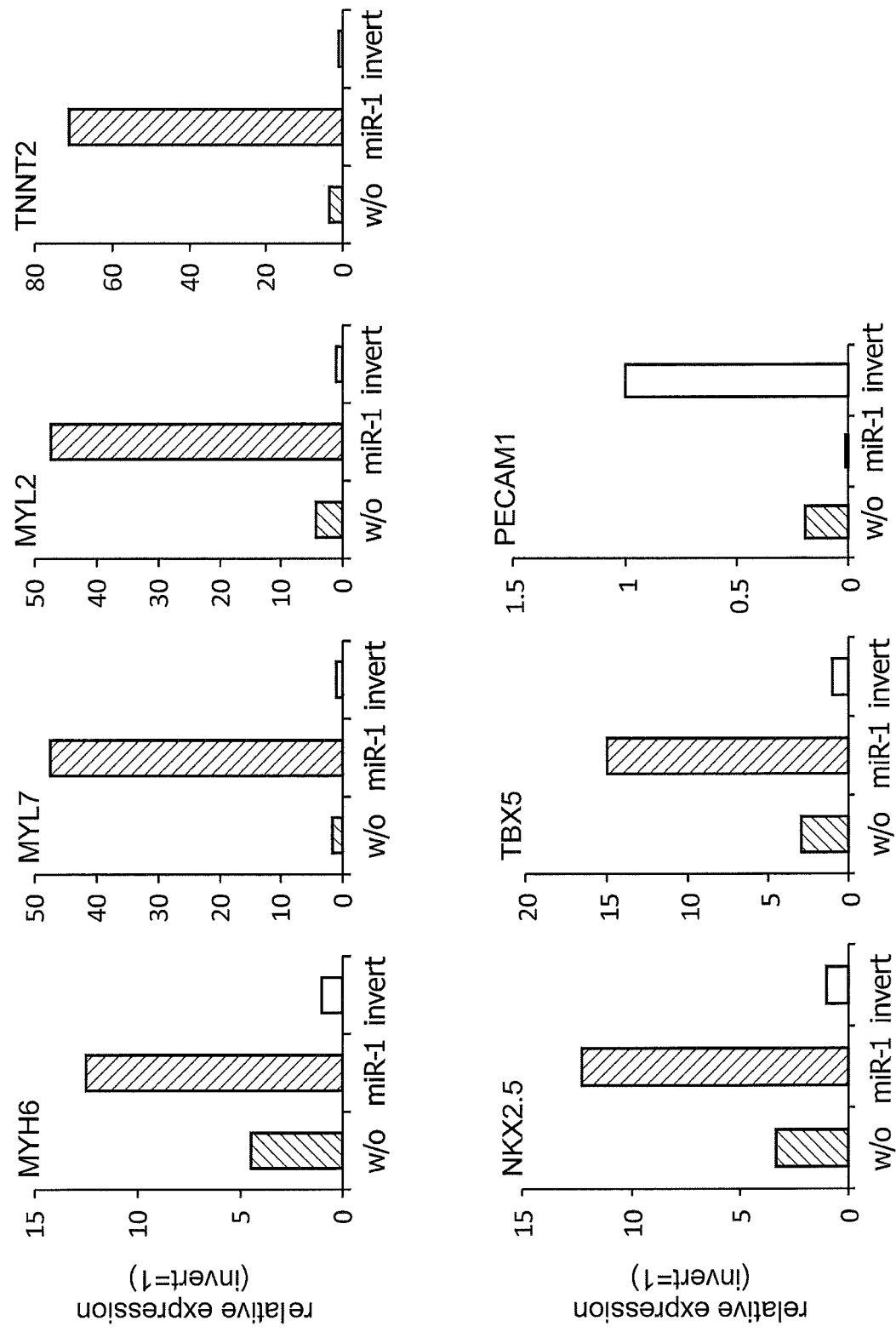
FIG. 5 shows the results obtained by examining the expression state of a myocardium-specific gene in cells that have been sorted using miR-1-responsive OFF switch mRNA. The expression was analyzed according to quantitative RT-PCR.
Figure 6:
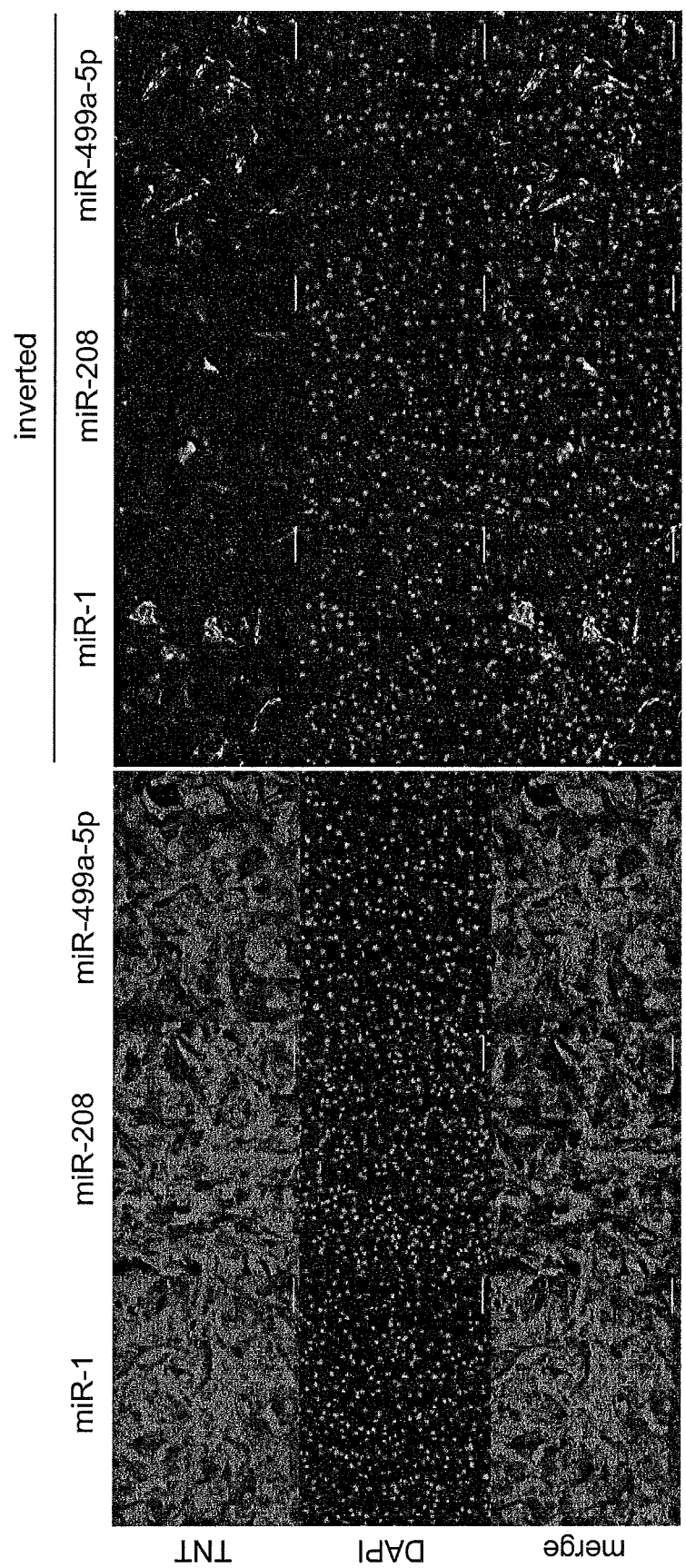
FIG. 6 shows the results obtained by examining the expression state of a myocardium-specific gene at a protein level in cells that have been sorted using miR-1-, miR-208a-, and miR-499a-5p-responsive OFF switch mRNAs. The analysis was carried out by performing immunostaining on TNT.

The obtained TNT-positive cardiomyocytes were examined in terms of the expression state of myocardium-specific expression gene. As a result, it was confirmed that the myocardium-specific gene was expressed at high levels, that is, both at the mRNA level and at the protein level (FIGS. 5 and 6).

Figure 7:
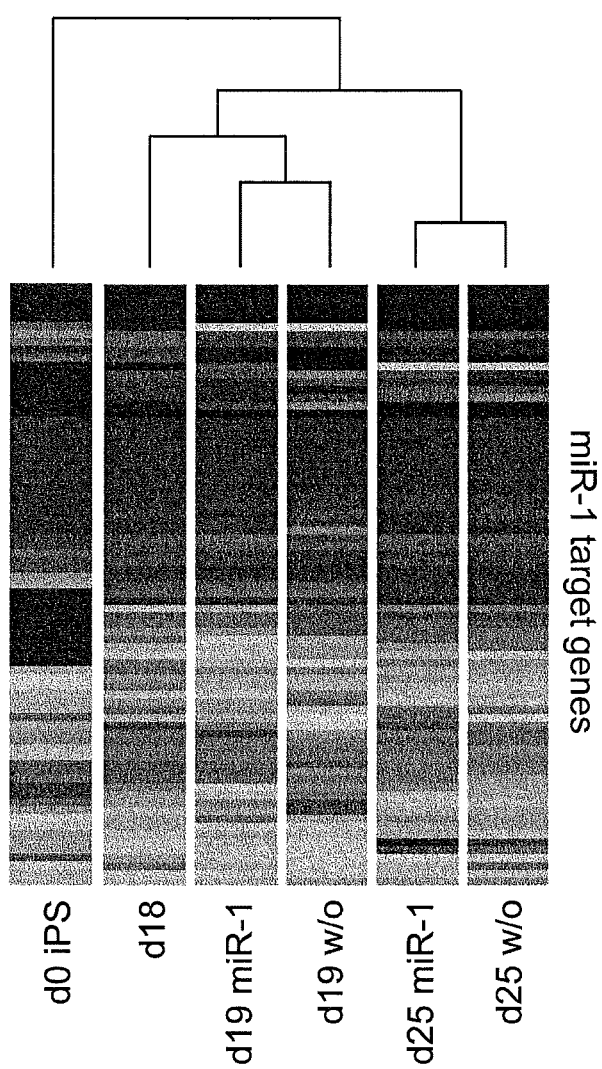
FIG. 7 shows the results obtained by examining the expression state of a miR-1 target gene in a case in which miR-1-responsive OFF switch mRNA has been introduced and in a case in which miR-1-responsive OFF switch mRNA has not been introduced. After completion of the analysis according to microarray, 54 miR-1 target genes were evaluated.

Moreover, in order to confirm whether or not the introduced miRNA-responsive OFF switch mRNA acts with endogenous miRNA so that it inhibits the function of the endogenous miRNA in cells, an experiment was carried out. Briefly, the MYH6-EIP6-introduced cell line produced by the same method as that of Example 2 was induced to differentiate into cardiomyocytes by the method of Example 1. On the 16th day after the differentiation, the cells were sorted using GFP, and two days after the sorting (18th day), miR-1-responsive OFF switch mRNA was introduced into the cells. Herein, a cell group, into which miR-1-responsive OFF switch mRNA had not been introduced, was also prepared. On the 19th and 25th days, total RNA was extracted, and was then analyzed using a microarray. As a result, regardless of whether or not the miRNA-responsive mRNA had been introduced into the cells, the miR-1 target gene exhibited similar expression tendency. Thus, it was suggested that miRNA-responsive mRNA does not give a negative influence on the cardiomyocytes, into which it has been introduced (FIG. 7).

Example 4

Purification of Cardiomyocytes (1-2)

In order to examine the effectiveness of a combination of multiple miRNA-responsive OFF switch mRNAs in purification of cardiomyocytes, the following experiment was carried out. That is, the 201B7 line was induced to differentiate into cardiomyocytes, and miRNA-responsive OFF switch mRNA was then introduced into the cells. Thereafter, whether or not the cardiomyocytes could be purified at high purity by soring using FACS was confirmed. The 201B7 line was induced to differentiate into cardiomyocytes by the same method as that of Example 1, and the miRNA-responsive OFF switch mRNA was introduced into the cells by the same method as that of Example 2(4).

Figure 8:
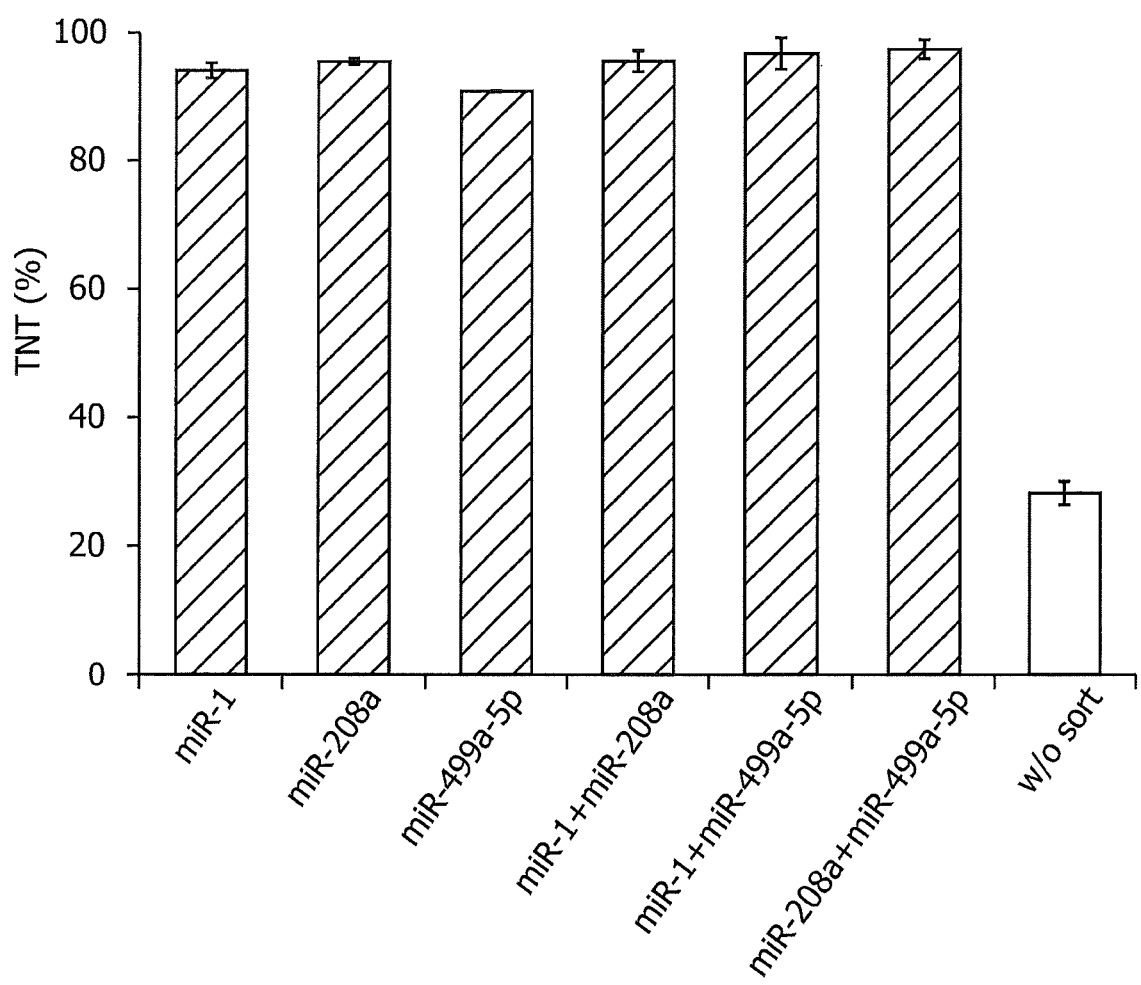
FIG. 8 shows the results obtained by examining the effectiveness of a combination of multiple miRNA-responsive OFF switch mRNAs in purification of cardiomyocytes. Using, as an indicator, TNT specifically expressed in cardiomyocytes, the degree of purification of cardiomyocytes was examined.

As a result, when a combination of miR-1-+miR-208a-, miR-1-+miR-499a-5p-, and miR-208a-+miR-499a-5p- was introduced into the cells, the combination exhibited purification efficiency that was equivalent to, or was somewhat superior to the case of a single use of miR-1-, miR-208a-, or miR-499a-5p- (FIG. 8).

Example 5

Purification of Cardiomyocytes (2)

In order to examine the cardiomyocyte-purifying effect obtained when miRNA-responsive OFF switch mRNA and drug-resistant mRNA were co-introduced into cells, an experiment was carried out. The KhES1 line was induced to differentiate into cardiomyocytes by the method for inducing cells to differentiate into cardiomyocytes of Example 1. Then, miRNA-responsive OFF switch mRNA and drug-resistant mRNA were introduced into the cells as follows. Briefly, the cell population (EB) on the 16th day after initiation of the culture was treated with collagenase type I for 1 hour, and was then treated with 0.25% trypsin for 5 to 10 minutes. To the thus treated cells, 50% FBS/IMDM was added to neutralize trypsin, and then, EB was gently agitated by pipetting, so as to dissociate the cells. Thereafter, the cells were centrifuged at 1000 rpm for 5 minutes, and were then re-suspended in StemPro-34, to which 10 ng/ml VEGF and 5 ng/ml bFGF had been added. Thereafter, the cells were seeded in a concentration of $5 \times 10^5$ cells/well on a 12-well plate coated with fibronectin, and were then incubated at 37° C. in 5% $CO_2$ for 2 days. Subsequently, using Stemfect RNA transfection kit, miRNA-responsive OFF switch mRNA was introduced into the cells in accordance with manufacturer's instructions (Stemgent). Specifically, 25 p/tube Stemfect Transfection Buffer was placed in each of two sterilized 1.5-ml tubes. After that, 2 µl of Stemfect RNA Transfection Reagent was added to one tube, and it was then mixed with the buffer. To the other tube, 0.5 µl or 1.0 µl of 100 ng/µl puromycin mRNA (Puromycin) and 0.5 µl to 2.0 µl of 100 ng/µl miR-1-responsive Bim mRNA (miR-1-HsBimEL) were added, and were then mixed with the buffer. The diluted Transfection Reagent solution was added to the diluted mRNA solution, and the two solutions were mixed with each other. The obtained mixture was incubated at a room temperature for 15 minutes to complete an mRNA complex. During this operation, the medium was replaced with 500 µl of fresh medium (StemPro-34 (not containing antibiotics), to which 10 ng/ml VEGF and 5 ng/ml bFGF had been added), and 15 minutes after the replacement of the medium, the mRNA complex was added to a well, and it was then incubated at 37° C. in 5% $CO_2$ for 4 hours. Thereafter, the medium was removed, the cells were washed once with IMDM, and 500 µl of a fresh medium (StemPro-34, to which 10 ng/ml VEGF and 5 ng/ml bFGF had been added), to which puromycin had been added, was added to the well. The obtained mixture was cultured for 2 days, and thereafter, the expression of TNT was analyzed.

Figure 9A:
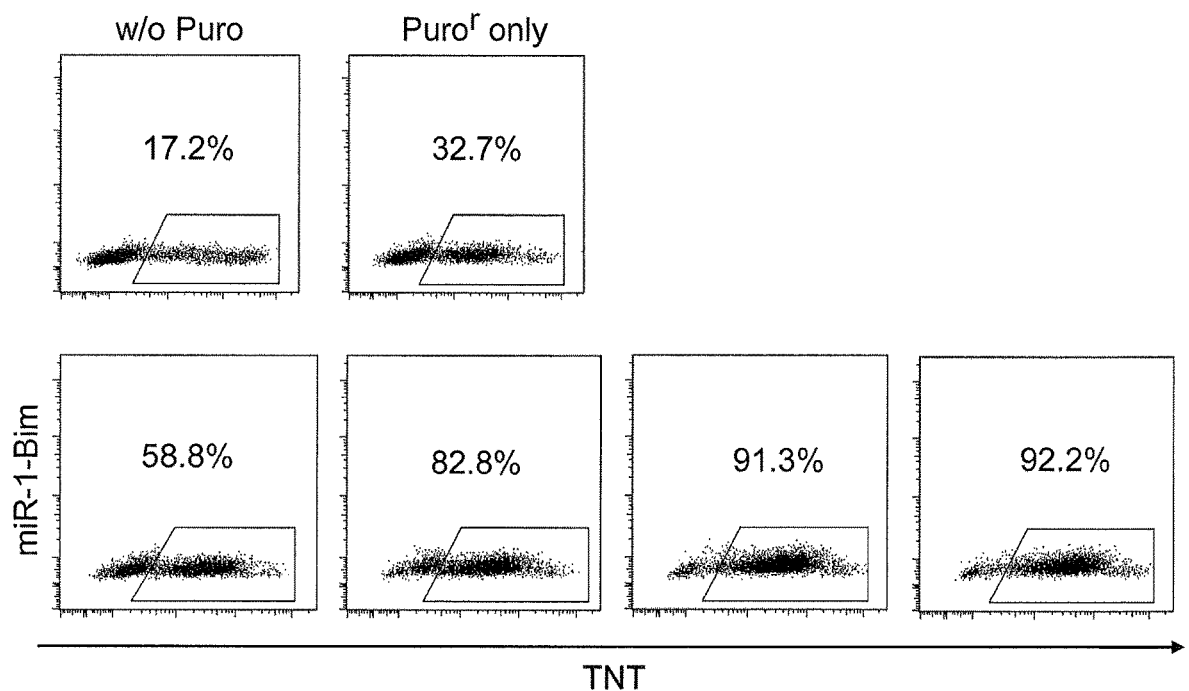
FIGS. 9(A) and 9(B) show the results obtained by examining the effect of purifying cardiomyocytes upon co-introduction of miRNA-responsive OFF switch mRNA and drug resistant mRNA into the cells. 9(A): The results obtained in a case in which KhES1 has been induced to differentiate. 9(B): The results obtained in a case in which 409B2 has been induced to differentiate. Using, as an indicator, TNT specifically expressed in cardiomyocytes, the degree of purification of cardiomyocytes was examined.
Figure 9B:
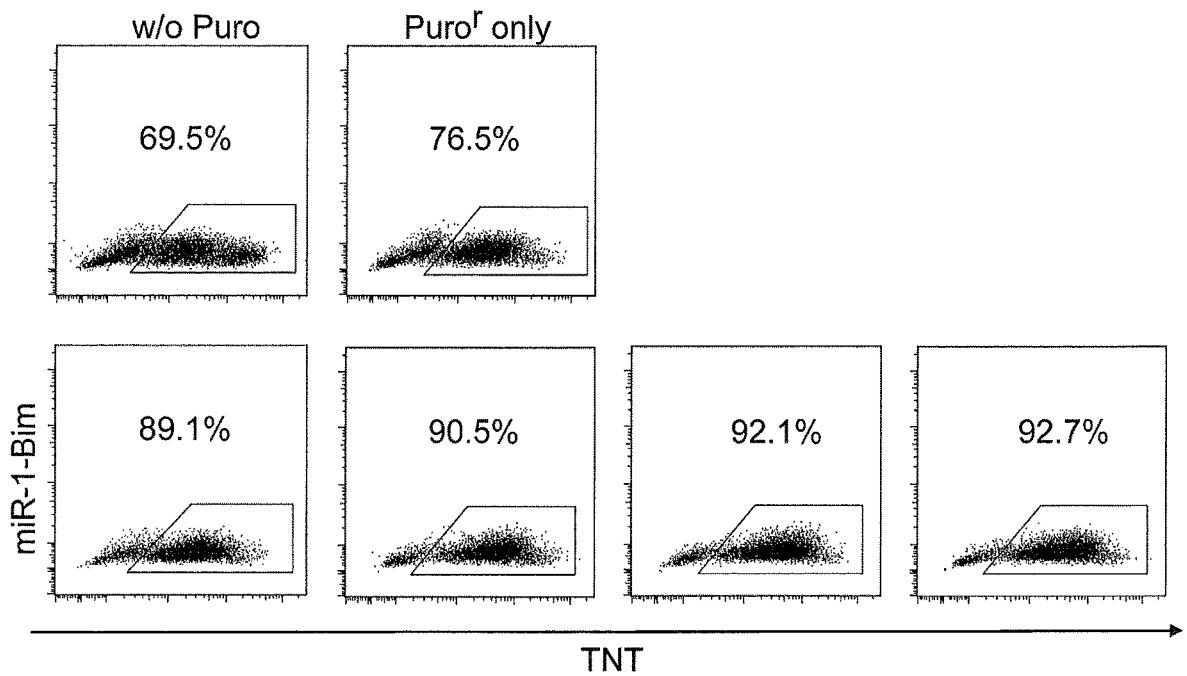

As a result, it was demonstrated that when puromycin mRNA (Puromycin) and miR-1-HsBimEL are co-introduced into the cells, cardiomyocytes can be purified at an extremely high purity (92.2% in the present example), without performing a sorting operation (FIGS. 9(A) and 9(B)).

Example 6

Figure 10:
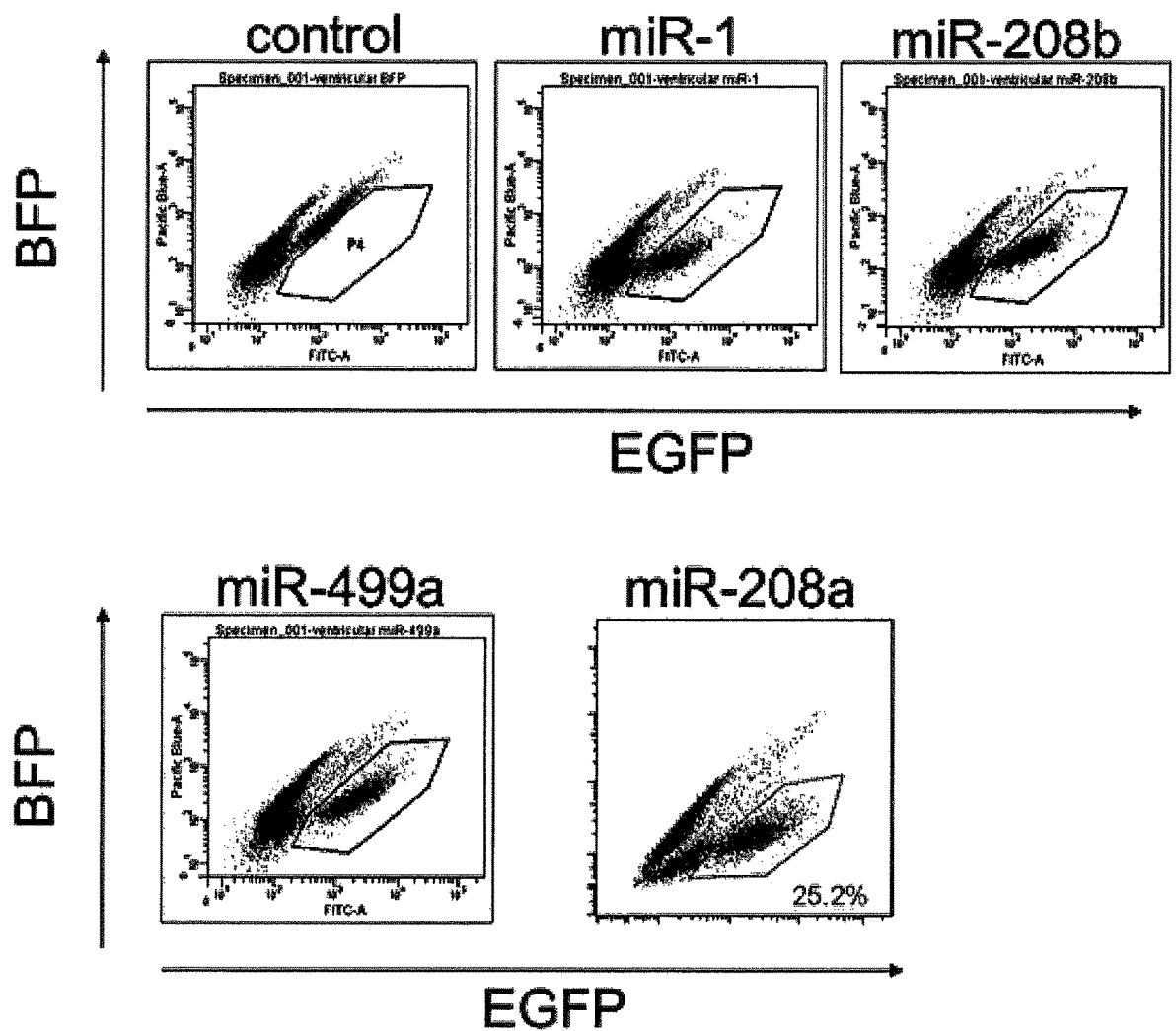
FIG. 10 shows the results of an analysis performed after co-introduction of each of miR-1-, miR-208a-, miR-208b-, and miR-499a-5p-responsive OFF switch mRNAs, together with EGFP, into cells derived from mouse heart. In the figure, the region encompassed with a line indicates cardiomyocytes.

Using Neonatal Heart Dissociation Kit (Miltenyi Biotech), a heart isolated from a neonatal mouse was separated into single cells in accordance with manufacturer's instructions, and thereafter, the thus separated cells were seeded in a concentration of $2 \times 10^5$ cell/well on a 24-well plate and were then incubated at 37° C. On the following day, using Stemfect RNA transfection Kit (Stemgent), 100 ng of each of miR-1-, miR-143-3p-, miR-208a-, miR-208b-, and miR-499a-5p-responsive OFF switch mRNAs (BFPs), together with 100 ng of EGFP mRNA, was introduced into the cells in accordance with manufacturer's instructions. Four hours later, the cells were washed, and DMEM+10% FBS were then added to the resulting cells, followed by performing a culture for 1 day. Thereafter, the obtained cells were treated with 0.250/% trypsin for 2 minutes, and the fluorescence intensities of BFP and EGFP were analyzed by FACS. As a result, among the cells to which miR-1-, miR-143-3p-, miR-208a-, miR-208b-, and miR-499a-5p-responsive OFF switch mRNAs had been introduced, there were cells, in which the fluorescence intensity of EGFP was high and the fluorescence intensity of BFP was reduced (FIG. 10). Therefore, it was suggested that miR-1-BFP, miR-208b-BFP, miR-208a-BFP, and miR-499a-5p-BFP can specifically recognize cells contained in the heart comprising cardiomyocytes.

INDUSTRIAL APPLICABILITY

The present invention provides methods for sorting and producing cardiomyocytes, which are capable of easily purifying cardiomyocytes. Accordingly, it becomes possible to provide highly pure cardiomyocytes, which are used for the treatment of heart diseases such as heart failure, ischemic heart disease, myocardial infarction, cardiomyopathy, myocarditis, hypertrophic cardiomyopathy, dilated phase of hypertrophic cardiomyopathy and dilated cardiomyopathy.
[Sequence Listing]

The invention claimed is:

1. A method for providing cells useful for sorting cardiomyocytes, comprising steps of:
   (A) introducing miRNA-responsive mRNA into a cell group, wherein the miRNA-responsive mRNA comprises a sequence having:
   (a) a cap structure;
   (b) a 5' untranslated region (5'-UTR);
   (c) an open reading frame comprising a nucleic acid corresponding to the coding region of a gene;
   (d) a 3' untranslated region (3'-UTR); and
   (e) a poly (A) tail region,
   wherein the 5'-UTR comprises a nucleic acid specifically recognized by miRNA specifically expressed in cardiomyocytes,
   wherein the miRNA-responsive mRNA is introduced into the cell group in a form of a synthetic RNA molecule without using a DNA or virus vector, and
   wherein translation of the nucleic acid corresponding to the coding region of a gene into protein is regulated by the nucleic acid specifically recognized by miRNA specifically expressed in cardiomyocytes; and
   (B) inhibiting translation of the coding region of the gene in response to the presence of an miRNA specifically expressed in the cardiomyocytes or performing translation of the coding region of the gene in response to the absence of an miRNA specifically expressed in the cardiomyocytes.

2. The method according to claim 1, wherein the 3'-UTR comprises a nucleic acid specifically recognized by miRNA specifically expressed in cardiomyocytes.

3. The method according to claim 1, wherein the miRNA specifically expressed in cardiomyocytes is one or more miRNAs selected from the group consisting of miR-1, miR-208a, miR-208b and miR-499a-5p.

4. The method according to claim 1, wherein the gene in (c) is one or more genes selected from the group consisting of a gene encoding a fluorescent protein, an apoptosis-inducing gene and a suicide gene.

5. The method according to claim 4, wherein the gene encoding a fluorescent protein is a gene encoding a blue fluorescent protein (BFP).

6. The method according to claim 4, wherein the apoptosis-inducing gene is a gene encoding a Bim protein.

7. The method according to claim 1, further comprising a step of introducing mRNA consisting of a sequence comprising a nucleic acid corresponding to the coding region of a drug resistance gene into the cell group.

8. The method according to claim 7, wherein the drug resistance gene is an antibiotic resistance gene.

9. The method according to claim 8, wherein the antibiotic resistance gene is a puromycin resistance gene or a blasticidin resistance gene.

10. The method according to claim 1, wherein the cell group of step (A) is a cell group that has been induced to differentiate from pluripotent stem cells.

11. A method for producing cardiomyocytes, comprising the following steps:
(A) introducing miRNA-responsive mRNA into a cell group, wherein the miRNA-responsive mRNA comprises a sequence having:
   (a) a cap structure;
   (b) a 5' untranslated region (5'-UTR);
   (c) an open reading frame comprising a nucleic acid corresponding to the coding region of a gene;
   (d) a 3' untranslated region (3'-UTR); and
   (e) a poly (A) tail region,
   wherein the 5'-UTR comprises a nucleic acid specifically recognized by miRNA specifically expressed in cardiomyocytes, and
   wherein the miRNA-responsive mRNA is introduced into the cell group in a form of a synthetic RNA molecule without using a DNA or virus vector;
(B) inhibiting translation of the coding region of the gene in response to the presence of an miRNA specifically expressed in the cardiomyocytes or performing translation of the coding region of the gene in response to the absence of an miRNA specifically expressed in the cardiomyocytes; and
(C) sorting the cells based on a translation level of a protein from the mRNA of step (A), wherein high-purity cardiomyocytes can be obtained compared with a case in which steps (A), (B), and (C) are not carried out.

12. The method according to claim 1, further comprising before step (A), a step of inducing and differentiating pluripotent stem cells into cardiomyocytes to prepare the cell group.

13. The method according to claim 12, wherein the inducing and differentiating step comprises the following substeps (1) to (3):
(1) culturing the pluripotent stem cells in a culture medium containing BMP, bFGF and Activin A;
(2) culturing the pluripotent stem cells in a culture medium containing VEGF and a Wnt inhibitor; and
(3) culturing the pluripotent stem cells in a culture medium containing VEGF and bFGF.

14. The method according to claim 11, wherein the 3'-UTR comprises a nucleic acid specifically recognized by miRNA specifically expressed in cardiomyocytes.

15. The method according to claim 11, wherein the miRNA specifically expressed in cardiomyocytes is one or more miRNAs selected from the group consisting of miR-1, miR-208a, miR-208b and miR-499a-5p.

16. The method according to claim 11, wherein the gene in (c) is a gene encoding a fluorescent protein.

17. The method according to claim 16, wherein the gene encoding a fluorescent protein is a gene encoding BFP.

18. The method according to claim 11, wherein the cell group of step (A) is a cell group that has been induced to differentiate from pluripotent stem calls.

19. A method for producing cardiomyocytes, comprising:
(A) introducing miRNA-responsive mRNA and mRNA consisting of a sequence comprising a nucleic acid corresponding to the coding region of a drug resistance gene into a cell group, and
(B) culturing the cell group obtained in step (A) in the presence of a drug corresponding to the drug resistance gene of step (A) wherein the miRNA-responsive mRNA comprises a sequence having:
   (a) a cap structure;
   (b) a 5' untranslated region (5'-UTR);
   (c) an open reading frame comprising a nucleic acid corresponding to the coding region of a gene;
   (d) a 3' untranslated region (3'-UTR); and
   (e) a poly (A) tail region,
   wherein the 5'-UTR comprises a nucleic acid specifically recognized by miRNA specifically expressed in cardiomyocytes,
   wherein the miRNA-responsive mRNA is introduced into the cell group in a form of a synthetic RNA molecule without using a DNA or virus vector, and
   wherein high-purity cardiomyocytes can be obtained compared with a case in which steps (A) and (B) are not carried out.

20. The method according to claim 19, wherein the miRNA-responsive mRNA is miRNA-responsive OFF switch mRNA.

21. The method according to claim 19, wherein the 3'-UTR comprises a nucleic acid specifically recognized by miRNA specifically expressed in cardiomyocytes.

22. The method according to claim 19, wherein the miRNA specifically expressed in cardiomyocytes is one or more miRNAs selected from the group consisting of miR-1, miR-208a, miR-208b and miR-499a-5p.

23. The method according to claim 19, wherein the gene in (c) is an apoptosis-inducing gene and/or a suicide gene.

24. The method according to claim 23, wherein the apoptosis-inducing gene is a gene encoding a Bim protein.

25. The method according to claim 19, wherein the drug resistance gene is an antibiotic resistance gene.

26. The method according to claim 25, wherein the antibiotic resistance gene is a puromycin resistance gene or a blasticidin resistance gene.

27. The method according to claim 19, wherein the cell group of step (A) is a cell group that has been induced to differentiate from pluripotent stem cells.

28. A kit for purifying cardiomyocytes, comprising a synthetic miRNA-responsive mRNA, wherein the miRNA-responsive mRNA comprises a sequence having:
(a) a cap structure;
(b) a 5' untranslated region (5'-UTR);
(c) an open reading frame comprising a nucleic acid corresponding to the coding region of a gene;
(d) a 3' untranslated region (3'-UTR); and
(e) a poly (A) tail region,
wherein the 5'-UTR comprises a nucleic acid specifically recognized by miRNA specifically expressed in cardiomyocytes.

29. The kit according to claim 28, wherein the 3'-UTR comprises a nucleic acid specifically recognized by miRNA specifically expressed in cardiomyocytes.

* * * * *

UNITED STATES PATENT AND TRADEMARK OFFICE
CERTIFICATE OF CORRECTION

PATENT NO.         : 10,538,740 B2
APPLICATION NO.    : 15/127134
DATED              : January 21, 2020
INVENTOR(S)        : Yoshida et al.

Page 1 of 1

It is certified that error appears in the above-identified patent and that said Letters Patent is hereby corrected as shown below:

In the Specification

Column 8, Line 7: Please correct "Sal14" to read -- Sall4 --

Signed and Sealed this
Fourth Day of August, 2020

Andrei Iancu
*Director of the United States Patent and Trademark Office*